US012440529B2

(12) United States Patent
Pekoe et al.

(10) Patent No.: US 12,440,529 B2
(45) Date of Patent: *Oct. 14, 2025

(54) TOPICAL *CROTON LECHLERI* COMPOSITIONS AND THEIR USE IN THE TREATMENT OF A BACTERIAL COLONIZATION OR PRIMARY OR SECONDARY BACTERIAL INFECTION OF AN UNDERLYING SKIN DISORDER

(71) Applicant: ALPHYN BIOLOGICS, INC., Annapolis, MD (US)

(72) Inventors: Gary Michael Pekoe, Cincinnati, OH (US); Jazmyne Kristyne Mink, Cincinnati, OH (US); Steven Aaron Pentelnik, Cincinnati, OH (US); Neal G. Koller, Annapolis, MD (US)

(73) Assignee: Alphyn Biologics, Inc., Annapolis, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/482,369

(22) Filed: Sep. 22, 2021

(65) Prior Publication Data

US 2022/0110992 A1 Apr. 14, 2022

Related U.S. Application Data

(60) Provisional application No. 63/081,657, filed on Sep. 22, 2020, provisional application No. 63/081,665, filed on Sep. 22, 2020.

(51) Int. Cl.

| | |
|---|---|
| ***A61K 36/47*** | (2006.01) |
| ***A61K 31/343*** | (2006.01) |
| ***A61K 31/352*** | (2006.01) |
| ***A61K 31/353*** | (2006.01) |
| ***A61P 31/04*** | (2006.01) |

(52) U.S. Cl.

CPC ............ *A61K 36/47* (2013.01); *A61K 31/343* (2013.01); *A61K 31/352* (2013.01); *A61K 31/353* (2013.01); *A61P 31/04* (2018.01)

(58) Field of Classification Search

CPC .... A61K 36/47; A61K 31/343; A61K 31/352; A61K 31/353; A61K 2300/00; A61P 31/04; Y02A 50/30

See application file for complete search history.

(56) References Cited

U.S. PATENT DOCUMENTS

| | | | | |
|---|---|---|---|---|
| 12,150,970 | B2 | 11/2024 | Pekoe et al. | |
| 2002/0119997 | A1 | 8/2002 | Bader et al. | |
| 2008/0166426 | A1* | 7/2008 | Pekoe | A61P 31/04 424/769 |
| 2012/0190661 | A1 | 7/2012 | Trogden et al. | |
| 2016/0075665 | A1* | 3/2016 | Page | C07C 281/16 544/323 |
| 2016/0338973 | A1 | 11/2016 | Sonti et al. | |
| 2019/0021989 | A1 | 1/2019 | Cantina et al. | |
| 2020/0147001 | A1* | 5/2020 | Kraus | A61K 9/107 |
| 2022/0105147 | A1 | 4/2022 | Pekoe et al. | |
| 2022/0110992 | A1 | 4/2022 | Pekoe et al. | |
| 2022/0280584 | A1 | 9/2022 | Pekoe et al. | |

FOREIGN PATENT DOCUMENTS

| | | | | |
|---|---|---|---|---|
| CN | 101940574 | A | 1/2011 | |
| FR | 2852842 | A1 | 10/2004 | |
| WO | WO-2011024049 | A2 * | 3/2011 | A61K 31/353 |
| WO | 2012/101008 | A1 | 8/2012 | |
| WO | 2020058992 | A1 | 3/2020 | |
| WO | 2020191384 | A1 | 9/2020 | |
| WO | 2021/034986 | A1 | 2/2021 | |

OTHER PUBLICATIONS

Fischer et al. Journal of Ethnopharmacology, 93 (2004) 351-357 (Year: 2004).*

Gutierrez et al. J Clin. Investigat Dermatol, Feb. 2020, vol. 8, Iss 1. (Year: 2020).*

Pereira. An Bras Dermatol. 2014, 89(2): 293-299 (Year: 2014).*

Chen. Planta Med. 60 (1994), 541-545 (Year: 1994).*

Gupta, Journal of Ethnopharmacology 115, 2008, 361-380 (Year: 2008).*

Megna, Dermatol Ther. (Heidelb) (2017)7:1-23 (Year: 2017).*

Yosipovitch, Am. J. Clin. Dermatol 2003: 4(9): 617-622 (Year: 2003).*

Wahlgren, The Journal of Dermatology, vol. 26: 770-779, 1999 (Year: 1999).*

Fischer et al., A novel extract SB-300 from the stem bark latex of Croton lechleri inhibits CFTR-mediated chloride secretion in human colonic epithelial cells. J Ethnopharmacol. Aug. 2004, published online Jun. 1, 2004; vol. 93, No. 2-3, p. 351-7.

Gutierrez et al., Topical Application of Curcumin Longa 5% Rhizome Ethyl Acetate Extract in Ointment form versus Mupicrocin 2% Ointment in the Treatment of Impetigo and Folliculitis: A Double Blind, Randomized Controlled Trial., J Clin Investigat Dermatol. Feb. 29, 2020; vol. 8, Issue 1, No. 6; p. 1-6.

Zheng et al., Antibacterial and Anti-biofilm Efficacy of Chinese Dragon's Blood Against *Staphylococcus aureus* Isolated From Infected Wounds. Front Microbial. Apr. 6, 2021 vol. 12, No. 672943.

(Continued)

*Primary Examiner* — Jeffrey H Murray
*Assistant Examiner* — Luisalberto Gonzalez
(74) *Attorney, Agent, or Firm* — DLA Piper LLP

(57) ABSTRACT

The present disclosure provides for a method of treating a bacterial colonization or primary or secondary bacterial infection of an underlying skin disorder in a subject via the topical administration of a pharmaceutical composition comprising a therapeutically effective amount of an extract of the *Croton lechleri* tree. Additionally the present disclosure provides for a method of treating a bacterial colonization or primary or secondary bacterial infection of the nasal mucosa in a subject via the nasal administration of a pharmaceutical composition comprising a therapeutically effective amount of an extract of the *Croton lechleri* tree. Also provided are details of studies on the effectiveness of an extract of the *Croton lechleri* tree on bacterial pathogens.

21 Claims, 14 Drawing Sheets

(56) References Cited

OTHER PUBLICATIONS

International Search Report and Written Opinion for PCTUS2021051599 dated Dec. 27, 2021.
Alphyn Biologics Press Release "Alphyn Biologics Reports Encouraging Interim Results of Phase 2a Trial for Atopic Dermatitis With Secondary Bacterial Infection" Jul. 14, 2023, Cision PR Newswire (Exhibit A).
Alphyn Biologics Press Release "Society for Pediatric Dermatology Pster Presentation: Phase 2a Trial of Topical Therapeutic for Mild, Moderate, and Severe Atop Dermatitis" Jul. 14, 2023, Poster Presentation (Exhibit B).
Alphyn Biologics Press Release "Alphyn Biologics Presents New Data from Phase 2a Trial Showing Significant Improvement of Mild-to-Moderate Atopic Dermatitis" Jul. 14, 2023, Cision PR Newswire (Exhibit C).
Vilchez, et al. "Evaluation of the in vitro effect of Croton lechleri Latex "Grade Blood" versus *Staphylococcus aureus* ATCC 25923" Knowledge for Development Jan.-Jun. 2018, 9(1): 129-136 w/English abstract.
He et al. "An Assessment of the Use of Antihistamines in the Management of Atopic Dermatitis" Jan. 6, 2018, The American Academy of Dermatology, 79(1):92-96.
Miller et al. "A unique therapeutic approach to emesis and itch with a proanthocyanidin-rich genonutrient" Jan. 18, 2008, Journal of Translational Medicine, 6(3):1-10.
Miller et al. "Chondroprotective Effects of a Proanthocyanidin Rich Amazonian Genonutrient Reflects Direct Inhibition of Matrix Metalloproteinases and Upregulation of Igf-1 Production by Human Chondrocytes" Aug. 14, 2007, Journal of Inflammation, 4(16):1-10.
Miller et al. "Inhibition of Neurogenic In¯ ammation by the Amazonian Herbal Medicine Sangre de Grado" May 22, 2001, The Society for Investigative Dermatology, 117(3):725-730.
Read et al., "Histamine release by fire ant (*Solenopsis*) venom", 1978, Toxicon, vol. 16, Issue 4, pp. 361-367. (Abstract Only).
Yarbrough et al. "The Effects of Treatment on Itch in Atopic Dermatitis" 2013, Dermatologic therapy, 26(2):1-17.
Cai et al. "Polyphenolic compounds from Croton lechleri" 1991, Phytochemistry, 30(6):2033-2040, doi:10.1016/0031-9422(91)85063-6, XP026630985.
Coppo Erika et al. "Antibacterial Activity of Polyphenols" Jan. 1, 2014, Current Pharmaceutical Biotechnology 15: 380-390.
Database WPI, week 210503, Thomson Scientific, London, GB; AN2015-01758E & CN 104083565A to Yantai Huaxin Biological Technology Co., dated Oct. 8, 2014, abstract.
De Marino et al. "Identification of Minor Secondary Metabolites from the Latex of Croton lechleri (Muell-Arg) and Evaluation of Their Antioxidant Activity" Jun. 1, 2008, Molecules 13(6):1219-1229.
Gonzales et al. "Medicinal Plants from Peru: A Review of Plants as Potential Agents Against Cancer" 2006, Anti-Cancer Agents in Medicinal Chemistry, 6(5):429-444.
Jones "Review of Sangre de Drago (*Croton lechleri*)—A South American Tree Sap in the Treatment of Diarrhea, Inflammation, Insect Bites, Viral Infections, and Wounds: Traditional Uses to Clinical Research" 2003, The Journal of Alternative and Complementary Medicine, 9(6):877-896.
Kono et al. "Antibacterial Activity of Epigallocatechin Gallate Against Methicillin-resistant *Staphylococcus aureus*" 1994, The J. Japanese Association for Infectious Diseases 68(12):1518-1522 (abstract).
Lopes et al. "Dragon's Blood (*Croton lechleri* Mull., Arg.): an Update on the Chemical Composition and Medical Applications of This Natural Plant Extract. A Review" Revista Brasileira de Higiene e Sanidade Animal, BR, 7(2):167-191, doi:10.5935/1981-2965.20130016, ISSN 1981-2965, XP009531125.
Namjoyan et al. "Efficacy of Dragon's blood cream on wound healing: A randomized, double-blind, placebo-controlled clinical trial" 2015, Journal of Traditional and Complementary Medicine, 6(1):37-40.
Pieters et al. "Isolation of a Dihydrobenzofuran Lignan from South American Dragon's Blood (*Croton* spp.) as an Inhibitor of Cell Proliferation" Jun. 1993, J. Natural Products 56(6):899-906.
Pona et al. "Review of future insights of Dragon's Blood in dermatology" 2018, Dermatologic Therapy, 32(2):1-7.
Ramirez et al. "Evaluacion Del Potencial Antibacterial in Vitro De Croton Lechleri Frente a Aislamientos Bacterianos De Pacientes Con Ulceras Cutaneas" Jun. 1, 2013, Nova, 51-63.
World Health Organization "Annex 1—WHO guidelines on good herbal processing practices for herbal medicines" Jan. 1, 2018, Publication data: WHO Technical Report Source info: 1010(52):81-152.
Wollenberg et al., "European guideline (EuroGuiDerm) on atopic eczema—part II: non-systemic treatments and treatment recommendations for special AE patient populations", Journal of the European Academy of Dermatology and Venereology, 2022, vol. 36, pp. 1904-1926.
Yosipovitch et al., "Itch: From mechanism to (novel) therapeutic approaches", J. Allergy Clin. Immunol., 2018, vol. 142, pp. 1375-1390.
Gupta et al. "Dragon' Blood: botany, chemistry and therapeutic uses" Oct. 22, 2007, J. Ethnopharmacology 115:361-380.
De-Xing et al. "Progress of Green Tea Antibacterial Activity and Mechanism Againt Methiillin-resistant *Staphylococcus aureus*" Sep. 30, 2008, (Chinese) J. New Drugs Clinical Remedies 27(9):697-701.
Chun-Lin et al. "Research progress in antibacterial activity of polyphenol compounds" Dec. 31, 2012, Science and Technology of Food Industry 33(177):405-408.
International Search Report and Written Opinion for PCT/US2022/017922 dated, with mail date. (May 18, 2022).

* cited by examiner dimethylcedrusin

TOPICAL *CROTON LECHLERI* COMPOSITIONS AND THEIR USE IN THE TREATMENT OF A BACTERIAL COLONIZATION OR PRIMARY OR SECONDARY BACTERIAL INFECTION OF AN UNDERLYING SKIN DISORDER

CROSS-REFERENCE TO RELATED APPLICATIONS

This application claims the benefit of U.S. Provisional Application No. 63/081,657 filed Sep. 22, 2020 and U.S. Provisional Application No. 63/081,665 filed Sep. 22, 2020. The disclosures of each of these applications are incorporated herein by reference.

SUMMARY

The present invention is generally related to the treatment of a bacterial colonization or primary or secondary bacterial infection of an underlying skin disorder, via the topical or nasal administration of a pharmaceutical compositions comprising a therapeutically effective amount of latex of *Croton lechleri*, preferably filtered latex of *Croton lechleri*, preferably filtered latex of *Croton lechleri* Müll. Arg., wherein the therapeutically effective amount contains at least the concentration of components of the reference standard. The concentration of components and performance standards of latex of *Croton lechleri*, preferably the concentration of components and performance standards of filtered latex of *Croton lechleri*, preferably the concentration of components and performance standards of filtered latex of *Croton lechleri* Müll. Arg of the reference standard are found in Tables 1a-e.

DEFINITIONS

Figure 1:
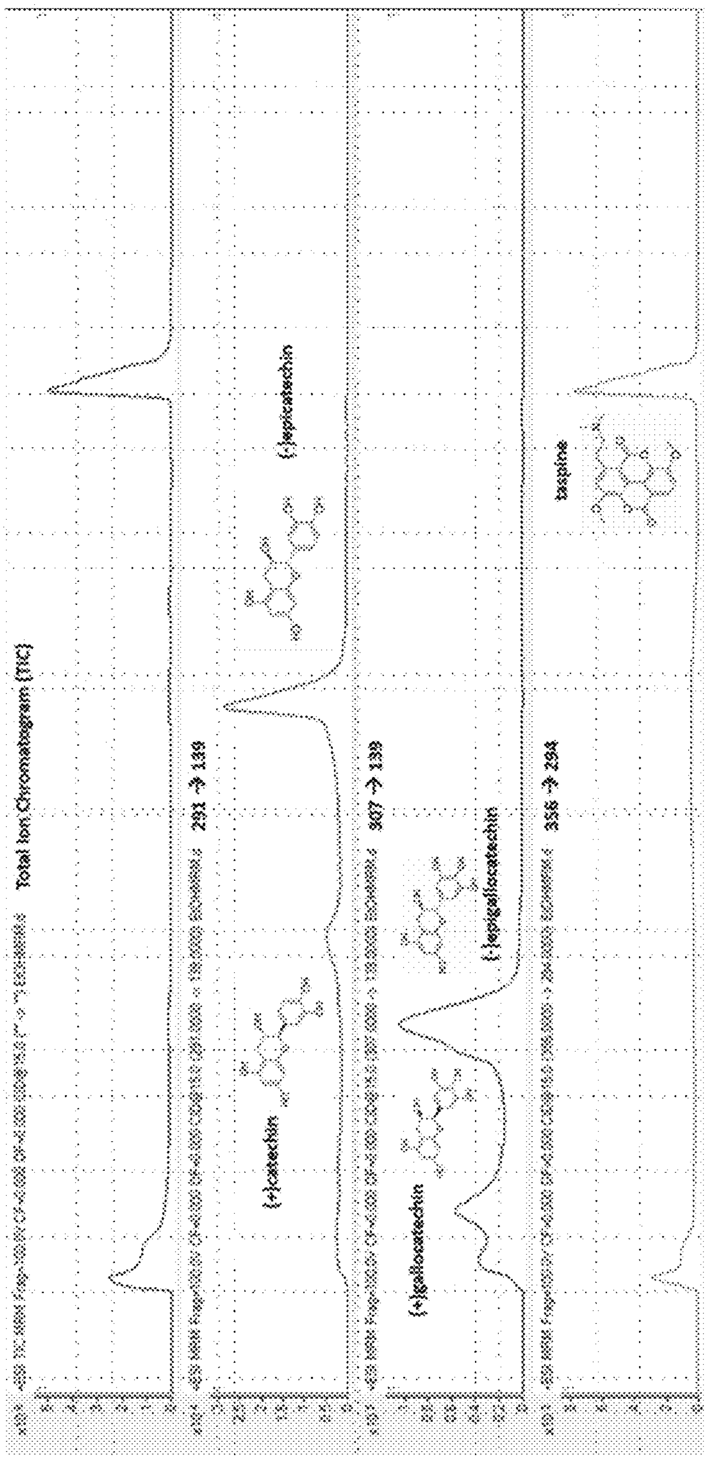
FIG. 1 depicts a representative Total Ion Chromatogram as well as additional Multiple Reaction Monitoring spectra that identify the marker compounds in an AB-101 composition.

Before the present compositions and methods are described, it is to be understood that this invention is not limited to the particular processes, compositions, or methodologies described, as these may vary. It is also to be understood that the terminology used in the description is for the purpose of describing the particular versions or embodiments only and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

As used herein, the terms below have the meanings indicated.

It must also be noted that as used herein and in the appended claims, the singular forms "a," "an," and "the" include plural reference unless the context clearly dictates otherwise.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean plus or minus 10% of the numerical value of the number with which it is being used. Therefore, about 50% means in the range of 45%-55%.

As used herein, the term "AB-101" maybe used interchangeably with latex of *Croton lechleri*, preferably filtered latex of *Croton lechleri*, preferably filtered latex of *Croton lechleri* Müll. Arg. and botanical raw material. The latex is excreted material from the wounded trunk of *Croton lechleri*, preferably of *Croton lechleri* Müll. Arg. In all such instances the latex is the whole latex. In all such instances, the latex is unfractionated.

"Administering" when used in conjunction with a therapeutic, such as AB-101, means to administer a therapeutic directly into or onto a target tissue or to administer a therapeutic to a patient whereby the therapeutic positively impacts the tissue to which it is targeted. Thus, as used herein, the term "administering", when used in conjunction with a composition of embodiments herein, can include, but is not limited to, providing the composition into or onto the target tissue; providing the composition to a patient by, e.g., topical application whereby the therapeutic reaches the target tissue. "Administering" a composition may be accomplished topically or in combination with other known techniques.

As used herein the term "cellulitis/erysipelas" is defined as a diffuse bacterial skin infection characterized by spreading areas of redness, edema, and/or induration.

The transitional term "comprising," which is synonymous with "including," "containing," or "characterized by," is inclusive or open-ended and does not exclude additional, unrecited elements or method steps.

In embodiments or claims where the term "comprising" is used as the transition phrase, such embodiments can also be envisioned with replacement of the term "comprising" with the terms "consisting of" or "consisting essentially of."

As used herein, the term "consists of" or "consisting of" means that the pharmaceutical composition, composition or the method includes only the elements, steps, or ingredients specifically recited in the particular claimed embodiment or claim.

As used herein, the term "consisting essentially of" or "consists essentially of" means that the pharmaceutical composition, or the method includes only the elements, steps or ingredients specifically recited in the particular claimed embodiment or claim and may optionally include additional elements, steps or ingredients that do not materially affect the basic and novel characteristics of the particular embodiment or claim. For example, the only active ingredient(s) in the composition or method that treats the specified condition (e.g., nutrient depletion) is the specifically recited therapeutic(s) in the particular embodiment or claim.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner In either case, the treatment regimen will provide beneficial effects of the drug combination in treating the conditions or disorders described herein.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The terms "excipient" and "pharmaceutically acceptable excipient" as used herein are intended to be generally synonymous, and is used interchangeably with, the terms "carrier," "pharmaceutically acceptable carrier," "diluent," "pharmaceutically acceptable diluent."

As used herein, the term "extract" refers to the liquid that runs between the bark and the wood portions of the tree, which is and remains unfractionated.

As used herein the term "major cutaneous abscess" is defined as a bacterial infection characterized by a collection of pus within the dermis or deeper that is accompanied by redness, edema, and/or induration.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

As used herein, the term "pharmaceutically acceptable salt" refers to a salt prepared from a base or acid which is acceptable for administration to a patient, such as a mammal. The term "pharmaceutically acceptable salts" embraces salts commonly used to form alkali metal salts and to form addition salts of free acids or free bases. The nature of the salt is not critical, provided that it is pharmaceutically-acceptable. Such salts can be derived from pharmaceutically-acceptable inorganic or organic bases and from pharmaceutically-acceptable inorganic or organic acids.

As used in each of the embodiments here in, sap may be include among others sap, latex, resin, extract, or any combination of the foregoing.

As used herein, the term "therapeutic" or "therapeutic agent" or "pharmaceutically active agent" means an agent utilized to treat, combat, ameliorate, prevent or improve an unwanted condition or disease of a patient.

In part, embodiments of the present invention are directed to the treatment of a bacterial colonization or primary or secondary bacterial infection of an underlying skin disorder. In some embodiments of the present invention, this infection or colonization can be a bacterial colonization or primary or secondary bacterial infection of the nasal mucosa. In some embodiments of the present invention, the underlying skin disorder includes, but is not limited to, impetigo, atopic dermatitis, eczema, epidermolysis bullosa, psoriasis, and wounds (including, but not limited to chronic wounds, superficial wounds, and abrasions). In some embodiments of the present invention, the infection or colonization includes, but is not limited to *Streptococcus pyogenes* infection or colonization, *Staphylococcus aureus* infection or colonization, methicillin-resistant *Staphylococcus aureus* (MRSA) infection or colonization, Mupirocin-resistant MRSA, *Enterococcus faecalis* infection or colonization, Gram-positive bacteria infection or colonization, Gram-negative bacteria infection or colonization, cellulitis/erysipelas, wound infection or colonization, burn infection or colonization, major cutaneous abscesses, impetigo, Mupirocin-resistant impetigo, Vancomycin resistant bacteria infection or colonization, Mupirocin resistant bacteria infection or colonization, *Clostridium difficile* infection or colonization, drug-resistant *Neisseria gonorrhoeae* infection or colonization, *Streptococcus pneumoniae* infection or colonization, drug-resistant *Streptococcus pneumoniae* infection or colonization, drug-resistant *Klebsiella pneumoniae* infection or colonization, drug-resistant Malaria infection or colonization, Multi-drug resistant (MDR) infection or colonization, Extensively drug-resistant (XDR) Tuberculosis infection or colonization, *Escherichia coli* (*E. coli*) infection or colonization, Shiga toxin-producing *Escherichia coli* (*E. coli*) infection or colonization, infections or colonizations caused by bacteria possessing Enzyme NDM-1 (New Delhi Metallo-beta-lactamase-1), *Clostridium difficile* infection or colonization, *Enterococcus* infection or colonization, *Mycobacterium tuberculosis* infection or colonization, *Mycoplasma genitalium* infection or colonization, *Streptococcus* infection or colonization, *Campylobacter* infection or colonization, *Neisseria gonorrhoeae* infection or colonization, Gamma proteobacteria infection or colonization, Enterobacteriaceae infection or colonization, Carbapenem-Resistant Enterobacteriaceae, infection or colonization, *Klebsiella pneumoniae* infection or colonization, *Salmonella* infection or colonization, *E. coli* infection or colonization, Pseudomonadales infection or colonization, *Acinetobacter* infection or colonization, *Pseudomonas aeruginosa* infection or colonization, MDR *Pseudomonas aeruginosa* infection or colonization, and Coagulase-negative *Staphylococcus* infection or colonization.

The term "therapeutically acceptable" refers to those compositions which are suitable for use in contact with the tissues of patients without undue toxicity, irritation, and allergic response, are commensurate with a reasonable benefit/risk ratio, and are effective for their intended use.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid.

The phrase "therapeutically effective" is intended to qualify the amount of active ingredients used in the treatment of a disease or disorder or on the effecting of a clinical endpoint.

A "therapeutically effective amount" or "effective amount" of a composition is a predetermined amount calculated to achieve the desired effect, i.e., to, inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages per application will normally fall within the range of from 0.001 to 10 mg/kg, more usually in the range of from 0.01 to 1 mg/kg. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of the composition of this invention is typically an amount such that when it is administered in a physiologically tolerable excipient composition, it is sufficient to achieve an effective systemic concentration or local concentration in the tissue.

The terms "treat," "treated," "treating", or "treatment" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "topical" includes administering to any skin or mucosal surface or being suitable for such administration. In some embodiments, "topical" may be the skin surface. Skin surface includes any part of the body, including but not limited to face, hands, legs, neck, abdominal area, eyes, nose, and chest. Mucosal surface includes, without limitation, mucosa of the mouth or oral mucosa, lips, tongue, nasal, buccal mucosa, palate, gingiva, nasopharynx, respiratory epithelium, conjunctiva, vagina, cervix, and urethral mucosa.

As used herein, the term "wound" is defined as an injury to living tissue caused by a cut, blow, or other impact, typically one in which the skin is cut or broken.

As used herein the term "wound infection" is defined as a bacterial infection characterized by purulent drainage from a wound with surrounding redness, edema, pain, tenderness and/or induration.

Also provided are embodiments wherein any embodiment herein may be combined with any one or more of the other embodiments, unless otherwise stated and provided the combination is not mutually exclusive.

SUMMARY

The chemical defenses of plants include complex mixtures of organic compounds and typically do not involve individual substances; these compounds appear in different concentrations (majority or minority) within various products derived from natural species. The biological activities of these products can be found to originate from their ability to interact among themselves and other substances through synergistic, additive, antagonistic effects—and can be optimized through the modification of the pharmacokinetics and/or pharmacodynamics of the component substances. The biological effects may occur from the interaction with all the organic compounds or by the interaction among certain components, which may present themselves as majority or minority. Accordingly, when described herein, AB101 consists of the whole latex obtained from the *Croton lechleri* tree—it is unfractionated—but is selected based upon the presence of select components that meet the reference standard as described herein.

In natural product research, the major compound's role and mechanism in its associated biological activity is commonly investigated. Thus, in the scientific literature, there are innumerous published studies where the major components have been found to be responsible for these activities. However, this disregards the possible interactions among the totality of compounds that may be present at lower concentrations in natural products. A study carried out with the essential oil *Thymus vulgaris* and its major constituent, thymol identified that the effect of the constituents of the oil was not phytotoxic to lettuce seeds, whereas the isolated action of thymol caused significant inhibitory effects on seed germination, raising the possibility of a partial inhibition of thymol activity by other components of the oil. Demonstrating the importance of considering the interactions among all components of the product.

For example, evaluation of the activity of the sap of *Dracaena cochinchinensis* and three active constituents regarding the analgesic activity from the inhibition of currents on the TRPV1 channel, induced by capsaicin. As a result, the authors found that the combination of the three active components of the sap is responsible for the analgesic activity of the species in question, where these components act synergistically, as the compounds found in greater concentration were not directly responsible for the biological activity found.

Another consideration regarding interactions among the active components of a natural product is the ability to alter the pharmacokinetics of the components when compared with the administration of these molecules in isolation. This can be achieved by modifying the absorption, distribution, metabolism and elimination profiles. A study reported the pharmacokinetic profile of chlorogenic acid and coryloin alone in comparison with the product formed by the hydroalcoholic extract of *Pharbitis nil* and *Corydalis tuber*, DA-9701, which contains the two components in equivalent concentrations. Results showed a significant increase in the AUC of coryloin when DA-9701 was administered compared with the two compounds in isolation, both orally. This increase in AUC can be explained by decreased hepatic and/or gastrointestinal first-pass metabolism compared with pure coryloin. In addition, there may be inhibition of corticosteroid presystemic metabolism by other components of DA-9701.

Another example is the complexity of metabolic pathways and the complexity of essential oils, extracts and herbal products may be directly related to the recorded biological effect. In a study with essential oil of *Eucalyptus tereticornis* and its major constituents, it was observed that all three major constituents reinforce the constricting effect of acetylcholine in the trachea of rats, however with a stimulus of potassium, the essential oil presents a relaxing effect, may be due to the inhibition of acetylcholinesterase activity.

*Croton lechleri* (a member of the family Euphorbiaceae, commonly called the spurge family) has approximately 1,300 species of plants that are either herbaceous (plants that have no persistent woody stem above ground), shrub (a woody plant which is smaller than a tree and has several main stems arising at or near the ground), tree (a perennial plant with an elongated stem, or trunk, supporting branches and leaves in most species), or liana (any of various long-stemmed, woody vines that are rooted in the soil at ground level and use trees, as well as other means of vertical support, to climb up to the canopy to get access to well-lit areas of the forest) forms. The *Croton* genus is a diverse and complex group of flowering plants ranging from herbs and shrubs to trees. The *Croton* genus is widely distributed in tropical and subtropical regions around the world.

Dragon's blood refers to a bright red resin that is obtained from different species of a number of distinct plant genus: *Croton, Dracaena, Daemonorops, Calamus rotang* and *Pterocarpus*. The red resin has been in continuous use since ancient times as varnish, medicine, incense, and dye. The name dragon's blood is used to refer to all of the above plant genus, often without any distinction as to the genus or species it is coming from. Those with the same genus will be similar in any therapeutic or nutritional value, with factors such as local soil, local rainfall, local humidity, local sunlight, local fauna and the like imparting variability and inconsistency. However, the difference between the red resin coming from *Croton* versus *Daemonorops* (a genus of rattan palms in the family Arecaceae found primarily in the tropics and subtropics of southeastern Asia with a few species extending into southern China and the Himalayas) will be significant. The *Croton* and *Daemonorops* genus originate from opposite sides of the world so their components are different and therefore specificity of source plant is important to deliver the desired medicinal benefits or avoid undesirable toxic results. For example milky white latex that is often toxic or at least irritating to the skin is common to the members of the spurge or Euphorbiaceae family Therefore selecting the specific genus, species, and local geographical area of the spurge or Euphorbiaceae family is essential to having the possibilty for the latex to have specific and repetitive medicinal properties.

A handful of *Croton* species found in the South America rainforest (in countries of Bolivia, Brazil, Colombia, Ecuador and Peru) Central America and Mexico produce the red latex, commonly known as dragon's blood, that has medicinal properties. The dragon's blood trees grown in these areas include *Croton lechleri, Croton draco, Croton palanostigma, Croton sordidus, Croton urucurana*, and *Croton xalapenesis.*

In certain embodiments, the specific dragon's blood tree of the present application is *Croton lechleri* Müll. Arg. of the Family: Euphorbiaceae. Dragon's blood is also referred to as Sangre de drago (Peru), Sangre de grado (Ecuador).

While the desired medicinal properties could be found by extracting the compositions from either the leaves or bark, in preferred embodiments, it is the deep red latex of *Croton lechleri*, preferably filtered latex of *Croton lechleri*, preferably filtered latex of *Croton lechleri* Müll. Arg, wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard, that is also referred to as latex, that is utilized. According to Langenheim (2003) resin "is a lipid-soluble mixture of volatile and non-volatile terpenoid and/or phenolic secondary compounds that are usually secreted in specialized structures located either internally or on the surface of the plant and are of potential significance in ecological interactions". By contrast, latex, is a mixture of terpenoids, phenolic compounds, acids, carbohydrates, etc. having a protective role (Lewisohn 1991) and produced in special cells called laticifers (Fahn 1979). Chemical characterization of dragon's blood is species specific and has been undertaken by many authors. For example, it is possible to distinguish between dragon's blood from some individual species used in works of art, since it has been sold as a colorant for many centuries (Baumer and Dietemann 2010). Dragon's blood of *Croton* spp. is usually referred to as latex due to the fact that it is secreted and stored by laticifers, and its major constituents are polymeric anthocyanidins, which co-occur with many minor constituents, including diterpenes and simple phenols (Salatino et al. 2007). Dragon's blood secreted by stems of *Pterocarpus officinalis* is also called latex (Weaver 1997; Guerrero and Guzman 2004); however, information about the chemical composition of the exudate and its ecological function is poorly known. Dragon's blood derived from species of *Dracaena* and *Daemonorops* is a phenolic resin (Langenheim 2003), with well-recognized chemical content (e.g. Gonzalez et al. 2000; Shen et al. 2007; Sousa et al. 2008). Sometimes, dragon's blood is referred to as latex (e.g. Philipson 2001). However, this could prove to be a source of confusion, since plants produce other exudates referred to by that name, such as xylem latex and phloem latex, which are entirely different in terms of their location, chemical composition and function. The resin is obtained through tapping the tree or other common draining methods. Draining the tree latex has the additional benefit of not having to use complex and costly extraction technology to obtain the desired composition from either the leaves or bark. The latex of *Croton lechleri* Müll. Arg. of the present application is then filtered in a 30 micron filter to remove plant debris and thick, resinous material. Chemical characterization of dragon's blood is local geography specific and has not been undertaken by prior authors.

Medicinal and toxic properties of various species of the *Croton* genus have been ascribed to a wide variety of chemical compounds, such as terpenoids and steroids, alkaloids, and phenolic compounds, the latter including predominantly flavonoids, lignans, and proanthocyanidins. Some embodiments of the present application utilize the whole latex, thereby leveraging the "organic" synergy of all the latex components as intended by nature. The molecular classes found in latex of *Croton lechleri* Müll. Arg. of the present application which provide the desired medicinal benefits of *Croton lechleri* Müll. Arg. are: Alkaloids, Diterpenes, Lignins, Phenols, Phytosterols, Proanthocyanidins, Sterols and Tannins.

For a pharmaceutical composition to be effective in treating a bacterial colonization or primary or secondary bacterial infection of an underlying skin disorder, this composition needs to have properties that including but not limited to: antibacterial performance to fight infection. In addition, the composition needs to have a safety profile for use in topical applications where the composition has low systemic blood absorption (i.e. passage into the blood stream) and where the composition that is absorbed has a low partition coefficient as measured by Log P. The Log P represents the concentration of solute in the organic and aqueous partition. A low Log P means a higher partition or concentration in the aqueous solute. This is desirable from a safety standpoint. A higher Log P indicates the composition is more likely to absorbed and retained in the body via organs and tissues, while lower Log P indicates higher safety via the composition would be natural eliminated, not absorbed or retained that could lead to build up of toxic compounds.

AB-101 uses the unique composition of the entire latex of the *Croton lechleri* Mull. Arg. The novelty of this invention is identifying the pharmaceutical AB-101 composition that has all the performance properties listed above to treat a bacterial colonization or primary or secondary bacterial infection of an underlying skin disorder, and promote healing with the appropriate safety profile. This represents a complex multivariant solution that optimizes multiple performance properties where the solution is not obvious to one familiar with the art.

In the embodiments disclosed herein, the latex of *Croton lechleri*, preferably filtered latex of *Croton lechleri*, preferably filtered latex of *Croton lechleri* Müll. Arg, that is utilized is not fractionated, but does contain at least the concentration of certain components and performance standards of the reference standard as set forth in Tables 1a-e.

AB-101 is a novel first-in-class of a new class of broad spectrum topical antibiotics called Multi-Target Therapeutics (MTT). The AB-101 platform utilizes the latex from the *Croton lechleri* Müll. Arg tree that is native and ubiquitous to the Amazonian forest. The extract and therefore AB-101 Botanical Drug Substance (BDS) has multiple bioactive compounds.

AB-101 has unique antibiotic properties as demonstrated via bioassay testing demonstrating AB-101 is effective against the gram-positive pathogens *Staphylococcus aureus* (*S. aureus*), methicillin-resistant *Staphylococcus aureus* (MRSA), *Streptococcus pyogenes* (*S. pyogenes*) and the gram-negative pathogen *Pseudomonas aeruginosa* (*P. aeruginosa*). The fact that AB-101 has efficacy against both gram-positive and gram-negative pathogens is unique when compared to the typical specifically synthetically derived active drug compound, and this benefit is directly attributed to AB-101 MTT properties.

MTT affords AB-101 a broad, multi-mechanism mode of action, which, in turn, strongly reduces the potential for development of bacterial resistance and provides broad-spectrum activity against many different bacteria. The alarming need for new, effective treatments, combined with the increasing resistance to current standard of care treatment options creates a significant need for an AB-101 topical antibiotic.

Skin and Soft Tissue Infections (SSTIs) cover a variety of topical infections and skin conditions that are stressed by bacterial pathogens. In addition, there are significant topical indications that have chronic infections, including wounds that are also stressed by bacterial pathogens.

Skin disorders vary greatly in symptoms and severity. AB-101 is a potent antibiotic that is designed to treat skin conditions affected *S. aureus*, MRSA and MRSA resistant to mupirocin, *S. pyogenes* and *P. aeruginosa.*

Further there is a global imperative to address the increasing crisis of Multi-Drug Resistance (MDR) infections, particularly MRSA skin infections. Topical antibiotics continue to be an important treatment tool. Lack of new, effective topical antibiotics has created a need gap in treatment, global health security and preparedness to treat infectious diseases. AB-101 as topical treatment provides a novel solution to address this treatment gap and advances superior solutions to help the welfare of the world population.

Skin conditions that AB-101 can treat are related to both acute and chronic skin disorders. AB-101 primary treatment is to treat the bacteria causing the infection. Secondary benefits include the healing benefits associated with antiinflammation, skin redness, bumps, blisters, antioxidant and soothing properties, fibroblast stimulation and pruritus or antiitching properties associated with AB-101. In many cases the primary bacteria associated with the SSTI can be the source for these secondary conditions. By AB-101 attacking and addressing the source problem, relief of the secondary symptom can be addressed as well.

Some of the infected or colonized SSTI skin conditions that AB-101 can treat are associated with both acute and chronic conditions. These skin treatment indications include and are not limited to include impetigo, atopic dermatitis/eczema, epidermolysis bullosa, psoriasis, skin colonized by *S. aureus* and MRSA and wounds inclusive of chronic, superficial and abrasions.

Within this skin infection, MRSA has increased and has become more prevalent. As described in MedlinePlus, US National Library of Medicine (Habif T P. Bacterial infections. In: Habif T P, ed. *Clinical Dermatology: A Color Guide to Diagnosis and Therapy.* 6th ed. Philadelphia, PA: Elsevier; 2016:chap 9.; Kliegman R M, Stanton B F, St. Geme J W, Schor N F. Cutaneous bacterial infections. In: Kliegman R M, Stanton B F, St. Geme J W, Schor N F, eds. *Nelson Textbook of Pediatrics.* 20th ed. Philadelphia, PA: Elsevier; 2016:chap 665; and Pasternack M S, Swartz M N. Cellulitis, necrotizing fasciitis, and subcutaneous tissue infections. In: Bennett J E, Dolin R, Blaser M J, eds.

*Mandell, Douglas, and Bennett's Principles and Practice of Infectious Diseases, Updated Edition.* 8th ed. Philadelphia, PA: Elsevier Saunders; 2015:chap 95) "Impetigo is caused by *streptococcus* (strep) or *staphylococcus* (staph) bacteria. Methicillin-resistant staph *aureus* (MRSA) is becoming a common cause." This is becoming common knowledge as seen within Dr. Pai private practice website Kids+ pediatrics (kidspluspgh.com/doctors-notes/impetigo-mrsa/) where he states: "Impetigo is a superficial skin infection, most commonly caused by the bacteria *Streptococcus* (Strep for short) and *Staphylococcus Aureus* (Staph for short). This particular strain of Staph is called Methicillin Sensitive Staph *Aureus* (MSSA). The drug Methicillin has been used to treat infections caused by Staph for several decades. But in the past ten years or so, this MSSA has outsmarted Methicillin and figured out a way, by genetic modification, to resist it. MSSA has, in many cases, become MRSA. No longer can we rely on Methicillin—or, for that matter, several other antibiotics normally used to treat infections caused by MRSA."

The novel antibiotic, AB-101, has been shown to be effective against *Staphylococcus aureus* (*S. aureus*), methicillin-resistant *Staphylococcus aureus* (MRSA), *Streptococcus pyogenes* (*S. pyogenes*). This makes AB-101 a very effective treatment for the cure of impetigo.

The National Eczema Association, describes eczema also sometimes referred to as atopic dermatitis (AD), "as the name for a group of conditions that cause the skin to become itchy, inflamed, or have a rash-like appearance. There are seven types of eczema: atopic dermatitis, contact dermatitis, dyshidrotic eczema, nummular eczema, seborrheic dermatitis, and stasis dermatitis. The eczema condition can be presented in both infected and non-infected and the pathogens can be colonized on the skin. Eczema is very common. Eczema can begin during childhood, adolescence, or adulthood and it can range from mild to severe."

"Eczema is not contagious. When an irritant or an allergen from outside or inside the body "switches on" the immune system, it produces inflammation. It is this inflammation that causes the symptoms common to most types of eczema. Atopic dermatitis is characterized as dry, itchy skin (pruritus) that often appears with a red rash and can be inflamed, discolored or have areas of swelling. These are the most common and chronic type of eczema. A person may have all of these symptoms of eczema or only just a few." Due to problems with the skin barrier and an increase of bacteria on the skin, people with eczema are prone to skin infections from both bacteria and viruses, especially staph and herpes.

People with atopic dermatitis are more likely than the general population to have "colonized" *Staphylococcus aureus* (also called "staph") bacteria, leaving them more prone to staph infections. Common types of staph infections include: Furuncles, also known as boils, start in the hair follicle and are caused by both bacteria and fungi. Furuncles, furunculosis folliculitis are usually red, warm and tender to the touch. And cellulitis, which is a deep infection in the skin and is usually very painful and tender to the touch. In addition to redness, other cellulitis symptoms include swollen skin that is warm or hot to the touch. In severe cases, people with cellulitis develop a fever and elevated white blood cell count and may need to be hospitalized.

As has been experience with drug resistance disease, when patient is infected with *S. aureus* there is a high likelihood that it will also be infected with MRSA. This is indeed the case as published by Peck Ong. Peck details Methicillin-resistant *Staphylococcus aureus* (MRSA) is a frequent cause of recurrent skin and soft tissue infections. For patients with atopic dermatitis, recurrent skin infections with MRSA often lead to eczema exacerbation. There currently is no standard practice in the prevention of recurrent MRSA soft tissue infections in the general and the atopic dermatitis populations. (Peck Y Ong, Recurrent MRSA skin infections in atopic dermatitis, J Allergy Clin Immunol Pract. 2014 July-August; 2(4):396-9. doi: 10.1016/j.jaip.2014.04.007. Epub 2014).

Further, atopic dermatitis (AD) is a highly pruritic skin condition. Patients with AD are predisposed to colonization by *Staphylococcus aureus* due to deficiencies in the mechanical and immunological functions of the skin barrier. The findings reported by Leszek Blicharz shows *S. aureus* skin colonization may be one of the factors aggravating itch in AD. It may be hypothesized that restoring the natural composition of the skin microbiome may reduce pruritus intensity. (Leszek Blicharz, Paulina Usarek, Grażyna Młynarczyk, Krzysztof Skowroński, Lidia Rudnicka, Zbigniew Samochocki, Is itch intensity in atopic dermatitis associated with skin colonization by *Staphylococcus aureus*?, Indian Journal of Dermatology, 2020, Vol 65, Issue 1, Pages 17-21).

AB-101 novel first-in-class of a new class of broad spectrum topical antibiotics with MTT is an effective treatment for eczema including all forms of atopic dermatitis to those skilled in the art. AB-101 is effective against *S. aureus* and MRSA. *S. aureus* and MRSA has been associated with eczema, both infected and non-infected and many of the symptoms specifically inflammation, redness and pruritic skin conditions.

Epidermolysis bullosa (EB) as described by the NIH is a group of genetic skin diseases that cause the skin to blister and erode very easily. In people with EB, blisters form in response to minor injuries or friction, such as rubbing or scratching. There are four main types of EB, which are classified based on the depth, or level, of blister formation: Epidermolysis bullosa simplex, Dystrophic epidermolysis bullosa, Junctional epidermolysis bullosa and Kindler Syndrome.

When necessary, treatment with oral and topical medications is commonly prescribed by physicians to assist healing or prevent complications. Researchers at Columbia University reported that skin colonization by bacteria resistant to mupirocin is frequent among patients with epidermolysis bullosa. During their investigation of EB patients the research team identified 11 different microorganisms, the most common being methicillin-susceptible and methicillin-resistant (MRSA) *Staphylococcus aureus, Streptococcus species*, and *Pseudomonas aeruginosa*. At the start of the study about 30% of the patients had wound colonization by *S. aureus* resistant to mupirocin, a frequency that increased to 65% during the two-year course of the study. The study stated, "Given the widespread resistance to many systemic and topical antibiotic agents in individuals with EB, surveillance cultures with routine testing for mupirocin resistance may help guide antibiotic stewardship and counseling." (Hannah M. Singer et. al., Wound culture isolated antibiograms and caregiver-reported skin care practices in children with epidermolysis bullosa, Volume 35, Issue 1, Pages 92-96, Pediatric Dermatology).

The primary aim of treatment of EB is to protect the skin and stop blister formation, promote healing, and prevent complications. AB-101 has unique benefits to treating EB. They include the ability to treat many of the common bacteria infecting EB patients which include *S. aureus*, MRSA and MRSA resistant to mupirocin, *S. pyogenes* and *P. aeruginosa*. Since AB-101 is unique in its ability to fight both gram-positive and gram-negative pathogen, which infects EB patients which is unusual for antibiotics, makes AB-101 a preferred treatment option. Further, the Columbia study highlighted the need to address multi-drug resistance. AB-101 is an appropriate alternative to mupirocin to break the cycle of MDR and address the needs for alternative topical treatments for EB.

Psoriasis is a skin disease that causes red, itchy scaly patches, most commonly on the knees, elbows, trunk and scalp. As defined by the Mayo Clinic, psoriasis is a common, long-term (chronic) disease with no cure. Most types of psoriasis go through cycles, flaring for a few weeks or months, then subsiding for a time or even going into remission. Psoriasis signs and symptoms can vary from person to person. Common signs and symptoms include: 1. Red patches of skin covered with thick, silvery scales, 2. small scaling spots (commonly seen in children), 3. dry, cracked skin that may bleed or itch, 4. Itching, burning or soreness, 5. thickened, pitted or ridged nails and 6. swollen and stiff joints. Psoriasis patches can range from a few spots of dandruff-like scaling to major eruptions that cover large areas. The most commonly affected areas are the lower back, elbows, knees, legs, soles of the feet, scalp, face and palms.

As reported by S. Lafi et. al. secondary bacterial invaders complicate psoriasis lesions. Such infections can progress rapidly and can be seriously life-threatening. Hassan studied the current prevalence of the secondary bacterial infections in psoriasis and also highlighted the emerging trend associated with antibacterial resistance. (Lafi, S., Hasan, A., Al-Alowssi, M. (2010). Secondary Bacterial Infections Complicating Psoriasis. Egyptian Academic Journal of Biological Sciences, G. Microbiology, 2(2), 37-42).

In another study conducted by Eva Marcus, it was shown that nearly half of the patients examined had colonization of the psoriasis plaques with pathogenic bacteria. Examinations of the bacterial flora in psoriasis concentrated on the proof of *Staphylococcus aureus* and found a prevalence of up to 64% in lesional skin of patients with plaque psoriasis. Corresponding to this, *Staphylococcus aureus* has also been found as the most prevalent bacterium in patients with superinfected pustular psoriasis. In this study 31% of the bacteria were gram-positive and 9% were gram-negative. (Marcus, E., Demmler, D., Rudolph, A., & Fischer, M. (2011). Bacterial colonization of psoriasis plaques. Is it relevant? Dermatology reports, 3(2)).

AB-101 is an important topical treatment to reduce and cure the symptoms of psoriasis. *Staphylococcus aureus* is the most common pathogen isolated in psoriasis lesions which AB-101 has been shown to be extremely effective. Further, with the rise of multi-drug resistance, especially with *S. aureus* the presence of MRSA will also be on the rise. Having gram-negative efficacy can also contribute to a positive role for AB-101. Having a new MDR topical treatment for secondary bacterial invaders to prevent the occurrence of a deadly systemic infection present AB-101 as an excellent antibiotic treatment for psoriasis.

Pathogen colonization is an important skin condition to be addressed as detailed by Sunhyo Ryu (S. Ryu, P. I. Song, C. H. Seo, H. Cheong and Y. Park, Colonization and Infection of the Skin by *S. aureus*—Immune System Evasion and the Response to Cationic Antimicrobial Peptides, Int. J. Mol. Sci. 2014, 15, 8753-8772). Colonizing pathogens primarily relate to *S. aureus* and MRSA and AB-101 is an effective and novel treatment for these pathogens.

Ryu details the causes, mechanism and risks associated with colonized *S. aureus* and MRSA. Specifically, *S. aureus* is a widespread cutaneous pathogen responsible for the great majority of bacterial skin infections in humans. The incidence of skin infections by *S. aureus* reflects in part the competition between host cutaneous immune defenses and *S. aureus* virulence factors. *S. aureus* can live as a commensal organism on the skin and in the nose and throat. Approximately 30% of healthy people are asymptomatically colonized by *S. aureus*, which permanently colonizes the anterior nares in 10%-20% of the population and intermittently colonizes 30%-50%; the rest of the population never becomes colonized. Importantly, this colonization is a known risk factor for infection, and *S. aureus* causes a range of infections, from minor skin infections to abscesses, endocarditis and sepsis, and is a leading cause of nosocomial infections, as colonized healthcare workers can transmit the pathogen to immunosuppressed patients. In addition, several cases of community-acquired methicillin-resistant *S. aureus* (CA-MRSA) infections have been recently reported. Notably, these reports describe severe and even lethal infections by highly virulent strains of *S. aureus* in immunocompetent individuals.

MRSA infections are caused by strains of *S. aureus* that have become resistant to the antibiotics commonly used to treat ordinary infections. Most MRSA infections occur in people who have been in hospitals or other health care settings, such as nursing homes and dialysis centers. When it occurs in these settings, it is known as health care-associated MRSA (HA-MRSA). HA-MRSA infections are typically associated with invasive procedures or devices, such as surgeries, intravenous tubing or artificial joints. However, another type of MRSA infection occurs in the wider community, among otherwise healthy individuals. This form, community-associated MRSA (CA-MRSA) is spread by skin-to-skin contact. It often begins as a painful skin boil and generally causes skin and soft tissue infections, but it is also capable of causing invasive disease such as endocarditis, necrotizing pneumonia and sepsis HA-MRSA, by contrast, is considered a nosocomial pathogen typically associated with invasive disease, such as bloodstream infections, pneumonia, surgical site infections and urinary tract infections.

AB-101 with its MTT is a novel and critical antibiotic to address colonizing *S. aureus* and MRSA as it is associated with a disorder caused by *S. aureus* and MRSA nasal or ear passage, as a wash prior to surgery to prevent SSTI or the occurrence of sepsis in any other applications for those familiar with the art associated with conditions that can prevent the spread and elimination of colonizing *S. aureus* and MRSA.

AB-101 is an effective treatment for wounds including superficial cut/scraps, abrasions and chronic infected conditions. Chronic infection and wounds include but not limited to diabetic ulcers, arterial ulcers, venous ulcers, mixed arterial and venous ulcers and decubitus ulcers. Those familiar of these infections and wounds and skilled in the art are well aware that they are infected by gram-positive pathogens associated with *Staphylococcus aureus* (*S. aureus*), methicillin-resistant *Staphylococcus aureus* (MRSA), *Streptococcus pyogenes* (*S. pyogenes*) and the gram-negative pathogen of *Pseudomonas aeruginosa* (*P. aeruginosa*). Further, chronic wounds are very complex and hard to heal. Killing the bacteria is a critical element to enabling the healing process. The fact that AB-101 has efficacy against both gram-positive and gram-negative pathogens provides unique efficacy for a drug compound, along with AB-101's MTT properties.

Taken in total, AB-101 is a novel first-in-class of a new class of broad spectrum topical antibiotics called Multi- Target Therapeutics (MTT). The extract AB-101 Botanical Drug Substance (BDS) has multiple bioactive compounds making it a very effective antibiotic ideally suited for treating topical skin infections. The summary of indications AB-101 is effective against along with the associated pathogens causing the SSTI and wound infections and detailed ailments are shown in Table A.

TABLE A

| Topical Indication* | Pathogen* |
|---|---|
| Impetigo | *S. aureus*, MRSA, MRSA resistant to mupirocin, *S. pyogenes* |
| Atopic dermatitis | *S. aureus*, MRSA, MRSA resistant to mupirocin |
| Epidermolysis bullosa | *S. aureus*, MRSA, MRSA resistant to mupirocin, *S. pyogenes* and *P. aeruginosa* |
| Psoriasis | *S. aureus*, MRSA, MRSA resistant to mupirocin, |
| Skin colonized with pathogens (nose, ear and body) | *S. aureus*, MRSA, MRSA resistant to mupirocin |
| Wounds | *S. aureus*, MRSA, MRSA resistant to mupirocin, *S. pyogenes* and *P. aeruginosa* |

*Included and not limited to those skilled in the art.

Furthermore, AB-101 has demonstrated a unique safety profile that unexpectedly based on its physical properties enables maximizing drug delivery, while also increasing the safety profile. This unexpectant finding goes against the common understanding, to those familiar in the art. It is common convention to one familiar with the art the expectation to formulate a drug to be safe and effective, the dose needs to be as low as possible while delivering the desired efficacy. This is exactly opposite for AB-101. By maximizing the dose delivery, safety is also synergistically maximized as well. This combined with the fact that any lipophilic components of AB-101 would likely be absorbed by the skin leaving only hydrophilic components being available for bloodstream absorption. This would result in any AB-101 absorbed into the bloodstream to be naturally and readily eliminated through normal body functions. Systemic absorption would also be negligible, reducing any safety risks. This makes AB-101 a very potent and an extremely effective antibiotic designed to treat SSTI topical skin conditions.

Some embodiments herein are directed to a method of identifying a composition of latex of *Croton lechleri*, preferably a composition of filtered latex of *Croton lechleri*, preferably a composition of filtered latex of *Croton lechleri* Müll. Arg comprising: (a) determining the concentration of components of latex of *Croton lechleri*, preferably the concentration of components of filtered latex of *Croton lechleri*, preferably the concentration of components of filtered latex of *Croton lechleri* (b) comparing the concentrations of the components to the concentrations of the components of a reference standard; and (c) identifying a composition of latex of *Croton lechleri*, preferably a composition of filtered latex of *Croton lechleri*, preferably a composition of filtered latex of *Croton lechleri* Müll. Arg, wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard.

Some embodiments herein are directed to a method of identifying a composition of latex of *Croton lechleri*, preferably a composition of filtered latex of *Croton lechleri*, preferably a composition of filtered latex of *Croton lechleri* Müll. Arg for use in treating a bacterial colonization or primary or secondary bacterial infection of an underlying skin disorder in a subject comprising: (a) determining the concentration of components of latex of *Croton lechleri*, preferably the concentration of components of filtered latex of *Croton lechleri*, preferably the concentration of components of filtered latex of *Croton lechleri* (b) comparing the concentrations of the components to the concentrations of the components of a reference standard; and (c) identifying a composition of latex of *Croton lechleri*, preferably a composition of filtered latex of *Croton lechleri*, preferably a composition of filtered latex of *Croton lechleri* Müll. Arg for use in treating a bacterial colonization or primary or secondary bacterial infection of an underlying skin disorder in a subject, wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard.

Some embodiments herein are directed to a method of identifying a composition of latex of *Croton lechleri*, preferably a composition of filtered latex of *Croton lechleri*, preferably a composition of filtered latex of *Croton lechleri* Müll. Arg for use in treating or preventing or reducing the risk of a bacterial infection of or colonization that is secondary to an underlying skin disorder in a subject comprising: (a) determining the concentration of components of latex of *Croton lechleri*, preferably the concentration of components of filtered latex of *Croton lechleri*, preferably the concentration of components of filtered latex of *Croton lechleri* (b) comparing the concentrations of the components to the concentrations of the components of a reference standard; and (c) identifying a composition of latex of *Croton lechleri*, preferably a composition of filtered latex of *Croton lechleri*, preferably a composition of filtered latex of *Croton lechleri* Müll. Arg for use in treating or preventing or reducing the risk of a bacterial infection or colonization that is secondary to an underlying skin disorder in a subject, wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard.

In certain embodiments, the specific dragon's blood tree of the present application is *Croton lechleri* Müll. Arg. of the Family: Euphorbiaceae. Dragon's blood is also referred to as Sangre de drago (Peru), Sangre de grado (Ecuador). Embodiments of the present invention are directed to pharmaceutical compositions of latex of *Croton lechleri*, preferably filtered latex of *Croton lechleri*, preferably filtered latex of *Croton lechleri* Müll. Arg and a pharmaceutically acceptable excipient. Such pharmaceutical compositions have been found to be useful in the successful treatment of infection or colonization that is secondary to an underlying skin disorder using the same. In some embodiments the pharmaceutical compositions are administered topically. In some embodiments the pharmaceutical compositions are administered nasally. Embodiments are directed to pharmaceutical compositions comprising latex of *Croton lechleri*, preferably filtered latex of *Croton lechleri*, preferably filtered latex of *Croton lechleri* Müll. Arg wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard, disclosed herein together with a pharmaceutically acceptable carrier, as well as methods of making and using the compounds and compositions. Certain embodiments are directed to methods for inhibiting infection or colonization that is secondary to an underlying skin disorder. Other embodiments are directed to methods for treating infection or colonization that is secondary to an underlying skin disorder in a patient in need of such treatment, comprising administering to said patient a therapeutically effective amount of a composition according to the present invention. Also provided is the use of certain extracts of *Croton lechleri* disclosed herein in the manufacture of a medicament for the treatment of infection or colonization that is secondary to an underlying skin disorder.

Pharmaceutical Compositions

Embodiments herein are directed to pharmaceutical compositions comprising latex of *Croton lechleri*, preferably filtered latex of *Croton lechleri*, preferably filtered latex of *Croton lechleri* Müll. Arg., wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard, which have been found to be useful in the successful treatment of a bacterial infection or colonization that is secondary to an underlying skin disorder in a subject.

The pharmaceutical AB-101 composition uses the whole *Croton lechleri* MÜll. Arg latex. The art is full of examples where the *Croton lechleri* Mel Arg latex is fractionated, individual components are isolated or individual components are minimized or eliminated. This may be a result of the specific use. For the pharmaceutical grade of AB-101, the preference is to use the entire extract to leverage the synergy associated with all the active compounds.

Importantly, the variation of all the compounds vary greatly as indicated by the geography, environment, soil, elevation and age of the trees to name a few of the key variables. These variations are highlighted by Thiago Vaz Lopes, Dragon's blood (*Croton lechleri* MÜll. Arg; An Update on the Chemical Composition and Medical Applications of This Natural Plant Extract, Revista Brasileira de Higiene and Animal Health (v. 7, n2) p. 167-192 (2013)).

The AB-101 novelty is based upon identifying the linkage between the specific compounds and their levels of concentration within AB-101 via a bioassay to in vitro efficacy and confirming via human use testing as an effective treatment for wound treating, bleeding treatment, and fighting infections. The utility of this novel discovery is the basis for developing a pharmaceutical drug and a medicinal product that will meet the FDA standards.

The FDA has established the requirement of having a bioassay that correlates the performance of the botanical raw material based on the chemical characterization of the composition and changes therein, to the efficacy against wound treating, bleeding treatment, and fighting infections.

The *Croton lechleri* MÜll. Arg latex latex is complex, difficult and not straightforward to define since its composition uses the full accompaniment of all of the bioactive materials comprising the *Croton lechleri* MÜll. Arg latex. Net, finding the critical active markers and performance and safety tests requires novel discovery.

The FDA requires the identification of the critical biomarkers or active constituents that drives the bioactivity. To that end, the critical biomarkers and their associated concentrations for AB-101 have never been published, defined or identified as associated with wound healing properties, antimicrobial activity and safety for treatment of wound treating, bleeding treatment, and fighting infections. Without this information, the FDA will not grant a drug status for medicinal use which is at the heart of becoming a pharmaceutical drug.

"Pharmaceutical Products" means any product, compound, medicine or therapeutic which is subject to regulation as a drug, medicine or controlled substance by a foreign equivalent of the United States Food and Drug Administration.

Fda Guidance on Botanicals States:

Because of the heterogeneous nature of a botanical drug and possible uncertainty about its active constituents, one of the critical issues for botanical drugs is ensuring that the therapeutic effect for marketed drug product batches is consistent. In general, therapeutic consistency can be supported by a "totality of the evidence" approach, including the following considerations:

- Botanical raw material control (e.g, agricultural practice and collection).
- Quality control by chemical test(s) (e.g., analytical tests such as spectroscopic and/or chromatographic methods that capture the active chemical constituents of a botanical drug substance) and manufacturing control (e.g., process validation).
- Biological assay (e.g. a biological assay that reflects the drug's known or intended mechanism of action) and clinical data (for details regarding use of clinical data in ensuring therapeutic consistency.

By using the whole *Croton lechleri* MÜll. Arg latex a unique synergy can be obtained across the entire composition that meets the specific bioassay performance targets. Table B shows 20 bioactives found in the pharmaceutical grade of AB-101. These bioactive compounds provide efficacy for: antimicrobial, antiviral, anti-inflammatory, cell proliferation to promote healing, anticancer, hemostatic, antioxidant and fibroblast stimulation to promote healing. By maintaining the *Croton lechleri* MÜll. Arg latex intact, a tremendous synergy is obtained across wound healing and preventing infections.

Table B shows bioactive compounds found in the whole *Croton lechleri* MÜll. Arg latex of AB-101 and their properties.

TABLE B

| Bioactive Chemical Components | Phytochemical Compound Class | Antimicrobial | Antiviral | Anti-inflammatory | Cell Proliferative (Wound Healing) | Anticancer | Hemostat | Antioxidant | Stimulating fibroblasts (Wound Healing) |
|---|---|---|---|---|---|---|---|---|---|
| 1,3,5-Trimethyoxy benzene | Flavonoid | X | | | | | | | |

TABLE B-continued

| Bioactive Chemical Components | Phytochemical Compound Class | Antimicrobial | Antiviral | Anti-inflammatory | Cell Proliferative (Wound Healing) | Anticancer | Hemostat | Antioxidant | Stimulating fibroblasts (Wound Healing) |
|---|---|---|---|---|---|---|---|---|---|
| 2,4,6-Trimethoxyphenol | Phenol | X | X | | | X | | | |
| 3',4-O-dimethylcedrusin | Lignin | | | | | | | | X |
| 4-O-Dimethylcedrusin | Lignin | | | | X | | | | |
| Boldine, iso | Alkaloid | | | X | | X | | | |
| Catechin | Flavonoid | X | X | X | | | X | X | |
| Epicatechin | Flavonoid | | X | X | | | | X | |
| Epigallocatechin | Phenol | X | | | | | | X | |
| Flavan-3-ols | Flavonoids | X | X | | | | | | |
| Gallocatechin | Flavonoid | X | X | | X | | | X | |
| Magnoflorine | Alkaloid | X | X | X | | | | | |
| Proanthocyanidins | Polyphenols | X | X | X | X | X | | X | |
| Procyanidin | Flavonoids | X | X | X | X | | | | |
| Prodelphinidin | Tannins | X | | | | | | | |
| Sitosterol-Beta-Glucopyranoside | Phytosterol | X | X | X | | | | | |
| Taspine | Alkaloid | X | X | X | | X | | | |
| Catechin gallate | Polyphenols | X | X | X | X | X | | X | X |
| Epicatechin gallate | Polyphenols | X | | | X | X | | X | X |
| Epigallocatechin gallate | Polyphenols | X | X | X | X | X | | X | X |
| Gallocatechin gallate | Polyphenols | X | | | X | | | X | X |

Some embodiments herein are directed to a pharmaceutical composition comprising latex of *Croton lechleri*, preferably filtered latex of *Croton lechleri*, preferably filtered latex of *Croton lechleri* Müll. Arg., wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard, of embodiments herein and a pharmaceutically acceptable excipient. Optionally, the pharmaceutical composition may further comprise one or more other therapeutic ingredients. In embodiments, the pharmaceutical composition comprises a therapeutically effective amount of the latex of *Croton lechleri*, preferably filtered latex of *Croton lechleri*, preferably filtered latex of *Croton lechleri* Müll. Arg., wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard. In embodiments, the pharmaceutical composition is suitable for topical administration or is a topical pharmaceutical composition. In some embodiments latex of *Croton lechleri*, preferably filtered latex of *Croton lechleri*, preferably filtered latex of *Croton lechleri* Müll. Arg. has a PDI of embodiments disclosed herein.

Embodiments herein are directed to pharmaceutical compositions comprising latex of *Croton lechleri*, preferably filtered latex of *Croton lechleri*, preferably filtered latex of *Croton lechleri* Müll. Arg., wherein the pharmaceutical composition does not contain a pharmaceutically acceptable excipient. In certain embodiments, latex of *Croton lechleri*, preferably filtered latex of *Croton lechleri*, preferably filtered latex of *Croton lechleri* Müll. Arg. comprises one or more compounds selected from: gallocatechin, epigallocatechin, catechin, epicatechin, taspine, and dimethylcedrusin and combinations thereof. Each of gallocatechin, epigallocatechin, catechin, epicatechin, taspine, and dimethylcedrusin may be present in the latex of *Croton lechleri*, preferably filtered latex of *Croton lechleri*, preferably filtered latex of *Croton lechleri* Müll. Arg. in at least the amounts found in Table 1a or any combination of such amounts.

Embodiments herein are directed to pharmaceutical compositions comprising latex of *Croton lechleri*, preferably filtered latex of *Croton lechleri*, preferably filtered latex of *Croton lechleri* Müll. Arg. and a pharmaceutically acceptable excipient. In certain embodiments, latex of *Croton lechleri*, preferably filtered latex of *Croton lechleri*, preferably filtered latex of *Croton lechleri* Müll. Arg. comprises one or more compounds selected from: gallocatechin, epigallocatechin, catechin, epicatechin, taspine, and dimethylcedrusin and combinations thereof. Each of gallocatechin, epigallocatechin, catechin, epicatechin, taspine and dimethylcedrusin may be present in the latex of *Croton lechleri*, preferably filtered latex of *Croton lechleri*, preferably filtered latex of *Croton lechleri* Müll. Arg. in at least the amounts found in Table 1a or any combination of such amounts.

As shown in Table B, there are a broad range of compounds present in AB-101. The primary bioactive reference standard for the pharmaceutical grade of AB-101 are the Gallocatechin, Epigallocatechin, Catechins, Epicatechin, Taspine and Dimethylcedrusin. Of particular importance is a secondary set of polyphenol bioactives composed of the gallate family including Catechin Gallate (CG), Epicatechin Gallate (ECG), Gallocatechin Gallate (GCG) and Epigallocatechin Gallate (EGCG). The gallate family bioactive profile of particular importance to AB-101 include the antimicrobial and antioxidants properties. These properties have been noted and indicated in Rahardiyan, Dino. (2018), Antibacterial potential of catechin of tea (*Camellia sinensis*) and its applications, Food Research. 3. 1-6, and Multifunctional Antioxidant Activities of Alkyl Gallates *The Open Bioactive Compounds Journal,* 2010, 3: 1-11 Isao Kubo, Noriyoshi Masuoka, Tae Joung Ha, Kuniyoshi Shimizu, Ken-ichi Nihei.

From a composition standpoint the primary and secondary bioactives compose between 80% to 99% of the concentration composition of the pharmaceutical grade of AB-101, where the remaining other compounds not characterized comprise the remaining whole of AB-101. Within the whole, the gallate bioactive family can contribute between 1% to 20% of the bioactive. For AB-101 Lot 01, the primary bioactive reference range is between 85% to 90%, the secondary reference range is between 3% to 4% and the total compounds not characterized in AB-101 ranges from 7% to 11%.

The contribution of the entire *Croton lechleri* Müll. Arg latex having a unique synergy across the entire composition that meets the specific bioassay performance targets resulting in a composition that has great natural polydispersity as measured by a Polydispersity Index Analysis. The primary reference standard is the main focus of the pharmaceutical grade of AB-101's bioactivity, where the secondary reference standard demonstrates the biodiversity, the polydispersity and synergy makeup within AB-101, which also contributes to AB-101 efficacy.

TABLE 1a

| Compound | Exemplary Amount present in the latex (PPM is in μg/g) |
|---|---|
| Gallocatechin | at least about 110 PPM |
| Epigallocatechin | at least about 780 PPM |
| Catechin | at least about 1.6 PPM |
| Epicatechin | at least about 2 PPM |
| Taspine | at least about 45 PPM |
| Dimethylcedrusin | at least about 0.1 PPM |

TABLE 1b

| Compound or compounds | Exemplary Amount present in the latex as a % of total Proanthocyanidins (PAC) |
|---|---|
| Gallocatechin and Epigallocatechin combined | at least about 60% |
| Epigallocatechin | at least about 45% |

TABLE 1c

| Exemplary Antibiotic Activity | | |
|---|---|---|
| Bacteria | Exemplary MIC | Exemplary MBC |
| *Methicillin-susceptible Staphylococcus aureus* (MSSA) | 50 μg/mL or less | 50 μg/mL or less |
| *Methicillin-resistant Staphylococcus aureus* (MRSA) | 50 μg/mL or less | 50 μg/mL or less |
| *Pseudomonas aeruginosa* | 50 μg/mL or less | 50 μg/mL or less |
| *Streptococcus pyongenes* | 50 μg/mL or less | 50 μg/mL or less |

TABLE 1d

| Exemplary LogP for each of gallocatechin, epigallocatechin, catechin, epicatechin, and taspine | |
|---|---|
| IVPT: Skin Permeation Flux Calculation for ECG | at least about less than 500 $\mu g/cm^2/hr$ |
| IVRT: API (Active Pharmacetuica Ingredient) Release Flux Calculation for ECG | at least about less than 2400 $\mu g/cm^2/hr$ |
| ECG LogP: Partition Coefficient Calculation | at least about or less than 2.5 |

TABLE 1e

| Exemplary Additional Properties | |
|---|---|
| Film Forming Properties | Present as observed on skin |

If the latex of *Croton lechleri*, preferably filtered latex of *Croton lechleri*, preferably filtered latex of *Croton lechleri* Müll. Arg. fails to contain the amounts of gallocatechin, epigallocatechin, catechin, epicatechin, taspine and dimethylcedrusin in at least the amounts set forth in Table 1a, it is not suitable for use in the pharmaceutical compositions and methods of use described herein.

In some embodiments, the gallocatechin present in the latex is in an amount of at least about 110 PPM, at least about 115 PPM, at least about 120 PPM, at least about 125 PPM, at least about 130 PPM, at least about 135 PPM, at least about 140 PPM, at least about 145 PPM, at least about 150 PPM, at least about 155 PPM, at least about 160 PPM, at least about 165 PPM, at least about 170 PPM, at least about 175 PPM, at least about 180 PPM, at least about 185 PPM, at least about 190 PPM, at least about 195 PPM, at least about 200 PPM, or a range between any two of these values.

In some embodiments, the epigallocatechin present in the latex is in an amount of at least about 780 PPM, at least about 790 PPM, at least about 800 PPM, at least about 810 PPM, at least about 820 PPM, at least about 830 PPM, at least about 840 PPM, at least about 850 PPM, at least about 860 PPM, at least about 870 PPM, at least about 880 PPM, at least about 890 PPM, at least about 900 PPM, at least about 910 PPM, at least about 920 PPM, at least about 930 PPM, at least about 940 PPM, at least about 950 PPM, at least about 960 PPM, at least about 970 PPM, at least about 980 PPM, at least about 990 PPM, at least about 1000 PPM, at least about 1010 PPM, at least about 1020 PPM, at least about 1030 PPM, at least about 1040 PPM, at least about 1050 PPM, at least about 1060 PPM, at least about 1070 PPM, at least about 1080 PPM, at least about 1090 PPM, at least about 1100 PPM, at least about 1110 PPM, at least about 1120 PPM, at least about 1130 PPM, at least about 1140 PPM, at least about 1150 PPM, at least about 1160 PPM, at least about 1170 PPM, at least about 1180 PPM, at least about 1190 PPM, at least about 1200 PPM, at least about 1210 PPM, at least about 1220 PPM, at least about 1230 PPM, at least about 1240 PPM, at least about 1250 PPM, at least about 1260 PPM, at least about 1270 PPM, at least about 1280 PPM, at least about 1290 PPM, at least about 1300 PPM, at least about 1310 PPM, at least about 1320 PPM, at least about 1330 PPM, at least about 1340 PPM, at least about 1350 PPM, at least about 1360 PPM, at least about 1370 PPM, at least about 1380 PPM, at least about 1390 PPM, at least about 1400 PPM, at least about 1410 PPM, at least about 1420 PPM, at least about 1430 PPM, at least about 1440 PPM, at least about 1450 PPM, at least about 1460 PPM, at least about 1470 PPM, at least about 1480 PPM, at least about 1490 PPM, at least about 1500 PPM, at least about 1510 PPM, at least about 1520 PPM, at least about 1530 PPM, at least about 1540 PPM, at least about 1550 PPM, at least about 1560 PPM, at least about 1570 PPM, at least about 1580 PPM, at least about 1590 PPM, at least about 1600 PPM, at least about 1610 PPM, at least about 1620 PPM, at least about 1630 PPM, at least about 1640 PPM, at least about 1650 PPM, at least about 1660 PPM, at least about 1670 PPM, at least about 1680 PPM, at least about 1690 PPM, at least about 1700 PPM, or a range between any two of these values.

In some embodiments, the catechin present in the latex is in an amount of at least about 1.6 PPM, at least about 1.7 PPM, at least about 1.8 PPM, at least about 1.9 PPM, at least about 2.0 PPM, at least about 2.1 PPM, at least about 2.2 PPM, at least about 2.3 PPM, at least about 2.4 PPM, at least about 2.5 PPM, at least about 2.6 PPM, at least about 2.7 PPM, at least about 2.8 PPM, at least about 2.9 PPM, at least about 3.0 PPM, at least about 3.1 PPM, at least about 3.2 PPM, at least about 3.3 PPM, at least about 3.4 PPM, at least about 3.5 PPM, at least about 3.6 PPM, at least about 3.7 PPM, at least about 3.8 PPM, at least about 3.9 PPM, at least about 4.0 PPM, at least about 4.1 PPM, at least about 4.2 PPM, at least about 4.3 PPM, at least about 4.4 PPM, at least about 4.5 PPM, at least about 4.6 PPM, at least about 4.7 PPM, at least about 4.8 PPM, at least about 4.9 PPM, at least about 5.0 PPM, at least about 5.1 PPM, at least about 5.2 PPM, at least about 5.3 PPM, at least about 5.4 PPM, at least about 5.5 PPM, at least about 5.6 PPM, at least about 5.7 PPM, at least about 5.8 PPM, at least about 5.9 PPM, at least about 6.0 PPM, at least about 6.1 PPM, at least about 6.2 PPM, at least about 6.3 PPM, at least about 6.4 PPM, at least about 6.5 PPM, at least about 6.6 PPM, at least about 6.7 PPM, at least about 6.8 PPM, at least about 6.9 PPM, at least about 7.0 PPM, at least about 7.1 PPM, at least about 7.2 PPM, at least about 7.3 PPM, at least about 7.4 PPM, at least about 7.5 PPM, at least about 7.6 PPM, at least about 7.7 PPM, at least about 7.8 PPM, at least about 7.9 PPM, at least about 8.0 PPM, at least about 8.1 PPM, at least about 8.2 PPM, at least about 8.3 PPM, at least about 8.4 PPM, at least about 8.5 PPM, at least about 8.6 PPM, at least about 8.7 PPM, at least about 8.8 PPM, at least about 8.9 PPM, at least about 9.0 PPM, at least about 9.1 PPM, at least about 9.2 PPM, at least about 9.3 PPM, at least about 9.4 PPM, at least about 9.5 PPM, at least about 9.6 PPM, at least about 9.7 PPM, at least about 9.8 PPM, at least about 9.9 PPM, at least about 10.0 PPM, at least about 10.1 PPM, at least about 10.2 PPM, at least about 10.3 PPM, at least about 10.4 PPM, at least about 10.5 PPM, at least about 10.6 PPM, at least about 10.7 PPM, at least about 10.8 PPM, at least about 10.9 PPM, at least about 11.0 PPM, or a range between any two of these values.

In some embodiments, the epicatechin present in the latex is in an amount of at least about 2.0 PPM, at least about 2.1 PPM, at least about 2.2 PPM, at least about 2.3 PPM, at least about 2.4 PPM, at least about 2.5 PPM, at least about 2.6 PPM, at least about 2.7 PPM, at least about 2.8 PPM, at least about 2.9 PPM, at least about 3.0 PPM, at least about 3.1 PPM, at least about 3.2 PPM, at least about 3.3 PPM, at least about 3.4 PPM, at least about 3.5 PPM, at least about 3.6 PPM, at least about 3.7 PPM, at least about 3.8 PPM, at least about 3.9 PPM, at least about 4.0 PPM, at least about 4.1 PPM, at least about 4.2 PPM, at least about 4.3 PPM, at least about 4.4 PPM, at least about 4.5 PPM, at least about 4.6 PPM, at least about 4.7 PPM, at least about 4.8 PPM, at least about 4.9 PPM, at least about 5.0 PPM, at least about 5.1 PPM, at least about 5.2 PPM, at least about 5.3 PPM, at least about 5.4 PPM, at least about 5.5 PPM, at least about 5.6 PPM, at least about 5.7 PPM, at least about 5.8 PPM, at least about 5.9 PPM, at least about 6.0 PPM, at least about 6.1 PPM, at least about 6.2 PPM, at least about 6.3 PPM, at least about 6.4 PPM, at least about 6.5 PPM, at least about 6.6 PPM, at least about 6.7 PPM, at least about 6.8 PPM, at least about 6.9 PPM, at least about 7.0 PPM, at least about 7.1 PPM, at least about 7.2 PPM, at least about 7.3 PPM, at least about 7.4 PPM, at least about 7.5 PPM, at least about 7.6 PPM, at least about 7.7 PPM, at least about 7.8 PPM, at least about 7.9 PPM, at least about 8.0 PPM, at least about 8.1 PPM, at least about 8.2 PPM, at least about 8.3 PPM, at least about 8.4 PPM, at least about 8.5 PPM, at least about 8.6 PPM, at least about 8.7 PPM, at least about 8.8 PPM, at least about 8.9 PPM, at least about 9.0 PPM, at least about 9.1 PPM, at least about 9.2 PPM, at least about 9.3 PPM, at least about 9.4 PPM, at least about 9.5 PPM, at least about 9.6 PPM, at least about 9.7 PPM, at least about 9.8 PPM, at least about 9.9 PPM, at least about 10.0 PPM, or a range between any two of these values.

In some embodiments, the taspine present in the latex is in an amount of at least about 45 PPM, at least about 46 PPM, at least about 47 PPM, at least about 48 PPM, at least about 49 PPM, at least about 50 PPM, at least about 51 PPM, at least about 52 PPM, at least about 53 PPM, at least about 54 PPM, at least about 55 PPM, at least about 56 PPM, at least about 57 PPM, at least about 58 PPM, at least about 59 PPM, at least about 60 PPM, at least about 61 PPM, at least about 62 PPM, at least about 63 PPM, at least about 64 PPM, at least about 65 PPM, or a range between any two of these values.

In some embodiments, the dimethylcedrusin present in the latex is in an amount of at least about 0.1 mg of dimethylcedrusin/kg of latex, at least about 0.11 PPM, at least about 0.12 PPM, at least about 0.13 PPM, at least about 0.14 PPM, at least about 0.15 PPM, at least about 0.16 PPM, at least about 0.17 PPM, at least about 0.18 PPM, at least about 0.18 PPM, at least about 0.19 PPM, at least about 0.20 PPM, at least about 0.21 PPM, at least about 0.22 PPM, at least about 0.23 PPM, at least about 0.24 PPM, at least about 0.25 PPM, at least about 0.26 PPM, at least about 0.27 PPM, at least about 0.28 PPM, at least about 0.29 PPM, at least about 0.30 PPM, at least about 0.31 PPM, at least about 0.32 PPM, at least about 0.33 PPM, at least about 0.34 PPM, at least about 0.35 PPM, at least about 0.36 PPM, at least about 0.37 PPM, at least about 0.38 PPM, at least about 0.39 PPM, about 0.40 PPM, at least about 0.41 PPM, at least about 0.42 PPM, at least about 0.43 PPM, at least about 0.44 PPM, at least about 0.45 PPM, at least about 0.46 PPM, at least about 0.47 PPM, at least about 0.48 PPM, at least about 0.49 PPM, at least about 0.5 PPM, at least about 0.6 PPM, at least about 0.7 PPM, at least about 0.8 PPM, at least about 0.9 PPM, at least about 1.0 PPM, at least about 1.1 PPM, at least about 1.2 PPM, at least about 1.3 PPM, at least about 1.4 PPM, at least about 1.5 PPM, at least about 1.6 PPM, at least about 1.7 PPM, at least about 1.8 PPM, at least about 1.9 PPM, at least about 2.0 PPM, at least about 2.1 PPM, at least about 2.2 PPM, at least about 2.3 PPM, at least about 2.4 PPM, at least about 2.5 PPM, at least about 2.6 PPM, at least about 2.7 PPM, at least about 2.8 PPM, at least about 2.9 PPM, at least about 3.0 PPM, at least about 3.1 PPM, at least about 3.2 PPM, at least about 3.3 PPM, at least about 3.4 PPM, at least about 3.5 PPM, at least about 3.6 PPM, at least about 3.7 PPM, at least about 3.8 PPM, at least about 3.9 PPM, at least about 4.0 PPM, at least about 4.1 PPM, at least about 4.2 PPM, at least about 4.3 PPM, at least about 4.4 PPM, at least about 4.5 PPM, at least about 4.6 PPM, at least about 4.7 PPM, at least about 4.8 PPM, at least about 4.9 PPM, at least about 5.0 PPM, at least about 5.1 PPM, at least about 5.2 PPM, at least about 5.3 PPM, at least about 5.4 PPM, at least about 5.5 PPM, at least about 5.6 PPM, at least about 5.7 PPM, at least about 5.8 PPM, at least about 5.9 PPM, at least about 6.0 PPM, at least about 6.1 PPM, at least about 6.2 PPM, at least about 6.3 PPM, at least about 6.4 PPM, at least about 6.5 PPM, at least about 6.6 PPM, at least about 6.7 PPM, at least about 6.8 PPM, at least about 6.9 PPM, at least about 7.0 PPM, at least about 7.1 PPM, at least about 7.2 PPM, at least about 7.3 PPM, at least about 7.4 PPM, at least about 7.5 PPM, at least about 7.6 PPM, at least about 7.7 PPM, at least about 7.8 PPM, at least about 7.9 PPM, at least about 8.0 PPM, at least about 8.1 PPM, at least about 8.2 PPM, at least about 8.3 PPM, at least about 8.4 PPM, at least about 8.5 PPM, at least about 8.6 PPM, at least about 8.7 PPM, at least about 8.8 PPM, at least about 8.9 PPM, at least about 9.0 PPM, at least about 9.1 PPM, at least about 9.2 PPM, at least about 9.3 PPM, at least about 9.4 PPM, at least about 9.5 PPM, at least about 9.6 PPM, at least about 9.7 PPM, at least about 9.8 PPM, at least about 9.9 PPM, at least about 10.0 PPM, or a range between any two of these values.

Polydispersity Index (PDI) is used to measure the breadth of the molecular weight distribution of AB-101. PDI is used to indicate distribution of polymer chain molecular weights in a given polymer, as the PDI value increases the heterogeneity in cross-linking, network formation, chain length, branching, hyper branching is increased and will have a more random arrangement. PDI is an important measure to characterize the unique compositional nature of AB-101 or other *Croton lechleri* derived compositions.

In any of the embodiments disclosed herein, the latex of *Croton lechleri*, preferably filtered latex of *Croton lechleri*, preferably filtered latex of *Croton lechleri* Müll. Arg has a PDI of about 0.5 to 0.85, about 0.55 to 0.85, about 0.6 to 0.85, about 0.65 to 0.85, about 0.7 to 0.85, about 0.75 to 0.85, about 0.8 to 0.85, about 0.5 to about 0.8, about 0.5 to about 0.75, about 0.5 to about 0.7, about 0.5 to about 0.65, about 0.5 to about 0.6, 0.5 to about 0.55, or a value within one of these ranges. Specific examples may include about 0.5, about 0.55, about 0.6, about 0.65, about 0.7, about 0.75, about 0.8, about 0.85, or a range between any two of these values. In some embodiments, the latex of *Croton lechleri*, preferably filtered latex of *Croton lechleri*, preferably filtered latex of *Croton lechleri* Müll. Arg has a PDI of about 0.81.

The pharmaceutical composition of AB-101 as described and claimed herein is a plant sourced material that meets the criteria of being consistently reproducible between batch to batch and reliably delivers the desired health benefits via topical application that may be used in a pharmaceutical composition. It can be used to treat a bacterial colonization or primary or secondary bacterial infection of an underlying skin disorder. Plant sourced materials face the challenge that changes in environmental weather, climate, rainfall, time of harvest (via season, time of day or month), changes in geography, longitude location, latitude location, altitude, changes in soil condition, harvesting protocols and many additional conditions can alter the characteristics of the plant that could impact quality. This can impact the plant's bioactivity resulting in inconsistency in achieving desired performance outcome. This creates a challenge in defining a pharmaceutical grade of dragon's blood to deliver consistent and reproducible therapeutic benefits. This is further compounded by the wide variety of the different species called dragon's blood. For example, phytochemical and anti-staphylococcal biofilm assessment of *Dracaena draco* L. Spp. *draco* resin, referred as dragon's blood, is "inactive in the maximum tested concentration of 1000 mcg/ml against free living staphylococci." In contrast, AB-101 (latex of *Croton lechleri*, preferably filtered latex of *Croton lechleri*, preferably filtered latex of *Croton lechleri* Müll. Arg. with the appropriate levels of gallocatechin, epigallocatechin, catechin, epicatechin, taspine, and dimethylcedrusin) is effective against *Staphylococcus* specifically methicillin-susceptible *Staphylococcus aureus* (MSSA) or the shorten nomenclature staph bacteria and in particular methicillin-resistant *Staphylococcus aureus* (MRSA) and in particular Mupirocin resistant MRSA. The generic name of the *Croton lechleri* resin, ie, dragon's blood, or Sangre de grado, creates confusion in defining a plant-derived pharmaceutical and demonstrates that not all *Croton lechleri* plants are the same, nor do they provide similar benefits.

The benefits of AB-101, filtered or unfiltered latex of *Croton lechleri*, preferably filtered latex of *Croton lechleri*, preferably filtered latex of *Croton lechleri* Müll. Arg., is its ability to deliver consistent results for treating the pathogens between batch to batch in spite of all the confounding conditions. The challenge in using the whole latex is to identify the compounds that deliver performance based on the many bio-active compounds comprising the latex. Even within the same species, grown in a similar location, there are variations in chemical content and bioactivity of the whole latex that unexpectedly varies in its ability to fight and kill pathogens.

Methodology that can identify the whole latex is effective by having an assay that determines when a batch meets the predetermined performance criteria. Having a unique analytical and microbiological assay enables the ability to identify which batch of filtered or unfiltered latex of *Croton lechleri*, preferably filtered latex of *Croton lechleri*, preferably filtered latex of *Croton lechleri* Müll. Arg, has the combination of components that will consistently deliver the desired outcome.

AB-101 botanical raw material (BRM) is a complex botanical product that is a latex of *Croton lechleri*, preferably filtered latex of *Croton lechleri*, preferably filtered latex of *Croton lechleri* Müll. Arg. that contains certain marker compounds (catechin, gallocatechin, epicatechin, epigallocatechin, taspine, and dimethylcedrusin) in specified amounts (see Table 1a). Utilization of liquid chromatography with tandem mass spectrometry (LC-MS/MS) can be used to characterize the existence and levels of such marker compounds for batch to batch consistency and repeatable performance of AB-101. Marker compounds in AB-101 BRM include the proanthocyanidins: catechin, gallocatechin, epicatechin, and epigallocatechin, the alkaloid taspine, and the lignin dimethylcedrusin.

The published and accepted taxonomic classification of *Croton lechleri* Müll. Arg. is the following (van Ee & Berry, 2011, Riina et al, 2009, The Plant List, 2012, The Angiosperm Phylogeny Group, 2009):

Division: Streptophyta
Class: Equisetopsida
Subclass: Magnoliidae
Order: Malpighiales
Family: Euphorbiaceae
Genus: Croton
Subgenus: Adenophylli
Section: Cyclostigma -continued

| | |
|---|---|
| Subsection: | Cyclostigma |
| Species: | *Croton lechleri* Müll. Arg. |

Biodiversity of botanicals plays a major role in constituent chemical compound characterization. Chemical compounds utilized for as important batch to batch consistency of AB-101 need to 1) demonstrate antimicrobial or cicatrizant properties, 2) be present in AB-101, and 3) be detectable using analytical techniques. Using these criteria, the analytical efforts focused on 3 classes of compounds: polyphenols (proanthocyanidins) alkaloids (taspine) and lignin (dimethylcedrusin). Within the proanthocyanidin class, 4 specific compounds were focused on: catechin, epicatechin, gallocatechin, and epigallocatechin. The compound of importance within the alkaloid class is taspine. Finally, the compound of importance within the lignin class is dimethylcedrusin. Each of these compounds fulfills the three required elements detailed above. The following are the chemical structures of the 6 compounds utilized as important markers for batch to batch consistency of AB-101.

Proanthocyanidins

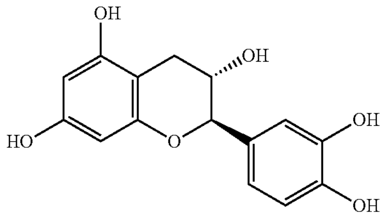

(+) catechin

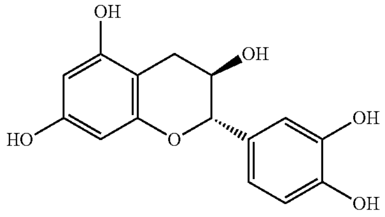

(-) epicatechin

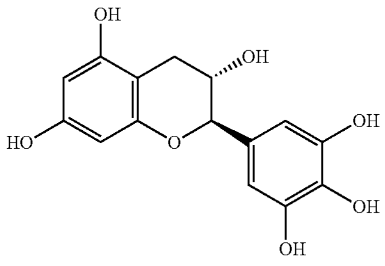

(+) gallocatechin

-continued

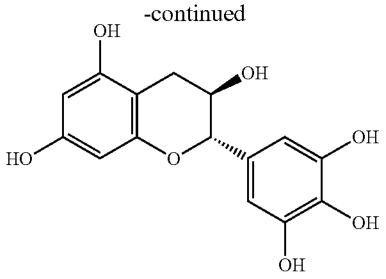

(-) epigallocatechin

Alkaloid

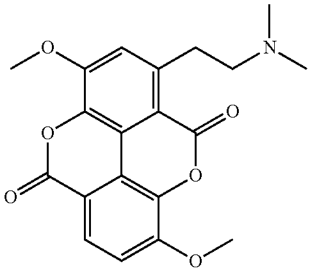

taspine

Lignin

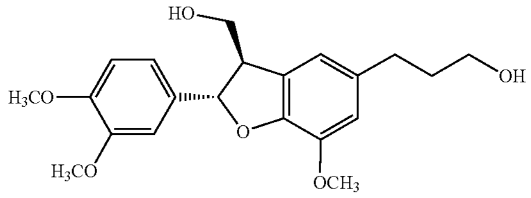

dimethylcedrusin

For characterization studies, AB-101 extract was lyophilized and the lyophilized powder was subjected to three different extraction methods.

Method 1—Ultrasonic polyphenol extraction. The lyophilized AB-101 extract was dissolved into methanol. The resultant emulsion was then subjected to sonication for 10 minutes followed by centrifugation to remove particulates for 5 minutes. The supernatant was then subjected to LC-MS/MS analysis.

Method 2—Soxhlet extraction. The lyophilized AB-101 extract was subjected to a Soxhlet extraction with 80% ethanol. The ethanol was removed via a rotary evaporator. The resultant material was then subjected re-suspended in ethanol then subjected to LC-MS/MS analysis.

Method 3—Polyphenol extraction. The lyophilized AB-101 extract was incubated with methanol overnight at room temperature and in the dark. The supernatant was then filtered using Whatman filters, dried, and then re-suspended in methanol. The resultant material was then subjected to LC-MS/MS analysis.

Figure 6:
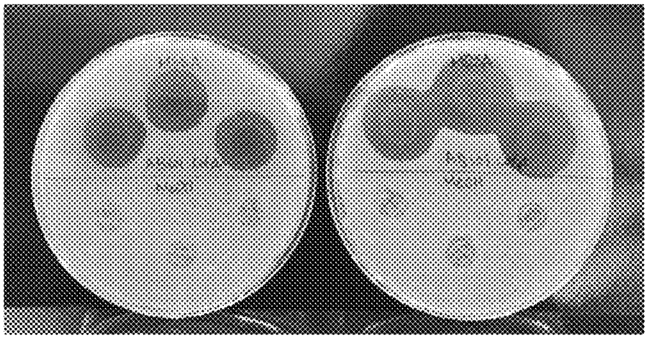
FIG. 6 depicts the zone of inhibition of of methanol extracted AB-101 against methicillin-susceptible *Staphylococcus aureus* (MSSA) (on the left) and methicillin-resistant *Staphylococcus aureus* (MRSA) (on the right).

FIG. 1 depicts a representative Total Ion Chromatogram as well as additional Multiple Reaction Monitoring spectra that identify the important marker compounds in an AB-101 extract. While FIG. 6 depicts a representative Total Ion Chromatogram of dimethylcedrusin. The compounds are detectable using any of the three extraction methods.

Figure 2A:
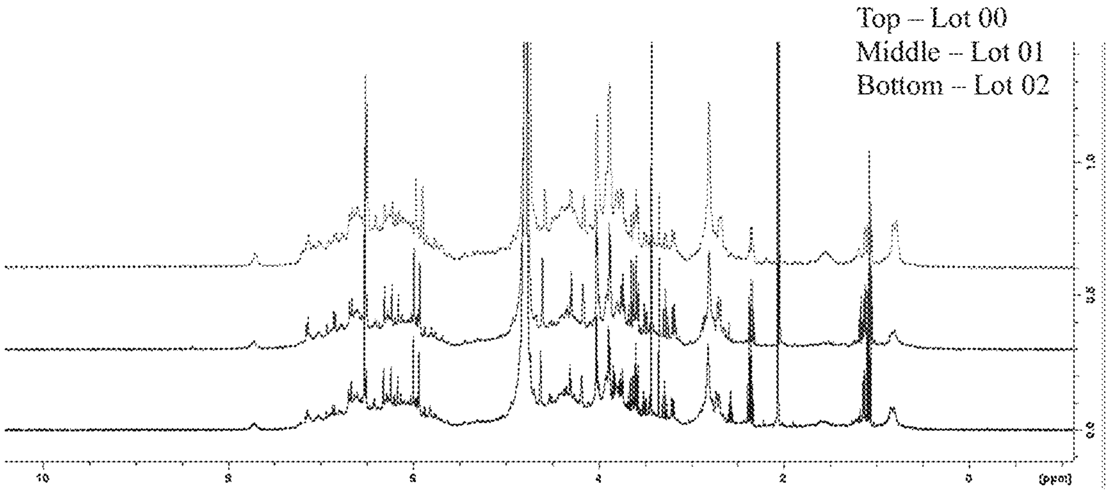
FIG. 2A depicts the NMR spectra of 3 lots of AB-101 in $D_2O$—the top spectra is for Lot 00, the middle spectra is for Lot 01, and the bottom spectra is for Lot 02.
Figure 2B:
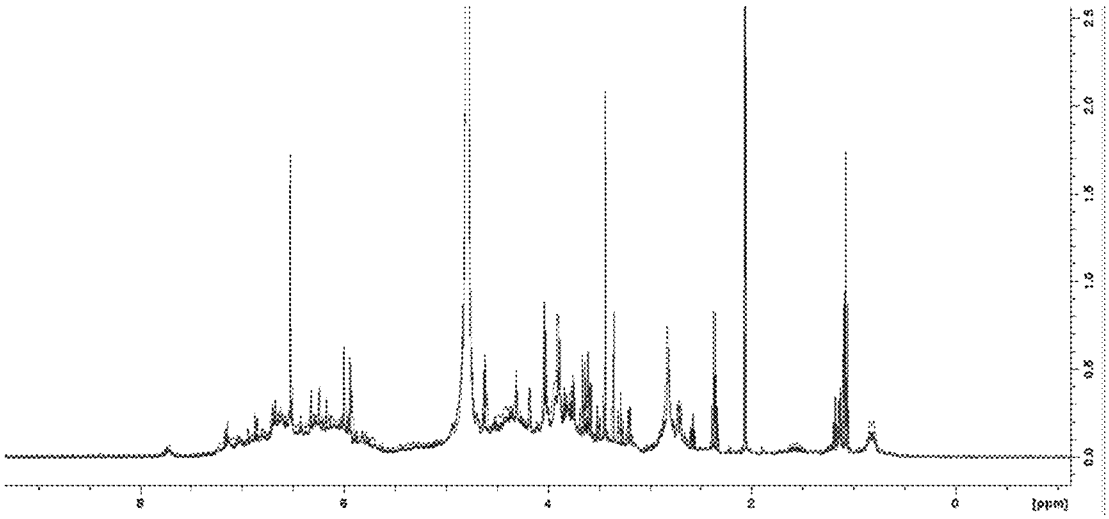
FIG. 2B depicts the overlay of the NMR spectra of Lots 00, 01, and 02 of AB-101 in $D_2O$.
Figure 3A:
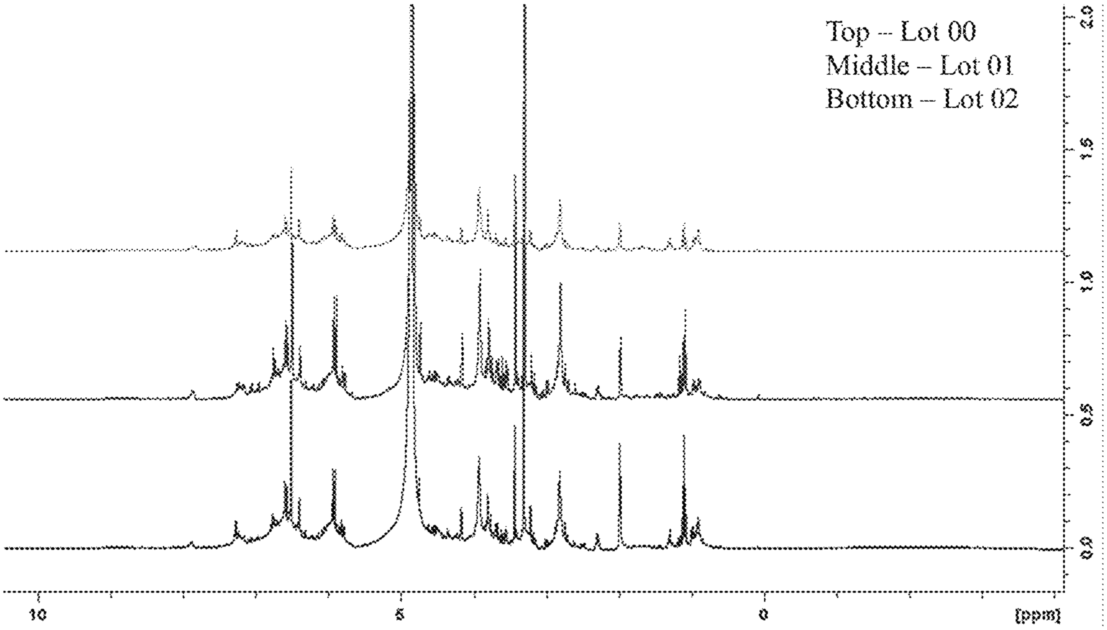
FIG. 3A depicts the Nuclear Magnetic Resonance (NMR) spectra of 3 lots of AB-101 in $d_4$-Methanol—the top spectra is for Lot 00, the middle spectra is for Lot 01, and the bottom spectra is for Lot 02.
Figure 3B:
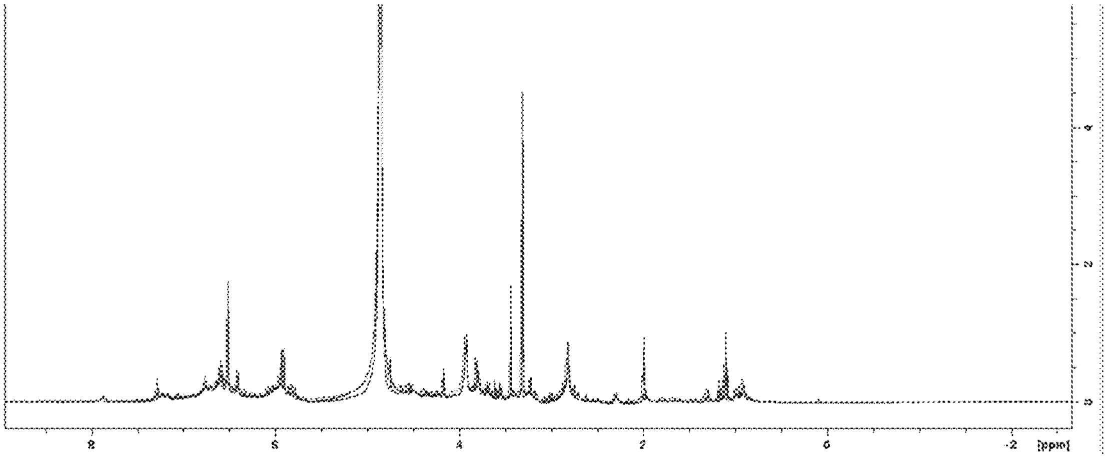
FIG. 3B depicts the overlay of the NMR spectra of Lots 00, 01, and 02 of AB-101 in $d_4$-Methanol.

Biodiversity contributes to vast amounts of variability. In order to capture this variability, an NMR method utilizing a "spectral fingerprint" was used with an overlapping a reference standard. These fingerprinting captures most components within AB-101 and would be quantifiable using Nuclear Magnetic Resonance (NMR). Examples of NMR spectra using three different AB-101 lots (Lots 00, 01, and 02 respectively) and two different deuterated solvents ($D_2O$ and $d_4$-Methanol respectively) are shown in FIGS. 2A and 3A with overlays of each solvents spectra being shown in FIGS. 2B and 3B and demonstrated no significant variability.

Figure 4A:
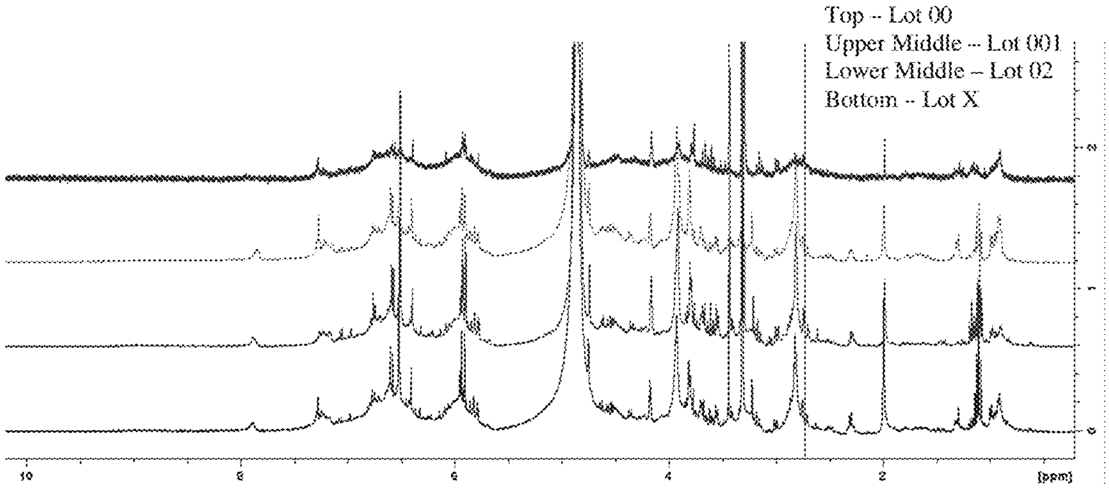
FIG. 4A depicts the NMR spectra of 4 lots of AB-101 in $d_4$-Methanol—the top spectra is for Lot 00, the upper middle spectra is for Lot 01, the lower middle is for Lot 02, and the bottom spectra is for Lot X.
Figure 4B:
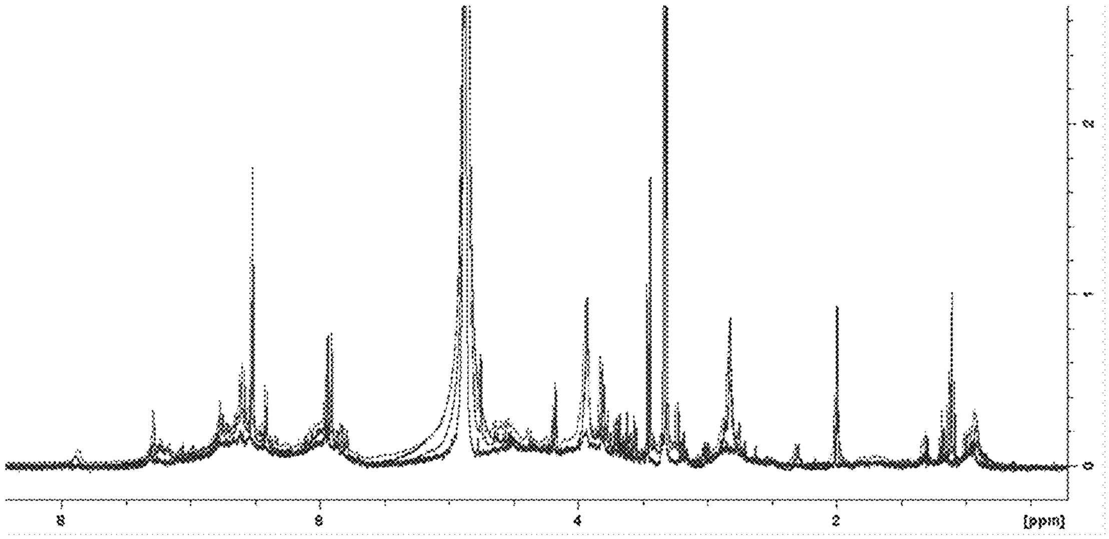
FIG. 4B depicts the overlay of the NMR spectra of Lots 00, 01, 02, and X of AB-101 in $d_4$-Methanol.
Figure 5:
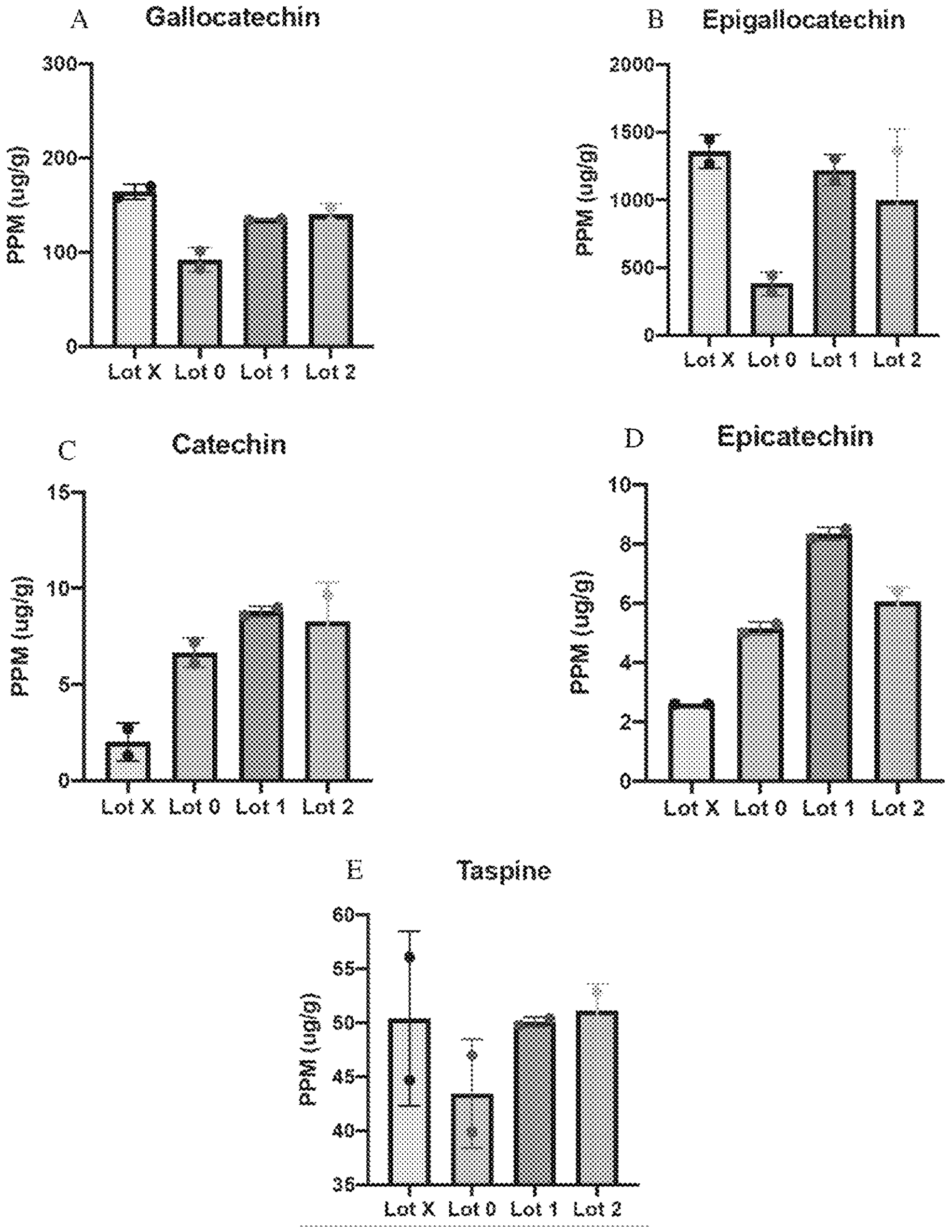
FIG. 5 depicts bar graphs comparing the AB-101 lot analysis results for A) gallocatechin B) epigallocatechin C) catechin D) epicatechin and E) taspine.

In another NMR analysis using the $d_4$-Methanol as the solvent, 4 distinct lots of AB-101 (Lots 00, 01, 02, and X respectively) are compared. NMR spectra of each lot are shown in FIG. 4A with overlays of each lots spectra being shown in FIG. 4B. While the fingerprint of the 4 lots looks similar, there are important differences. This is shown by comparing the concentration level in ppm based on LC-MS/MS Quantification and qualitative NMR "fingerprinting" on the marker compounds of catechin, epicatechin, gallocatechin, epigallocatechin, taspine, and dimethylcedrusin. The results are shown in Table 2 and indicate that lots 1 and 2 are more similar and lots X and 0 have the largest differences.

TABLE 2

| | AB-101 Lots Characterization PPM (μg/g) | | | |
|---|---|---|---|---|
| Lot | X | 00 | 01 | 02 |
| Gallocatechin (GC) | 164.2 | 91.9 | 135.0 | 139.9 |
| Epigallocatechin (EGC) | 1357.6 | 380.7 | 1219.5 | 996.3 |
| Catechin (C) | 2.0 | 6.7 | 8.8 | 8.2 |
| Epicatechin (EC) | 2.6 | 5.2 | 8.3 | 6.1 |
| Taspine (T) | 50.4 | 43.4 | 50.1 | 51.1 |
| Dimethylcedrusin | 0.1 | 0.1 | 0.1 | 0.1 |

FIG. 5A-E depicts bar graphs comparing the AB-101 lot analysis results for each of the 5 marker compounds.

Lot 00 is an example of a lot that is not suitable for use in the pharmaceutical compositions and the methods of use described herein. Lots X, 01 and 02 are examples of lots that are suitable for use in the pharmaceutical compositions and the methods of use described herein.

Zheng-Ping Chen publication (Studies on the Anti-Tumour, Anti-Bacterial and Wound-Healing Properties of Dragon's Blood, Planta Med. 60 (1994)) demonstrates the non-obviousness of identifying the optimum properties of pharmaceutical grade AB-101. Chen uses a bioassay used to measure the incorporation rate of H-thymidine into the DNA of the cells in the presence of the test sample. This bioassay provides a measure of the wound healing property of the "sap." Chen uses the *Croton lechleri* MÜll. Arg latex from Ecuador. This assay indicated that the dried sap and MeOH Extract would have an incorporation rate of 68+/−12 and 88+/−5. According to Chen the dried sap and MeOH was found to be very inhibitory to wound healing properties. One familiar in the art would not assume that a *Croton lechleri* MÜll. Arg latex extract as a whole would be effective in wound healing properties. Further, Chen states that the Ecuador sap contained only traces of taspine. Chen wanted to completely minimize or eliminate taspine due to the concern of being cytotoxin. Chen evaluated specific compound through extraction. Specifically, in the case of gallocatechin and epigalocatechin were rated as slightly stimulating to cell proliferation, while Catechin and Epicatechin showed little effect. Further Chen states that taspine and dimethylcedrusin showed little healing effects in the Ecuadorian sap.

The pharmaceutical grade of AB-101 identified a unique composition to maximize the healing properties while maintaining the film forming, low Log P and antibiotic activity. While Chen would not use the whole *Croton lechleri* Müll. Arg latex containing taspine or dimethylcedrusin, AB-101 pharmaceutical grade maintained using the entire *Croton lechleri* Müll. Arg latex in the composition for medicinal benefits associated with a topical wound healing benefits. Taspine has antibiotic, antiviral and anti-inflammatory properties. Dimethylcedrusin has unique fibroblast stimulating properties to promote healing. Taspine was targeted at least about 45 PPM and dimethylcedrusin was targeted to have a detectable presence be at least about 0.1 PPM. gallocatechin and epigallocatechin were optimized to have a combined total composition of at least about 60% of the total 4 catechins where epigallocatechin was to have a composition at least about 45% of the total 4 catechins.

In some embodiments the latex of *Croton lechleri*, preferably filtered latex of *Croton lechleri*, preferably filtered latex of *Croton lechleri* Müll. Arg. has a minimum bactericidal concentration (MBC) of about 6.25(% vol./vol.), about 12.5(% vol./vol.), about 25(% vol./vol.), about 50(% vol./vol.), or a range between any two of these values. In some embodiments the latex of *Croton lechleri*, preferably filtered latex of *Croton lechleri*, preferably filtered latex of *Croton lechleri* Müll. Arg. has a MBC of about 6.25(% vol./vol.) to about 50(% vol./vol.).

Some embodiments herein are directed to a pharmaceutical composition that further comprises one or more other therapeutic ingredients. In embodiments, the pharmaceutical composition comprises a therapeutically effective amount of the latex of *Croton lechleri*, preferably filtered latex of *Croton lechleri*, preferably filtered latex of *Croton lechleri* Müll. Arg. In embodiments, the pharmaceutical composition is suitable for topical administration or is a topical pharmaceutical composition.

The excipient(s) must be "acceptable" in the sense of being compatible with the other ingredients of the formulation and not deleterious to the recipient thereof. The excipient(s) will utilize a low number of known, well-characterized excipient ingredients that will not impart irritation or sensitization when used topically or in wounds or reduce the efficacy of AB-101. Proper formulation of the pharmaceutical composition is dependent upon the route of administration chosen. Any of the well-known techniques and excipients may be used as suitable and as understood in the art. The pharmaceutical compositions disclosed herein may be manufactured in any manner known in the art.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose, including eutectic solvents, eutectic-based ionic liquids, or ionic liquids. The pharmaceutical compositions can additionally include: lubricating agents such as talc, magnesium stearate, and mineral oil; wetting agents; emulsifying and suspending agents; preserving agents such as methyl- and propylhydroxy-benzoates.

The compositions include those suitable for topical (including, for example, dermal, oral mucosa, buccal, sublingual, intraocular, and wound cavity) or nasal (via, for example, inhalation and/or spray) although the most suitable route may depend upon for example the condition and disorder of the recipient. The compositions may conveniently be presented in unit dosage form and may be prepared by any of the methods well known in the art of pharmacy. Typically, these methods include the step of bringing into association latex of *Croton lechleri*, preferably filtered latex of *Croton lechleri*, preferably filtered latex of *Croton lechleri* Müll. Arg. wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard, disclosed herein ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired composition.

The pharmaceutical compositions disclosed herein may be administered topically, that is by non-systemic administration. This includes the application of a compound disclosed herein externally to the surface of the skin and/or to the wound cavity and to achieve therapeutically effective amounts in the skin, such as the epidermis, dermis, and/or wound cavity. In embodiments, topical administration or a topical pharmaceutical composition does not result in systemic administration or systemic exposure of the *Croton lechleri* to the patient.

In some embodiments, pharmaceutical compositions suitable for topical administration include liquid or semi-liquid preparations suitable for penetration through the skin to the site of inflammation such as a solution, powder, fluid emulsion, fluid suspension, semi-solid, liquid, ointment, paste, hydrogel, cream, gel, jelly, foam, liniment, lotion, drops, aerosols, and sprays.

Lotions include those suitable for application to the skin. Lotions or liniments for application to the skin may also include an agent to hasten drying and to cool the skin, such as an alcohol or acetone, and/or a moisturizer such as glycerol or an oil such as castor oil or *arachis* oil.

Creams, ointments or pastes are semi-solid pharmaceutical compositions of the active ingredient for external application. They may be made by mixing the active ingredient in finely-divided or powdered form, alone or in solution or suspension in an aqueous or non-aqueous fluid, with the aid of suitable machinery, with a greasy or non-greasy base.

Preferred unit dosage pharmaceutical compositions are those containing an effective dose, as herein below recited, or an appropriate fraction thereof, of the active ingredient.

When employed as pharmaceuticals, the compounds can be administered in the form of pharmaceutical compositions. These compositions can be prepared in a manner well known in the pharmaceutical arts, and can be administered by a variety of routes, depending upon whether local or systemic treatment is desired and upon the area to be treated. Administration of the disclosed compounds or compositions may be topical (including dermal, oral mucosa, buccal, sublingual, intraocular, and wound cavity) or nasal (via, for example, inhalation and/or spray). Pharmaceutical compositions for topical administration may include foams, transdermal patches, ointments, lotions, creams, gels, hydrogels, solutions, fluid emulsions, fluid suspensions, semi-solids, pastes, drops, suppositories, aerosols, sprays, liquids, aerosolization, inhalers, and powders. Conventional pharmaceutical carriers, aqueous, powder or oily bases, thickeners and the like may be necessary or desirable. In some embodiments, the compounds can be contained in such pharmaceutical compositions with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The artisan can refer to various pharmacologic references for guidance.

In certain embodiments, the pharmaceutical composition is not a soap.

In certain embodiments, the pharmaceutical composition is a liquid, powder, ointment, lotion, hydrogel, or cream.

In some embodiments, active pharmaceutical compositions comprising latex of *Croton lechleri*, preferably filtered latex of *Croton lechleri*, preferably filtered latex of *Croton lechleri* Müll. Arg. wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard, can be formulated for nasal and/or nasal inhalation.

The pharmaceutical compositions can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active pharmaceutical compositions comprising latex of *Croton lechleri*, preferably filtered latex of *Croton lechleri*, preferably filtered latex of *Croton lechleri* Müll. Arg., wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard, can be effective over a wide dosage range and can be generally administered in a therapeutically effective amount. It will be understood, however, that the amount of the pharmaceutical compositions comprising latex of *Croton lechleri*, preferably filtered latex of *Croton lechleri*, preferably filtered latex of *Croton lechleri* Müll. Arg., wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard, actually administered will usually be determined by a physician, according to the relevant circumstances, including the condition to be treated, the chosen route of administration, the actual compound administered, the age, weight, and response of the individual patient, the severity of the patient's symptoms, and the like.

The pharmaceutically acceptable excipient may be selected from one or more cream bases, one or more emulsifying agents, one or more preservatives, one or more humectants, one or more diluents, and latex of *Croton lechleri*, preferably filtered latex of *Croton lechleri*, preferably filtered latex of *Croton lechleri* Müll. Arg.

In some embodiments, the pharmaceutical composition may comprise about 0.1 wt % to about 60 wt % of latex of *Croton lechleri*, preferably filtered latex of *Croton lechleri*, preferably filtered latex of *Croton lechleri* Müll. Arg. wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard, disclosed herein. In some embodiments, the latex of *Croton lechleri*, preferably filtered latex of *Croton lechleri*, preferably filtered latex of *Croton lechleri* Müll.

Arg. wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard is in an amount of about 0.1 wt % to about 99 wt %, about 0.1 wt % to about 98 wt %, about 0.1 wt % to about 97 wt %, about 0.1 wt % to about 96 wt %, about 0.1 wt % to about 95 wt %, about 0.1 wt % to about 90 wt %, about 0.1 wt % to about 85 wt %, about 0.1 wt % to about 80 wt %, about 0.1 wt % to about 75 wt %, about 0.1 wt % to about 70 wt %, about 0.1 wt % to about 65 wt %, about 0.1 wt % to about 55 wt %, about 0.1 wt % to about 50 wt %, about 0.1 wt % to about 45 wt %, about 0.1 wt % to about 40 wt %, about 0.1 wt % to about 30 wt %, about 0.1 wt % to about 20 wt %, about 0.1 wt % to about 10 wt %, about 0.1 wt % to about 5 wt %, about 0.5 wt % to about 50 wt %, about 0.5 wt % to about 45 wt %, about 0.5 wt % to about 40 wt %, about 0.5 wt % to about 30 wt %, about 0.5 wt % to about 20 wt %, about 0.5 wt % to about 10 wt %, about 0.5 wt % to about 5 wt %, about 1 wt % to about 300 wt %, about 1 wt % to about 295 wt %, about 1 wt % to about 290 wt %, about 1 wt % to about 285 wt %, about 1 wt % to about 280 wt %, about 1 wt % to about 275 wt %, about 1 wt % to about 270 wt %, about 1 wt % to about 265 wt %, about 1 wt % to about 260 wt %, about 1 wt % to about 255 wt %, about 1 wt % to about 250 wt %, about 1 wt % to about 245 wt %, about 1 wt % to about 240 wt %, about 1 wt % to about 235 wt %, about 1 wt % to about 230 wt %, about 1 wt % to about 225 wt %, about 1 wt % to about 220 wt %, about 1 wt % to about 215 wt %, about 1 wt % to about 210 wt %, about 1 wt % to about 205 wt %, about 1 wt % to about 200 wt %, 195 wt %, about 1 wt % to about 190 wt %, about 1 wt % to about 185 wt %, about 1 wt % to about 180 wt %, about 1 wt % to about 175 wt %, about 1 wt % to about 170 wt %, about 1 wt % to about 165 wt %, about 1 wt % to about 160 wt %, about 1 wt % to about 155 wt %, about 1 wt % to about 150 wt %, about 1 wt % to about 145 wt %, about 1 wt % to about 140 wt %, about 1 wt % to about 135 wt %, about 1 wt % to about 130 wt %, about 1 wt % to about 125 wt %, about 1 wt % to about 120 wt %, about 1 wt % to about 115 wt %, about 1 wt % to about 110 wt %, about 1 wt % to about 105 wt %, about 1 wt % to about 100 wt %, about 1 wt % to about 95 wt %, about 1 wt % to about 90 wt %, about 1 wt % to about 85 wt %, about 1 wt % to about 80 wt %, about 1 wt % to about 75 wt %, about 1 wt % to about 70 wt %, about 1 wt % to about 65 wt %, about 1 wt % to about 60 wt %, about 1 wt % to about 55 wt %, about 1 wt % to about 50 wt %, about 1 wt % to about 45 wt %, about 1 wt % to about 40 wt %, about 1 wt % to about 35 wt %, about 1 wt % to about 30 wt %, about 1 wt % to about 25 wt %, about 1 wt % to about 20 wt %, about 1 wt % to about 15 wt %, about 1 wt % to about 10 wt %, about 1 wt % to about 5 wt %, about 5 wt % to about 45 wt %, about 5 wt % to about 40 wt %, about 5 wt % to about 35 wt %, about 5 wt % to about 30 wt %, about 5 wt % to about 25 wt %, about 5 wt % to about 20 wt %, about 5 wt % to about 15 wt %, about 5 wt % to about 10 wt %, about 2 wt % to about 300 wt %, about 2 wt % to about 295 wt %, about 2 wt % to about 290 wt %, about 2 wt % to about 285 wt %, about 2 wt % to about 280 wt %, about 2 wt % to about 275 wt %, about 2 wt % to about 270 wt %, about 2 wt % to about 265 wt %, about 2 wt % to about 260 wt %, about 2 wt % to about 255 wt %, about 2 wt % to about 250 wt %, about 2 wt % to about 245 wt %, about 2 wt % to about 240 wt %, about 2 wt % to about 235 wt %, about 2 wt % to about 230 wt %, about 2 wt % to about 225 wt %, about 2 wt % to about 220 wt %, about 2 wt % to about 215 wt %, about 2 wt % to about 210 wt %, about 2 wt % to about 205 wt %, about 2 wt % to about 200 wt %, 195 wt %, about 2 wt % to about 190 wt %, about 2 wt % to about 185 wt %, about 2 wt % to about 180 wt %, about 2 wt % to about 175 wt %, about 2 wt % to about 170 wt %, about 2 wt % to about 165 wt %, about 2 wt % to about 160 wt %, about 2 wt % to about 155 wt %, about 2 wt % to about 150 wt %, about 2 wt % to about 145 wt %, about 2 wt % to about 140 wt %, about 2 wt % to about 135 wt %, about 2 wt % to about 130 wt %, about 2 wt % to about 125 wt %, about 2 wt % to about 120 wt %, about 2 wt % to about 115 wt %, about 2 wt % to about 110 wt %, about 2 wt % to about 105 wt %, about 2 wt % to about 100 wt %, about 2 wt % to about 95 wt %, about 2 wt % to about 90 wt %, about 2 wt % to about 85 wt %, about 2 wt % to about 80 wt %, about 2 wt % to about 75 wt %, about 2 wt % to about 70 wt %, about 2 wt % to about 65 wt %, about 2 wt % to about 60 wt %, about 2 wt % to about 55 wt %, about 2 wt % to about 50 wt %, about 2 wt % to about 45 wt %, about 2 wt % to about 40 wt %, about 2 wt % to about 35 wt %, about 2 wt % to about 30 wt %, about 2 wt % to about 25 wt %, about 2 wt % to about 20 wt %, about 2 wt % to about 15 wt %, about 3 wt % to about 300 wt %, about 3 wt % to about 295 wt %, about 3 wt % to about 290 wt %, about 3 wt % to about 285 wt %, about 3 wt % to about 280 wt %, about 3 wt % to about 275 wt %, about 3 wt % to about 270 wt %, about 3 wt % to about 265 wt %, about 3 wt % to about 260 wt %, about 3 wt % to about 255 wt %, about 3 wt % to about 250 wt %, about 3 wt % to about 245 wt %, about 3 wt % to about 240 wt %, about 3 wt % to about 235 wt %, about 3 wt % to about 230 wt %, about 3 wt % to about 225 wt %, about 3 wt % to about 220 wt %, about 3 wt % to about 215 wt %, about 3 wt % to about 210 wt %, about 3 wt % to about 205 wt %, about 3 wt % to about 200 wt %, 195 wt %, about 3 wt % to about 190 wt %, about 3 wt % to about 185 wt %, about 3 wt % to about 180 wt %, about 3 wt % to about 175 wt %, about 3 wt % to about 170 wt %, about 3 wt % to about 165 wt %, about 3 wt % to about 160 wt %, about 3 wt % to about 155 wt %, about 3 wt % to about 150 wt %, about 3 wt % to about 145 wt %, about 3 wt % to about 140 wt %, about 3 wt % to about 135 wt %, about 3 wt % to about 130 wt %, about 3 wt % to about 125 wt %, about 3 wt % to about 120 wt %, about 3 wt % to about 115 wt %, about 3 wt % to about 110 wt %, about 3 wt % to about 105 wt %, about 3 wt % to about 100 wt %, about 3 wt % to about 95 wt %, about 3 wt % to about 90 wt %, about 3 wt % to about 85 wt %, about 3 wt % to about 80 wt %, about 3 wt % to about 75 wt %, about 3 wt % to about 70 wt %, about 3 wt % to about 65 wt %, about 3 wt % to about 60 wt %, about 3 wt % to about 55 wt %, about 3 wt % to about 50 wt %, about 3 wt % to about 45 wt %, about 3 wt % to about 40 wt %, about 3 wt % to about 35 wt %, about 3 wt % to about 30 wt %, about 3 wt % to about 25 wt %, about 3 wt % to about 20 wt %, about 3 wt % to about 15 wt %, about 10 wt % to about 45 wt %, about 10 wt % to about 40 wt %, about 10 wt % to about 35 wt %, about 10 wt % to about 30 wt %, about 10 wt % to about 25 wt %, about 10 wt % to about 20 wt %, about 10 wt % to about 15 wt %, or a value within one of these ranges. Specific examples may include about 0.01 wt %, about 0.05 wt %, about 0.1 wt %, about 0.25 wt %, about 0.5 wt %, about 0.75 wt %, about 1 wt %, about 5 wt %, about 10 wt %, about 15 wt %, about 20 wt %, about 25 wt %, about 30 wt %, about 35 wt %, about 40 wt %, about 45 wt %, about 50 wt %, about 60 wt %, about 70 wt %, about 80 wt %, about 90 wt %, about 100 wt %, about 110 wt %, about 120 wt %, about 130 wt %, about 140 wt %, about 150 wt %, about 160 wt %, about 170 wt %, about 180 wt %, about 190 wt %, about 200 wt %, about 210 wt %, about 220 wt %, about 230 wt %, about 240 wt %, about 250 wt %, about 260 wt %, about 270 wt %, about 280 wt %, about 290 wt %, about 300 wt %, or a range between any two of these values. The forgoing percentages are relative to a composition made from AB-101 with exemplary amounts of the marker compounds present in the latex as disclosed in Table 1a. To illustrate, a pharmaceutical composition comprising 100 wt % of AB-101 will contain at least about 110 PPM of gallocatechin, while a pharmaceutical composition comprising 200 wt % of AB-101 will contain at least about 220 PPM of gallocatechin. The foregoing all representing weight percentages of embodiments of the pharmaceutical compositions. In some embodiments, the pharmaceutical composition is suitable for topical administration (including, for example, dermal, oral mucosa, buccal, sublingual intraocular, and wound cavity) or nasal administration (via, for example, inhalation and/or spray).

In some embodiments, the latex of *Croton lechleri*, preferably filtered latex of *Croton lechleri*, preferably filtered latex of *Croton lechleri* Müll. Arg. wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard, is in a therapeutically effective amount. In some embodiments, the therapeutically effective amount may be in an amount of about 0.1 wt % to about 100 wt %, about 0.1 wt % to about 95 wt %, about 0.1 wt % to about 90 wt %, about 0.1 wt % to about 85 wt %, about 0.1 wt % to about 80 wt %, about 0.1 wt % to about 75 wt %, about 0.1 wt % to about 70 wt %, about 0.1 wt % to about 65 wt %, about 0.1 wt % to about 60 wt %, about 0.1 wt % to about 55 wt %, about 0.1 wt % to about 50 wt %, about 0.1 wt % to about 45 wt %, about 0.1 wt % to about 40 wt %, about 0.1 wt % to about 30 wt %, about 0.1 wt % to about 20 wt %, about 0.1 wt % to about 10 wt %, about 0.1 wt % to about 5 wt %, about 0.5 wt % to about 50 wt %, about 0.5 wt % to about 45 wt %, about 0.5 wt % to about 40 wt %, about 0.5 wt % to about 30 wt %, about 0.5 wt % to about 20 wt %, about 0.5 wt % to about 10 wt %, about 0.5 wt % to about 5 wt %, about 1 wt % to about 300 wt %, about 1 wt % to about 295 wt %, about 1 wt % to about 290 wt %, about 1 wt % to about 285 wt %, about 1 wt % to about 280 wt %, about 1 wt % to about 275 wt %, about 1 wt % to about 270 wt %, about 1 wt % to about 265 wt %, about 1 wt % to about 260 wt %, about 1 wt % to about 255 wt %, about 1 wt % to about 250 wt %, about 1 wt % to about 245 wt %, about 1 wt % to about 240 wt %, about 1 wt % to about 235 wt %, about 1 wt % to about 230 wt %, about 1 wt % to about 225 wt %, about 1 wt % to about 220 wt %, about 1 wt % to about 215 wt %, about 1 wt % to about 210 wt %, about 1 wt % to about 205 wt %, about 1 wt % to about 200 wt %, 195 wt %, about 1 wt % to about 190 wt %, about 1 wt % to about 185 wt %, about 1 wt % to about 180 wt %, about 1 wt % to about 175 wt %, about 1 wt % to about 170 wt %, about 1 wt % to about 165 wt %, about 1 wt % to about 160 wt %, about 1 wt % to about 155 wt %, about 1 wt % to about 150 wt %, about 1 wt % to about 145 wt %, about 1 wt % to about 140 wt %, about 1 wt % to about 135 wt %, about 1 wt % to about 130 wt %, about 1 wt % to about 125 wt %, about 1 wt % to about 120 wt %, about 1 wt % to about 115 wt %, about 1 wt % to about 110 wt %, about 1 wt % to about 105 wt %, about 1 wt % to about 100 wt %, about 1 wt % to about 95 wt %, about 1 wt % to about 90 wt %, about 1 wt % to about 85 wt %, about 1 wt % to about 80 wt %, about 1 wt % to about 75 wt %, about 1 wt % to about 70 wt %, about 1 wt % to about 65 wt %, about 1 wt % to about 60 wt %, about 1 wt % to about 55 wt %, about 1 wt % to about 50 wt %, about 1 wt % to about 45 wt %, about 1 wt % to about 40 wt %, about 1 wt % to about 35 wt %, about 1 wt % to about 30 wt %, about 1 wt % to about 25 wt %, about 1 wt % to about 20 wt %, about 1 wt % to about 15 wt %, about 1 wt % to about 10 wt %, about 1 wt % to about 5 wt %, about 5 wt % to about 45 wt %, about 5 wt % to about 40 wt %, about 5 wt % to about 35 wt %, about 5 wt % to about 30 wt %, about 5 wt % to about 25 wt %, about 5 wt % to about 20 wt %, about 5 wt % to about 15 wt %, about 5 wt % to about 10 wt %, about 2 wt % to about 300 wt %, about 2 wt % to about 295 wt %, about 2 wt % to about 290 wt %, about 2 wt % to about 285 wt %, about 2 wt % to about 280 wt %, about 2 wt % to about 275 wt %, about 2 wt % to about 270 wt %, about 2 wt % to about 265 wt %, about 2 wt % to about 260 wt %, about 2 wt % to about 255 wt %, about 2 wt % to about 250 wt %, about 2 wt % to about 245 wt %, about 2 wt % to about 240 wt %, about 2 wt % to about 235 wt %, about 2 wt % to about 230 wt %, about 2 wt % to about 225 wt %, about 2 wt % to about 220 wt %, about 2 wt % to about 215 wt %, about 2 wt % to about 210 wt %, about 2 wt % to about 205 wt %, about 2 wt % to about 200 wt %, 195 wt %, about 2 wt % to about 190 wt %, about 2 wt % to about 185 wt %, about 2 wt % to about 180 wt %, about 2 wt % to about 175 wt %, about 2 wt % to about 170 wt %, about 2 wt % to about 165 wt %, about 2 wt % to about 160 wt %, about 2 wt % to about 155 wt %, about 2 wt % to about 150 wt %, about 2 wt % to about 145 wt %, about 2 wt % to about 140 wt %, about 2 wt % to about 135 wt %, about 2 wt % to about 130 wt %, about 2 wt % to about 125 wt %, about 2 wt % to about 120 wt %, about 2 wt % to about 115 wt %, about 2 wt % to about 110 wt %, about 2 wt % to about 105 wt %, about 2 wt % to about 100 wt %, about 2 wt % to about 95 wt %, about 2 wt % to about 90 wt %, about 2 wt % to about 85 wt %, about 2 wt % to about 80 wt %, about 2 wt % to about 75 wt %, about 2 wt % to about 70 wt %, about 2 wt % to about 65 wt %, about 2 wt % to about 60 wt %, about 2 wt % to about 55 wt %, about 2 wt % to about 50 wt %, about 2 wt % to about 45 wt %, about 2 wt % to about 40 wt %, about 2 wt % to about 35 wt %, about 2 wt % to about 30 wt %, about 2 wt % to about 25 wt %, about 2 wt % to about 20 wt %, about 2 wt % to about 15 wt %, about 3 wt % to about 300 wt %, about 3 wt % to about 295 wt %, about 3 wt % to about 290 wt %, about 3 wt % to about 285 wt %, about 3 wt % to about 280 wt %, about 3 wt % to about 275 wt %, about 3 wt % to about 270 wt %, about 3 wt % to about 265 wt %, about 3 wt % to about 260 wt %, about 3 wt % to about 255 wt %, about 3 wt % to about 250 wt %, about 3 wt % to about 245 wt %, about 3 wt % to about 240 wt %, about 3 wt % to about 235 wt %, about 3 wt % to about 230 wt %, about 3 wt % to about 225 wt %, about 3 wt % to about 220 wt %, about 3 wt % to about 215 wt %, about 3 wt % to about 210 wt %, about 3 wt % to about 205 wt %, about 3 wt % to about 200 wt %, 195 wt %, about 3 wt % to about 190 wt %, about 3 wt % to about 185 wt %, about 3 wt % to about 180 wt %, about 3 wt % to about 175 wt %, about 3 wt % to about 170 wt %, about 3 wt % to about 165 wt %, about 3 wt % to about 160 wt %, about 3 wt % to about 155 wt %, about 3 wt % to about 150 wt %, about 3 wt % to about 145 wt %, about 3 wt % to about 140 wt %, about 3 wt % to about 135 wt %, about 3 wt % to about 130 wt %, about 3 wt % to about 125 wt %, about 3 wt % to about 120 wt %, about 3 wt % to about 115 wt %, about 3 wt % to about 110 wt %, about 3 wt % to about 105 wt %, about 3 wt % to about 100 wt %, about 3 wt % to about 95 wt %, about 3 wt % to about 90 wt %, about 3 wt % to about 85 wt %, about 3 wt % to about 80 wt %, about 3 wt % to about 75 wt %, about 3 wt % to about 70 wt %, about 3 wt % to about 65 wt %, about 3 wt % to about 60 wt %, about 3 wt % to about 55 wt %, about 3 wt % to about 50 wt %, about 3 wt % to about 45 wt %, about 3 wt % to about 40 wt %, about 3 wt % to about 35 wt %, about 3 wt % to about 30 wt %, about 3 wt % to about 25 wt %, about 3 wt % to about 20 wt %, about 3 wt % to about 15 wt %, about 5 wt % to about 100 wt %, about 5 wt % to about 95 wt %, about 5 wt % to about 90 wt %, about 5 wt % to about 85 wt %, about 5 wt % to about 80 wt %, about 5 wt % to about 75 wt %, about 5 wt % to about 70 wt %, about 5 wt % to about 65 wt %, about 5 wt % to about 60 wt %, about 5 wt % to about 55 wt %, about 5 wt % to about 50 wt %, about 5 wt % to about 45 wt %, about 5 wt % to about 40 wt %, about 5 wt % to about 35 wt %, about 5 wt % to about 30 wt %, about 5 wt % to about 25 wt %, about 5 wt % to about 20 wt %, about 5 wt % to about 15 wt %, about 5 wt % to about 10 wt %, about 10 wt % to about 100 wt %, about 10 wt % to about 95 wt %, about 10 wt % to about 90 wt %, about 10 wt % to about 85 wt %, about 10 wt % to about 80 wt %, about 10 wt % to about 75 wt %, about 10 wt % to about 70 wt %, about 10 wt % to about 65 wt %, about 10 wt % to about 60 wt %, about 10 wt % to about 55 wt %, about 10 wt % to about 50 wt %, about 10 wt % to about 45 wt %, about 10 wt % to about 40 wt %, about 10 wt % to about 35 wt %, about 10 wt % to about 30 wt %, about 10 wt % to about 25 wt %, about 10 wt % to about 20 wt %, about 10 wt % to about 15 wt %, or a value within one of these ranges. Specific examples may include about about 0.1 wt %, about 0.25 wt %, about 0.5 wt %, about 0.75 wt %, about 1 wt %, about 3 wt %, about 5 wt %, about 10 wt %, about 15 wt %, about 20 wt %, about 25 wt %, about 30 wt %, about 35 wt %, about 40 wt %, about 45 wt %, about 50 wt %, about 60 wt %, about 70 wt %, about 80 wt %, about 90 wt %, about 100 wt %, about 110 wt %, about 120 wt %, about 130 wt %, about 140 wt %, about 150 wt %, about 160 wt %, about 170 wt %, about 180 wt %, about 190 wt %, about 200 wt %, about 210 wt %, about 220 wt %, about 230 wt %, about 240 wt %, about 250 wt %, about 260 wt %, about 270 wt %, about 280 wt %, about 290 wt %, about 300 wt %, or a range between any two of these values. In some embodiments, the therapeutically effective amount may be in an amount of about 3 wt % to about 90 wt %. The forgoing percentages are relative to a composition made from AB-101 with exemplary amounts of the marker compounds present in the latex as disclosed in Table 1a. To illustrate, a therapeutically effective amount in the amount of 100 wt % of AB-101 will contain at least about 110 PPM of gallocatechin, while a therapeutically effective amount in the amount of 200 wt % of AB-101 will contain at least about 220 PPM of gallocatechin. The foregoing all representing weight percentages of the pharmaceutical composition.

In some embodiments, the therapeutically effective amount can vary according to, for example, the particular use for which the treatment is made, the manner of administration of the compound, the health and condition of the patient, and the judgment of the prescribing physician. The proportion or concentration of latex of *Croton lechleri*, preferably filtered latex of *Croton lechleri*, preferably filtered latex of *Croton lechleri* Müll. Arg., wherein the composition contains at least the concentration of components of latex of *Croton lechleri*, preferably the concentration of components of filtered latex of *Croton lechleri*, preferably the concentration of components of filtered latex of *Croton lechleri* Müll. Arg of the reference standard, in a pharmaceutical composition can vary depending upon a number of factors including dosage, chemical characteristics (e.g., hydrophobicity), and the route of administration. For example, the compounds can be provided in an aqueous physiological buffer solution containing about 0.1 to about 10% w/v of the compound for parenteral administration. Some typical dose ranges for the compounds are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, composition of the excipient, and its route of administration. Effective doses can be extrapolated from dose-response curves derived from in vitro or animal model test systems.

The amount of composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications.

In certain embodiments the one or more cream bases is selected from cetyl alcohol, isopropylmeristat, petroleum jelly, or any combination thereof. In some embodiments, the one or more cream bases is in an amount of about 0.01% to about 50%, about 0.01% to about 45%, about 0.01% to about 40%, about 0.01% to about 30%, about 0.01% to about 20%, about 0.01% to about 10%, about 0.01% to about 5%, about 0.05% to about 50%, about 0.05% to about 45%, about 0.05% to about 40%, about 0.05% to about 30%, about 0.05% to about 20%, about 0.05% to about 10%, about 0.1% to about 50%, about 0.1% to about 45%, about 0.1% to about 40%, about 0.1% to about 30%, about 0.1% to about 20%, about 0.1% to about 10%, about 0.1% to about 5%, about 0.5% to about 50%, about 0.5% to about 45%, about 0.5% to about 40%, about 0.5% to about 30%, about 0.5% to about 20%, about 0.5% to about 10%, about 0.5% to about 5%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.01%, about 0.05%, about 0.1%, about 0.25%, about 0.5%, about 0.75%, about 1%, about 5%, about 10%, about 15%, about 20%, about 25%, about 30%, about 35%, about 40%, about 45%, about 50%, about 60%, about 70%, about 80%, about 90%, or a range between any two of these values. The foregoing all representing weight percentages of the pharmaceutical composition. In some embodiments, the pharmaceutical composition is suitable for topical administration (including, for example, dermal, oral mucosa, buccal, sublingual and intraocular) or nasal administration (via, for example, inhalation and/or spray).

In certain embodiments the one or more emulsifying agents is selected from span20, tween 80, or any combination thereof. In some embodiments, the one or more emulsifying agents is in an amount of about 0.01% to about 50%, about 0.01% to about 45%, about 0.01% to about 40%, about 0.01% to about 30%, about 0.01% to about 20%, about 0.01% to about 10%, about 0.01% to about 5%, about 0.05% to about 50%, about 0.05% to about 45%, about 0.05% to about 40%, about 0.05% to about 30%, about 0.05% to about 20%, about 0.05% to about 10%, about 0.1% to about 50%, about 0.1% to about 45%, about 0.1% to about 40%, about 0.1% to about 30%, about 0.1% to about 20%, about 0.1% to about 10%, about 0.1% to about 5%, about 0.5% to about 50%, about 0.5% to about 45%, about 0.5% to about 40%, about 0.5% to about 30%, about 0.5% to about 20%, about 0.5% to about 10%, about 0.5% to about 5%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.01%, about 0.05%, about 0.1%, about 0.25%, about 0.5%, about 0.75%, about 1%, about 5%, about 10%, about 15%, about 20%, about 25%, about 30%, about 35%, about 40%, about 45%, about 50%, about 60%, about 70%, about 80%, about 90%, or a range between any two of these values. The foregoing all representing weight percentages of the pharmaceutical composition. In some embodiments, the pharmaceutical composition is suitable for topical administration (including, for example, dermal, oral mucosa, buccal, sublingual and intraocular) or nasal administration (via, for example, inhalation and/or spray).

In certain embodiments the one or more preservatives is selected from propylparaben, methylparaben, or any combination thereof. In some embodiments, the one or more preservatives is in an amount of about 0.01% to about 50%, about 0.01% to about 45%, about 0.01% to about 40%, about 0.01% to about 30%, about 0.01% to about 20%, about 0.01% to about 10%, about 0.01% to about 5%, about 0.05% to about 50%, about 0.05% to about 45%, about 0.05% to about 40%, about 0.05% to about 30%, about 0.05% to about 20%, about 0.05% to about 10%, about 0.1% to about 50%, about 0.1% to about 45%, about 0.1% to about 40%, about 0.1% to about 30%, about 0.1% to about 20%, about 0.1% to about 10%, about 0.1% to about 5%, about 0.5% to about 50%, about 0.5% to about 45%, about 0.5% to about 40%, about 0.5% to about 30%, about 0.5% to about 20%, about 0.5% to about 10%, about 0.5% to about 5%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.01%, about 0.05%, about 0.1%, about 0.25%, about 0.5%, about 0.75%, about 1%, about 5%, about 10%, about 15%, about 20%, about 25%, about 30%, about 35%, about 40%, about 45%, about 50%, about 60%, about 70%, about 80%, about 90%, or a range between any two of these values. The foregoing all representing weight percentages of the pharmaceutical composition. In some embodiments, the pharmaceutical composition is suitable for topical administration (including, for example, dermal, oral mucosa, buccal, sublingual and intraocular) or nasal administration (via, for example, inhalation and/or spray).

In certain embodiments the one or more humectants is propylene glycol. In some embodiments, the one or more humectants is in an amount of about 0.01% to about 50%, about 0.01% to about 45%, about 0.01% to about 40%, about 0.01% to about 30%, about 0.01% to about 20%, about 0.01% to about 10%, about 0.01% to about 5%, about 0.05% to about 50%, about 0.05% to about 45%, about 0.05% to about 40%, about 0.05% to about 30%, about 0.05% to about 20%, about 0.05% to about 10%, about 0.1% to about 50%, about 0.1% to about 45%, about 0.1% to about 40%, about 0.1% to about 30%, about 0.1% to about 20%, about 0.1% to about 10%, about 0.1% to about 5%, about 0.5% to about 50%, about 0.5% to about 45%, about 0.5% to about 40%, about 0.5% to about 30%, about 0.5% to about 20%, about 0.5% to about 10%, about 0.5% to about 5%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 45%, about 5% to about 40%, about 5% to about 35%, about 5% to about 30%, about 5% to about 25%, about 5% to about 20%, about 5% to about 15%, about 5% to about 10%, about 10% to about 45%, about 10% to about 40%, about 10% to about 35%, about 10% to about 30%, about 10% to about 25%, about 10% to about 20%, about 10% to about 15%, or a value within one of these ranges. Specific examples may include about 0.01%, about 0.05%, about 0.1%, about 0.25%, about 0.5%, about 0.75%, about 1%, about 5%, about 10%, about 15%, about 20%, about 25%, about 30%, about 35%, about 40%, about 45%, about 50%, about 60%, about 70%, about 80%, about 90%, or a range between any two of these values. The foregoing all representing weight percentages of the pharmaceutical composition. In some embodiments, the pharmaceutical composition is suitable for topical administration (including, for example, dermal, oral mucosa, buccal, sublingual and intraocular) or nasal administration (via, for example, inhalation and/or spray).

In certain embodiments the one or more diluents is water. Wherein the one or more diluents is in a quantity sufficient to bring the sum of the component weight percentages of the pharmaceutical composition to 100%.

The one or more ethanolic extracts of *Croton lechleri* is prepared by dissolving the latex of *Croton lechleri*, preferably filtered latex of *Croton lechleri*, preferably filtered latex of *Croton lechleri* Müll. Arg. in ethanol. The latex of *Croton lechleri*, preferably filtered latex of *Croton lechleri*, preferably filtered latex of *Croton lechleri* Müll. Arg. tree is not modified prior to dissolving in ethanol.

In some embodiments, the pharmaceutical composition comprises about 10.0% cetyl alcohol, about 7.0% isopropylmeristat, about 21.0% petroleum jelly, about 1.5% span20, about 1.5% tween 80, about 0.02% propylparaben, about 0.18% methylparaben, about 5% propylene glycol, about 15% one or more ethanolic extracts of *Croton lechleri*, and water in a quantity sufficient to bring the sum of the component weight percentages of the pharmaceutical composition to 100%.

Methods of Use

Secondary bacterial infections or colonizations occur when bacteria infect or colonize diseased skin. The secondary infection may be any infection occurring in skin with an underlying skin disorder. Because of the underlying primary disease, the clinical picture and course of these infections vary. Some bacteria have become resistant to commonly used antibiotics or drugs. Antibiotic or drug resistant bacteria are bacteria that are not controlled or killed by antibiotics or drugs. They are able to survive and even multiply in the presence of an antibiotic or drug. Most infection-causing bacteria can become resistant to at least some antibiotics or drugs. Bacteria that are resistant to many antibiotics are known as multi-resistant organisms (or MRO) or multi-drug resistant organisms (or MDRO). Treating skin infections topically can be a first line of defense to prevent the skin infection from spreading to systemic or internal body infection preventing detrimental and serious health effects including death.

The present invention relates to a method of treatment of a bacterial colonization or primary or secondary bacterial infection of an underlying skin disorder in a subject, comprising the administering to affected areas of the subject a therapeutically effective amount of latex of *Croton lechleri*, preferably filtered latex of *Croton lechleri*, preferably filtered latex of *Croton lechleri* Arg., wherein the therapeutically effective amount contains at least the concentration of components of latex of *Croton lechleri*, preferably the concentration of components of filtered latex of *Croton lechleri*, preferably the concentration of components of filtered latex of *Croton lechleri* Müll. Arg of the reference standard, or a treated bandage comprising a pharmaceutical composition containing latex of *Croton lechleri*, preferably filtered latex of *Croton lechleri*, preferably filtered latex of *Croton lechleri* Müll. Arg., wherein the therapeutically effective amount contains at least the concentration of components of latex of *Croton lechleri*, preferably the concentration of components of filtered latex of *Croton* lechleri, preferably the concentration of components of filtered latex of *Croton lechleri* Müll. Arg of the reference standard, as disclosed herein. In embodiments, the pharmaceutical composition may include a pharmaceutically acceptable excipient.

The present invention relates to methods of treatment of a bacterial colonization or primary or secondary bacterial infection of an underlying skin disorder in a subject comprising the administration of a therapeutically effective amount of latex of *Croton lechleri*, preferably filtered latex of *Croton lechleri*, preferably filtered latex of *Croton lechleri* Müll. Arg. or a pharmaceutical composition containing latex of *Croton lechleri*, preferably filtered latex of *Croton lechleri*, preferably filtered latex of *Croton lechleri* Müll. Arg. as disclosed herein. In embodiments, the pharmaceutical composition may include a pharmaceutically acceptable excipient. As disclosed herein the latex of *Croton lechleri*, preferably filtered latex of *Croton lechleri*, preferably filtered latex of *Croton lechleri* Müll. Arg. shall comprise one or more compounds selected from: gallocatechin, epigallocatechin, catechin, epicatechin, taspine, and dimethycedrusin, and combinations thereof. Each of gallocatechin, epigallocatechin, catechin, epicatechin, taspine, and dimethylcedrusin may be present in the latex of *Croton lechleri*, preferably filtered latex of *Croton lechleri*, preferably filtered latex of *Croton lechleri* Müll. Arg. in the amounts found in Table 1a or paragraphs [0117]-[0122], or any combination of such amounts. In some embodiments latex of *Croton lechleri*, preferably filtered latex of *Croton lechleri*, preferably filtered latex of *Croton lechleri* Müll. Arg. has a PDI of embodiments disclosed herein.

Also provided herein is latex of *Croton lechleri*, preferably filtered latex of *Croton lechleri*, preferably filtered latex of *Croton lechleri* Müll. Arg. as disclosed herein for use as a medicament. In some embodiments latex of *Croton lechleri*, preferably filtered latex of *Croton lechleri*, preferably filtered latex of *Croton lechleri* Müll. Arg. has a PDI of embodiments disclosed herein.

Also provided herein is latex of *Croton lechleri*, preferably filtered latex of *Croton lechleri*, preferably filtered latex of *Croton lechleri* Müll. Arg. as disclosed herein for use as a medicament for the treatment of a bacterial colonization or primary or secondary bacterial infection of an underlying skin disorder. In some embodiments latex of *Croton lechleri*, preferably filtered latex of *Croton lechleri*, preferably filtered latex of *Croton lechleri* Müll. Arg. has a PDI of embodiments disclosed herein.

Also provided is the use of latex of *Croton lechleri*, preferably filtered latex of *Croton lechleri*, preferably filtered latex of *Croton lechleri* Müll. Arg. as disclosed herein as a medicament for the treatment of a bacterial colonization or primary or secondary bacterial infection of an underlying skin disorder. In some embodiments latex of *Croton lechleri*, preferably filtered latex of *Croton lechleri*, preferably filtered latex of *Croton lechleri* Müll. Arg. has a PDI of embodiments disclosed herein.

Also provided is latex of *Croton lechleri*, preferably filtered latex of *Croton lechleri*, preferably filtered latex of *Croton lechleri* Müll. Arg., wherein the concentration of components of latex of *Croton lechleri*, preferably the concentration of components of filtered latex of *Croton lechleri*, preferably the concentration of components of filtered latex of *Croton lechleri* Müll. Arg of the reference standard, as disclosed herein for use in the manufacture of a medicament for the treatment of a bacterial colonization or primary or secondary bacterial infection of an underlying skin disorder. In some embodiments latex of *Croton lechleri*, preferably filtered latex of *Croton lechleri*, preferably filtered latex of *Croton lechleri* Müll. Arg. has a PDI of embodiments disclosed herein.

Also provided is the use of latex of *Croton lechleri*, preferably filtered latex of *Croton lechleri*, preferably filtered latex of *Croton lechleri* Müll. Arg., wherein the concentration of components of latex of *Croton lechleri*, preferably the concentration of components of filtered latex of *Croton lechleri*, preferably the concentration of components of filtered latex of *Croton lechleri* Müll. Arg of the reference standard, as disclosed herein for the treatment of a bacterial colonization or primary or secondary bacterial infection of an underlying skin disorder. In some embodiments latex of *Croton lechleri*, preferably filtered latex of *Croton lechleri*, preferably filtered latex of *Croton lechleri* Müll. Arg. has a PDI of embodiments disclosed herein.

Also provided herein is a method of treating a bacterial colonization or primary or secondary bacterial infection of an underlying skin disorder comprising contacting a bacterial colonization or primary or secondary bacterial infection of an underlying skin disorder with latex of *Croton lechleri*, preferably filtered latex of *Croton lechleri*, preferably filtered latex of *Croton lechleri* Müll. Arg., wherein the concentration of components of latex of *Croton lechleri*, preferably the concentration of components of filtered latex of *Croton lechleri*, preferably the concentration of components of filtered latex of *Croton lechleri* Müll. Arg of the reference standard, as disclosed herein. In some embodiments latex of *Croton lechleri*, preferably filtered latex of

*Croton lechleri*, preferably filtered latex of *Croton lechleri* Müll. Arg. has a PDI of embodiments disclosed herein.

Also provided herein is a method of treating a bacterial colonization or primary or secondary bacterial infection of the nasal mucosa comprising contacting a bacterial colonization or primary or secondary bacterial infection of the nasal mucosa with latex of *Croton lechleri*, preferably filtered latex of *Croton lechleri*, preferably filtered latex of *Croton lechleri* Müll. Arg., wherein the concentration of components of latex of *Croton lechleri*, preferably the concentration of components of filtered latex of *Croton lechleri*, preferably the concentration of components of filtered latex of *Croton lechleri* Müll. Arg of the reference standard, as disclosed herein. In some embodiments latex of *Croton lechleri*, preferably filtered latex of *Croton lechleri*, preferably filtered latex of *Croton lechleri* Müll. Arg. has a PDI of embodiments disclosed herein.

Also provided herein is a method for achieving a therapeutic effect in a patient comprising the administration of a therapeutically effective amount of latex of *Croton lechleri*, preferably filtered latex of *Croton lechleri*, preferably filtered latex of *Croton lechleri* Müll. Arg., wherein the concentration of components of latex of *Croton lechleri*, preferably the concentration of components of filtered latex of *Croton lechleri*, preferably the concentration of components of filtered latex of *Croton lechleri* Müll. Arg of the reference standard, as disclosed herein. In some embodiments latex of *Croton lechleri*, preferably filtered latex of *Croton lechleri*, preferably filtered latex of *Croton lechleri* Müll. Arg. has a PDI of embodiments disclosed herein.

In some embodiments, the bacterial colonization or primary or secondary bacterial infection of an underlying skin disorder is selected from the group consisting of *Streptococcus* pyogenes infection, Multi-drug resistant (MDR) *Streptococcus pyogenes* infection, *Staphylococcus aureus* infection, methicillin-resistant *Staphylococcus aureus* (MRSA) infection, Mupirocin-resistant MRSA infection, *Enterococcus faecalis* infection, Gram-positive bacteria infection, Gram-negative bacteria infection, cellulitis/erysipelas, wound infection, burn infection, major cutaneous abscesses, impetigo, Mupirocin-resistant impetigo, Vancomycin resistant bacteria infection, Erythronycin resistant bacteria infection, Tetracycline resistant bacteria infection, Mupirocin resistant bacteria infection, *Clostridium difficile* infection, drug-resistant *Neisseria gonorrhoeae* infection, *Streptococcus pneumoniae* infection, drug-resistant *Streptococcus pneumoniae* infection, drug-resistant *Klebsiella pneumoniae* infection, drug-resistant Malaria infection, Multi-drug resistant (MDR) infection, Extensively drug-resistant (XDR) Tuberculosis infection, *Escherichia coli* (*E. coli*) infection, Shiga toxin-producing *Escherichia coli* (*E. coli*) infection, infections caused by bacteria possessing Enzyme NDM-1 (New Delhi Metallo-beta-lactamase-1), *Clostridium difficile* infection, *Enterococcus* infection, *Mycobacterium tuberculosis* infection, *Mycoplasma genitalium* infection, *Streptococcus* infection, *Campylobacter* infection, *Neisseria gonorrhoeae* infection, Gamma proteobacteria infection, Enterobacteriaceae infection, Carbapenem-Resistant Enterobacteriaceae, infection, *Klebsiella pneumoniae* infection, *Salmonella* infection, *E. coli* infection, Pseudomonadales infection, *Acinetobacter* infection, *Pseudomonas aeruginosa* infection, MDR *Pseudomonas aeruginosa* infection, Coagulase-negative *Staphylococcus* infection, and combinations thereof.

In some embodiments, the bacterial colonization or primary or secondary bacterial infection of an underlying skin disorder is selected from the group consisting of *Streptococcus pyogenes* infection, MDR *Streptococcus pyogenes* infection, *Staphylococcus aureus* infection, methicillin-resistant *Staphylococcus aureus* (MRSA) infection, Mupirocin-resistant MRSA infection, *Enterococcus faecalis* infection, *Streptococcus pneumoniae* infection, *Escherichia coli* (*E. coli*) infection, *Pseudomonas aeruginosa* infection, MDR *Pseudomonas aeruginosa* infection, Coagulase-negative *Staphylococcus* infection, and combinations thereof.

In some embodiments, the bacterial colonization or primary or secondary bacterial infection of an underlying skin disorder is *Streptococcus pyogene* infection.

In some embodiments, the bacterial colonization or primary or secondary bacterial infection of an underlying skin disorder is MDR *Streptococcus pyogene* infection.

In some embodiments, the bacterial colonization or primary or secondary bacterial infection of an underlying skin disorder is *Staphylococcus aureus* infection.

In some embodiments, the bacterial colonization or primary or secondary bacterial infection of an underlying skin disorder is methicillin-resistant *Staphylococcus aureus* infection.

In some embodiments, the bacterial colonization or primary or secondary bacterial infection of an underlying skin disorder is Mupirocin-resistant MRSA infection.

In some embodiments, the bacterial colonization or primary or secondary bacterial infection of an underlying skin disorder is *Pseudomonas aeruginosa* infection.

In some embodiments, the bacterial colonization or primary or secondary bacterial infection of an underlying skin disorder is not methicillin-resistant *Staphylococcus aureus* (MRSA) infection.

In some embodiments, the bacterial colonization or primary or secondary bacterial infection of an underlying skin disorder is selected from the group consisting of *Streptococcus pyogenes* colonization, Multi-drug resistant (MDR) *Streptococcus pyogenes* colonization, *Staphylococcus aureus* colonization, methicillin-resistant *Staphylococcus aureus* (MRSA) colonization, Mupirocin-resistant MRSA colonization, *Enterococcus faecalis* colonization, Gram-positive bacteria colonization, Gram-negative bacteria colonization, cellulitis/erysipelas, wound colonization, burn colonization, major cutaneous abscesses, impetigo, Mupirocin-resistant impetigo, Vancomycin resistant bacteria colonization, Erythronycin resistant bacteria colonization, Tetracycline resistant bacteria colonization, Mupirocin resistant bacteria colonization, *Clostridium difficile* colonization, drug-resistant *Neisseria gonorrhoeae* colonization, *Streptococcus pneumoniae* colonization, drug-resistant *Streptococcus pneumoniae* colonization, drug-resistant *Klebsiella pneumoniae* colonization, drug-resistant Malaria colonization, MDR colonization, Extensively drug-resistant (XDR) Tuberculosis colonization, *Escherichia coli* (*E. coli*) colonization, Shiga toxin-producing *Escherichia coli* (*E. coli*) colonization, colonizations caused by bacteria possessing Enzyme NDM-1 (New Delhi Metallo-beta-lactamase-1), *Clostridium difficile* colonization, *Enterococcus* colonization, *Mycobacterium tuberculosis* colonization, *Mycoplasma genitalium* colonization, *Streptococcus* colonization, *Campylobacter* colonization, *Neisseria gonorrhoeae* colonization, Gamma proteobacteria colonization, Enterobacteriaceae colonization, Carbapenem-Resistant Enterobacteriaceae, colonization, *Klebsiella pneumoniae* colonization, *Salmonella* colonization, *E. coli* colonization, Pseudomonadales colonization, *Acinetobacter* colonization, *Pseudomonas aeruginosa* colonization, MDR *Pseudomonas aeruginosa* colonization, Coagulase-negative *Staphylococcus* colonization, and combinations thereof.

In some embodiments, the bacterial colonization or primary or secondary bacterial infection of an underlying skin disorder is selected from the group consisting of *Streptococcus pyogenes* colonization, MDR *Streptococcus pyogenes* colonization, *Staphylococcus aureus* colonization, methicillin-resistant *Staphylococcus aureus* (MRSA) colonization, Mupirocin-resistant MRSA colonization, *Enterococcus faecalis* colonization, *Streptococcus pneumoniae* colonization, *Escherichia coli* (*E. coli*) colonization, *Pseudomonas aeruginosa* colonization, MDR *Pseudomonas aeruginosa* colonization, Coagulase-negative *Staphylococcus* colonization, and combinations thereof.

In some embodiments, the bacterial colonization or primary or secondary bacterial infection of an underlying skin disorder is *Streptococcus pyogene* colonization.

In some embodiments, the bacterial colonization or primary or secondary bacterial infection of an underlying skin disorder is MDR *Streptococcus pyogene* colonization.

In some embodiments, the bacterial colonization or primary or secondary bacterial infection of an underlying skin disorder is *Staphylococcus aureus* colonization.

In some embodiments, the bacterial colonization or primary or secondary bacterial infection of an underlying skin disorder is methicillin-resistant *Staphylococcus aureus* colonization.

In some embodiments, the bacterial colonization or primary or secondary bacterial infection of an underlying skin disorder is Mupirocin-resistant MRSA colonization.

In some embodiments, the bacterial colonization or primary or secondary bacterial infection of an underlying skin disorder is *Pseudomonas aeruginosa* colonization.

In some embodiments, the bacterial colonization or primary or secondary bacterial infection of an underlying skin disorder is not methicillin-resistant *Staphylococcus aureus* (MRSA) colonization.

In some embodiment, the bacterial colonization or primary or secondary bacterial infection of an underlying skin disorder is a bacterial colonization or primary or secondary bacterial infection of the nasal mucosa.

In some embodiments, the bacterial colonization or primary or secondary bacterial infection of the nasal mucosa is selected from the group consisting of *Streptococcus pyogenes* infection, Multi-drug resistant (MDR) *Streptococcus pyogenes* infection, *Staphylococcus aureus* infection, methicillin-resistant *Staphylococcus aureus* (MRSA) infection, Mupirocin-resistant MRSA infection, *Enterococcus faecalis* infection, Gram-positive bacteria infection, Gram-negative bacteria infection, cellulitis/erysipelas, wound infection, burn infection, major cutaneous abscesses, impetigo, Mupirocin-resistant impetigo, Vancomycin resistant bacteria infection, Erythronycin resistant bacteria infection, Tetracycline resistant bacteria infection, Mupirocin resistant bacteria infection, *Clostridium difficile* infection, drug-resistant *Neisseria gonorrhoeae* infection, *Streptococcus pneumoniae* infection, drug-resistant *Streptococcus pneumoniae* infection, drug-resistant *Klebsiella pneumoniae* infection, drug-resistant Malaria infection, Multi-drug resistant (MDR) infection, Extensively drug-resistant (XDR) Tuberculosis infection, *Escherichia coli* (*E. coli*) infection, Shiga toxin-producing *Escherichia coli* (*E. coli*) infection, infections caused by bacteria possessing Enzyme NDM-1 (New Delhi Metallo-beta-lactamase-1), *Clostridium difficile* infection, *Enterococcus* infection, *Mycobacterium tuberculosis* infection, *Mycoplasma genitalium* infection, *Streptococcus* infection, *Campylobacter* infection, *Neisseria gonorrhoeae* infection, Gamma proteobacteria infection, Enterobacteriaceae infection, Carbapenem-Resistant Enterobacteriaceae, infection, *Klebsiella pneumoniae* infection, *Salmonella* infection, *E. coli* infection, Pseudomonadales infection, *Acinetobacter* infection, *Pseudomonas aeruginosa* infection, MDR *Pseudomonas aeruginosa* infection, Coagulase-negative *Staphylococcus* infection, and combinations thereof.

In some embodiments, the bacterial colonization or primary or secondary bacterial infection of the nasal mucosa is selected from the group consisting of *Streptococcus pyogenes* infection, MDR *Streptococcus pyogenes* infection, *Staphylococcus aureus* infection, methicillin-resistant *Staphylococcus aureus* (MRSA) infection, Mupirocin-resistant MRSA infection, *Enterococcus faecalis* infection, *Streptococcus pneumoniae* infection, *Escherichia coli* (*E. coli*) infection, *Pseudomonas aeruginosa* infection, MDR *Pseudomonas aeruginosa* infection, Coagulase-negative *Staphylococcus* infection, and combinations thereof.

In some embodiments, the bacterial colonization or primary or secondary bacterial infection of the nasal mucosa is *Streptococcus pyogene* infection.

In some embodiments, the bacterial colonization or primary or secondary bacterial infection of the nasal mucosa is MDR *Streptococcus pyogen infection.*

In some embodiments, the bacterial colonization or primary or secondary bacterial infection of the nasal mucosa is *Staphylococcus aureus* infection.

In some embodiments, the bacterial colonization or primary or secondary bacterial infection of the nasal mucosa is methicillin-resistant *Staphylococcus aureus* infection.

In some embodiments, the bacterial colonization or primary or secondary bacterial infection of the nasal mucosa is Mupirocin-resistant MRSA infection.

In some embodiments, the bacterial colonization or primary or secondary bacterial infection of the nasal mucosa is *Pseudomonas aeruginosa* infection.

In some embodiments, the bacterial colonization or primary or secondary bacterial infection of the nasal mucosa is not methicillin-resistant *Staphylococcus aureus* (MRSA) infection.

In some embodiments, the bacterial colonization or primary or secondary bacterial infection of the nasal mucosa is selected from the group consisting of *Streptococcus pyogenes* colonization, Multi-drug resistant (MDR) *Streptococcus pyogenes* colonization, *Staphylococcus aureus* colonization, methicillin-resistant *Staphylococcus aureus* (MRSA) colonization, Mupirocin-resistant MRSA colonization, *Enterococcus faecalis* colonization, Gram-positive bacteria colonization, Gram-negative bacteria colonization, cellulitis/erysipelas, wound colonization, burn colonization, major cutaneous abscesses, impetigo, Mupirocin-resistant impetigo, Vancomycin resistant bacteria colonization, Erythronycin resistant bacteria colonization, Tetracycline resistant bacteria colonization, Mupirocin resistant bacteria colonization, *Clostridium difficile* colonization, drug-resistant *Neisseria gonorrhoeae* colonization, *Streptococcus pneumoniae* colonization, drug-resistant *Streptococcus pneumoniae* colonization, drug-resistant *Klebsiella pneumoniae* colonization, drug-resistant Malaria colonization, MDR colonization, Extensively drug-resistant (XDR) Tuberculosis colonization, *Escherichia coli* (*E. coli*) colonization, Shiga toxin-producing *Escherichia coli* (*E. coli*) colonization, colonizations caused by bacteria possessing Enzyme NDM-1 (New Delhi Metallo-beta-lactamase-1), *Clostridium difficile* colonization, *Enterococcus* colonization, *Mycobacterium tuberculosis* colonization, *Mycoplasma genitalium* colonization, *Streptococcus* colonization, *Campylobacter* colonization, *Neisseria gonorrhoeae* colonization, Gamma proteobacteria colonization, Enterobacteriaceae colonization, Carbapenem-Resistant Enterobacteriaceae, colonization, *Klebsiella pneumoniae* colonization, *Salmonella* colonization, *E. coli* colonization, Pseudomonadales colonization, *Acinetobacter* colonization, *Pseudomonas aeruginosa* colonization, MDR *Pseudomonas aeruginosa* colonization, Coagulase-negative *Staphylococcus* colonization, and combinations thereof.

In some embodiments, the bacterial colonization or primary or secondary bacterial infection of the nasal mucosa is selected from the group consisting of *Streptococcus pyogenes* colonization, MDR *Streptococcus pyogenes* colonization, *Staphylococcus aureus* colonization, methicillin-resistant *Staphylococcus aureus* (MRSA) colonization, Mupirocin-resistant MRSA colonization, *Enterococcus faecalis* colonization, *Streptococcus pneumoniae* colonization, *Escherichia coli* (*E. coli*) colonization, *Pseudomonas aeruginosa* colonization, MDR *Pseudomonas aeruginosa* colonization, Coagulase-negative *Staphylococcus* colonization, and combinations thereof.

In some embodiments, the bacterial colonization or primary or secondary bacterial infection of the nasal mucosa is *Streptococcus pyogene* colonization.

In some embodiments, the bacterial colonization or primary or secondary bacterial infection of the nasal mucosa is MDR *Streptococcus pyogene* colonization.

In some embodiments, the bacterial colonization or primary or secondary bacterial infection of the nasal mucosa is *Staphylococcus aureus* colonization.

In some embodiments, the bacterial colonization or primary or secondary bacterial infection of the nasal mucosa is methicillin-resistant *Staphylococcus aureus* colonization.

In some embodiments, the bacterial colonization or primary or secondary bacterial infection of the nasal mucosa is Mupirocin-resistant MRSA colonization.

In some embodiments, the bacterial colonization or primary or secondary bacterial infection of the nasal mucosa is *Pseudomonas aeruginosa* colonization.

In some embodiments, the bacterial colonization or primary or secondary bacterial infection of the nasal mucosa is not methicillin-resistant *Staphylococcus aureus* (MRSA) colonization.

In some embodiments, the underlying skin disorder of the bacterial colonization or primary or secondary bacterial infection of an underlying skin disorder is selected from the group consisting of impetigo, atopic dermatitis, eczema, epidermolysis bullosa, psoriasis, wounds, and combinations thereof.

In some embodiments, the wound is selected from the group consisting of chronic wounds, superficial wounds, abrasions, and combinations thereof.

In some embodiments, the underlying skin disorder of the bacterial colonization or primary or secondary bacterial infection of an underlying skin disorder is selected from the group consisting of impetigo, atopic dermatitis, eczema, epidermolysis bullosa, psoriasis, chronic wounds, superficial wounds, abrasions, and combinations thereof.

In some embodiments, the underlying skin disorder of the bacterial colonization or primary or secondary bacterial infection of an underlying skin disorder is atopic dermatitis (also referred to as infected atopic dermatitis).

In some embodiments, the atopic dermatitis exhibits one or more symptoms selected from the group consisting of itchy skin, red/discolored skin, bleeding, weeping or oozing skin, cracked skin, scaly skin, flaky skin, dry or rough skin, painful skin, burning skin, disturbed sleep, and combinations thereof.

In some embodiments, one or more symptoms of the atopic dermatitis is improved.

In some embodiments, the atopic dermatitis is mild to moderate.

In embodiments described herein, the one or more symptoms improved by about day 1, about day 2, about day 3, about day 4, about day 5, about day 6, about day 7, about day 8, about day 9, about day 10, about day 11, about day 12, about day 13, about day 14, about day 15, about day 16, about day 17, about day 18, about day 19, about day 20, about day 21, about day 22, about day 23, about day 24, about day 25, about day 26, about day 27, about day 28, about day 29, about day 30, about day 31, about day 32, about day 33, about day 34, about day 35, about day 36, about day 37, about day 38, about day 39, about day 40, about day 41, about day 42, about day 43, about day 44, about day 45, about day 46, about day 47, about day 48, about day 49, about day 50, about day 51, about day 52, about day 53, about day 54, about day 55, about day 56, about day 57, about day 58, about day 59, or about day 60 of treatment.

In embodiments described herein, the one or more symptoms improved by about 2 weeks, about 3 weeks, about 4 weeks, about 5 weeks, about 6 weeks, about 7 weeks, or about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment. In embodiments described herein, the one or more symptoms improved by about 2 weeks after treatment. In embodiments described herein, the one or more symptoms improved by about 4 after treatment. In embodiments described herein, the one or more symptoms improved by about 8 weeks after treatment. In embodiments described herein, the one or more symptoms improved by about 12 weeks after treatment.

In embodiments described herein, the one or more symptoms of atopic dermatitis is measured according to an assessment selected from Investigator Global Assessment (IGA) score, Eczema Area and Severity Index (EASI), Skin Infection Rating Scale (SIRS), percent body surface area (BSA) affected, Patient Oriented Eczema Measure (POEM), one or more patient reported outcomes, and bacteriology response.

In embodiments described herein, the one or more symptoms of atopic dermatitis is improved as measured according to an assessment selected from Investigator Global Assessment (IGA) score, Eczema Area and Severity Index (EASI), Skin Infection Rating Scale (SIRS), percent body surface area (BSA) affected, Patient Oriented Eczema Measure (POEM), one or more patient reported outcomes, and bacteriology response.

In embodiments described herein, the Investigator's Global Assessment (IGA) is used for assessing the current state/severity of a subject's AD, also referred to as vIGA-AD™ (Validated Investigator Global Assessment for Atopic Dermatitis), a scale developed by Eli Lilly and Company and atopic dermatitis experts, including International Eczema Council advisors and Industry experts, for use in clinical trials. It uses a static 5-point morphological assessment of overall disease severity, as determined by the investigator, using the clinical characteristics of erythema, infiltration, papulation, oozing, and crusting as guidelines. In certain embodiments, the IGA is made daily, weekly, or monthly and without reference to previous scores. The scoring system ranges from 0 (=Clear) to 4 (=Severe). A score of 0 (Clear) has the following morphological description: no inflammatory signs of atopic dermatitis (no erythema, no induration/papulation, no lichenification, no oozing/crusting), and post-inflammatory hyperpigmentation and/or hypopigmentation may be present. A score of 1 (Almost Clear) has the following morphological description: barely perceptible erythema, barely perceptible induration/papulation, and/or minimal lichenification, and no oozing or crusting. A score of 2 (Mild) has the following morphological description: slight but definite erythema (pink), slight but definite induration/papulation, and/or slight but definite lichenification, and no oozing or crusting. A score of 3 (Moderate) has the following morphological description: clearly perceptible erythema (dull red), clearly perceptible induration/papulation, and/or clearly perceptible lichenification, and oozing and crusting may be present. A score of 4 (Severe) has the following morphological description: marked erythema (deep or bright red), marked induration/papulation, and/or marked lichenification, disease is widespread in extent, and oozing or crusting may be present. In embodiments described herein, the subject's Investigator Global Assessment (IGA) score decreased by at least about 1 point, at least about 2 points, at least about 3 points, at least about 4 points, or at least about 5 points. In embodiments described herein, the subject's Investigator Global Assessment (IGA) score decreased by about 1 point. In embodiments described herein, the subject's Investigator Global Assessment (IGA) score improved to a score of about 0 or about 1. In embodiments described herein, the subject's Investigator Global Assessment (IGA) score improved to a score of about 1 or almost clear. In certain embodiments, the subject's score decreased by at least about 1 point by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In certain embodiments, the subject's score decreased by at least about 2 points by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In embodiments described herein, the subject has sustained improvement of IGA after treatment has ended. In embodiments described herein, the subject has sustained improvement of IGA about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of IGA about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, the Eczema Area and Severity Index (EASI) is measured using a scoring system for assessing the severity of AD that takes into account the overall severity of erythema, infiltration/papulation, excoriation, and lichenification, as well as the extent of BSA affected with AD. The 4 clinical signs are each graded on a 4-point scale (0 to 3) for each of the 4 specified body regions (head and neck, upper extremities, lower extremities, and trunk). The EASI is a static assessment made without reference to previous scores. In embodiments described herein, the subject's Eczema Area and Severity Index (EASI) is improved by about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In embodiments described herein, the subject's Eczema Area and Severity Index (EASI) is improved by greater than or equal to 25%, greater than or equal to 50%, or greater than or equal to 75%. In embodiments described herein, the subject's Eczema Area and Severity Index (EASI) is improved by greater than or equal to 50%. In embodiments described herein, the subject's Eczema Area and Severity Index (EASI) is improved by greater than or equal to 75%. In certain embodiments, the subject achieved a greater than 50% improvement in EASI by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In certain embodiments, the subject achieved a greater than 75% improvement in EASI by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In certain embodiments, the subject achieved a greater than 90% improvement in EASI by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In embodiments described herein, the subject has sustained improvement of EASI after treatment has ended. In embodiments described herein, the subject has sustained improvement of EASI about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of EASI about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, SIRS is used to assess the severity of atopic dermatitis at baseline and end of treatment. It uses a static 4-point (0 to 3) scale morphological assessment of overall disease severity, as determined by the investigator, using the clinical characteristics of exudate/pus, crusting, erythema/inflammation, tissue edema, tissue warmth, itching, and pain. The SIRS score is the sum of the individual scores of each of the 7 clinical characteristics In embodiments described herein, the subject's SIRS score decreased by at least about 1 point, at least about 2 points, at least about 3 points, at least about 4 points, at least about 5 points, at least about 6 points, at least about 7 points, at least about 8 points, at least about 9 points, at least about 10 points, at least about 11 points, at least about 12 points, at least about 13 points, at least about 14 points, at least about 15 points, at least about 16 points, at least about 17 points, at least about 18 points, at least about 19 points, at least about 20 points, or at least about 21 points. In embodiments described herein, the subject's SIRS score decreased by about 1 point. In embodiments described herein, the subject's SIRS score improved to a score of about 0 or about 1. In embodiments described herein, the subject's SIRS score improved to a score of about 1. In certain embodiments, the subject's score decreased by at least about 1 point by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In certain embodiments, the subject's score decreased by at least about 2 points by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In embodiments described herein, the subject has sustained improvement of SIRS after treatment has ended. In embodiments described herein, the subject has sustained improvement of SIRS about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of SIRS about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

The assessment of the percent BSA affected is an estimate of the percentage of total involved skin with atopic dermatitis. The extent of BSA affected by AD is a general indicator of disease severity. In embodiments described herein, one percent body surface area (1% BSA) is the equivalent of the total palmar surface of the palm plus 5 digits. The percent BSA affected is calculated using the following regional body areas: Head and neck; Trunk, includes internal axillae and groin; Upper extremities, includes arms, external axillae, and hands; and Lower extremities, includes legs, buttocks, and feet. In embodiments described herein, body surface area (BSA) excludes the scalp, palms of the hands and soles of the feet. The percent BSA assessment is utilized in the EASI. The percent BSA affected by atopic dermatitis is evaluated from 0 to 100%. In embodiments described herein, the subject's percent body surface area (BSA) affected is decreased. In certain embodiments, the subject achieved a decrease in the percent BSA affected by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In embodiments described herein, the subject has sustained improvement of percent BSA affected after treatment has ended. In embodiments described herein, the subject has sustained improvement of percent body surface area (BSA) affected about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of percent BSA affected about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In embodiments described herein, the one or more patient reported outcomes are measured using Dermatology Life Quality Index (DLQI), Children's Dermatology Life Quality Index (CDLQI), Infant's Dermatology Quality of Life (IDQOL), Expanded Patient-Oriented Eczema Measure (POEM), and/or Peak Pruritus NRS.

In embodiments described herein, the subject assessed disease severity using the self-administered Expanded Patient-Oriented Eczema Measure (POEM). In embodiments described herein, the Expanded POEM assessed seven symptoms: 1.) skin that is itchy, 2.) bleeding, 3.) weeping/oozing, 4.) cracked, 5.) flaking, 6.) dry/rough, and 7.) disturbed sleep; measured using a 5-point scale of frequency of occurrence during the previous week. The 3 questions to assess sleep quality were directed to the frequency of waking at night difficulty falling asleep due to the atopic dermatitis. Individual responses were scored from 0 to 4. Improvement in sleep and improvement in itch were also measured using a visual analogue scale (VAS). In embodiments described herein, the subject's assessment of itchy skin, bleeding, weeping/oozing, cracked skin, flaking skin, dry/rough skin, and disturbed sleep each improved by about 1 point, about 2 points, 3 points, or about 4 points. In embodiments described herein, the subject's assessment of sleep quality is improved. In embodiments described herein, the subject's assessment of disturbed sleep improved. In certain embodiments, the subject reported an improvement on one or more symptoms assessed by POEM by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In embodiments described herein, the subject has sustained improvement of one or more symptoms assessed by the POEM after treatment has ended. In embodiments described herein, the subject has sustained improvement of one or more symptoms assessed by the POEM about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of one or more symptoms assessed by the POEM about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

In some embodiments, different quality of life scales are utilized to assess patient improvement through Patient Reported Outcome (PRO) measures. Dermatology Life Quality Index (DLQI) inquires about skin symptoms, feelings of embarrassment, and how skin disease has affected day-to-day activities, working and social life. Children's Dermatology Life Quality Index (CDLQI) includes physical symptoms, such as itching and sleep loss, as well as psychosocial questions regarding friendships, bullying, school performance, sports participation, and enjoyment of vacation. Infant's Dermatology Quality of Life (IDQOL) includes questions regarding an infant or young child's difficulties with mood, sleep, bathing, dressing, play, mealtimes, other family activities, and treatment. Peak Pruritus NRS is a single self-reported item designed to measure peak pruritus, or 'worst' itch, over the previous 24 h based on the following question: 'On a scale of 0 to 10, with 0 being "no itch" and 10 being "worst itch imaginable", how would you rate your itch at the worst moment during the previous 24 hours?'. In embodiments described herein, the subject score in one or more PRO, such as DLQI, CDLQI, IDQOL, POEM, and/or Peak Pruritus NRS improves.

In some embodiments, bacteriology response is used to assess the presence or absence of a bacterial colonization or primary or secondary bacterial infection. The bacteriology response assessed by Test of Cure (TOC). The investigator will assign each bacterial colonization or primary or secondary bacterial infection isolated at study baseline to one one of the microbiologic response categories, based on the TOC culture results, according to the following criteria:

- Eradicated: Absence of the Baseline Infecting Pathogen(s) in all TOC cultures obtained in the absence of potentially effective antibiotics.
- Presumed Eradicated: Presumed absence of the Baseline Infecting Pathogen(s) due to substantial improvement of infection so that no material for culture is available and participant is not on potentially effective antibiotics.
- Persisted: Continued presence of the Baseline Infecting Pathogen(s) in the post-therapy cultures.
- Presumed Persisted: Presumed presence of the Baseline Infecting Pathogen(s) at post-therapy visits for participants with clinical failure for whom no TOC culture was taken or a negative TOC culture was obtained while on potentially effective antibiotics.
- Non-evaluable: These participants have, by definition, substantive factors (eg, non-study antibiotics for reasons other than lack of efficacy, missing TOC evaluation) that preclude an accurate and valid assessment of their pathogen-level microbiologic response.

Each participant's skin infection due to one or more pathogens will be assigned a microbiological response. The post-therapy microbiological response for infection will be based on the following criteria:

- Microbiologic Success: All Baseline Infecting pathogens were eradicated or presumed eradicated, and no Superinfecting pathogen(s) were isolated at TOC.
- Microbiologic Failure: Persistence or presumed persistence of one or more Baseline Infecting pathogens at TOC or a Superinfecting pathogen isolated at TOC.
- Microbiologic Non-evaluable: The participant had a Sponsor-defined clinical outcome of "non-evaluable". These participants have, by definition, substantive factors (e.g. non-study antibiotics, missing TOC evaluation) that preclude an accurate and valid assessment of their pathogen-level microbiologic response.

For each Baseline Infecting Pathogen(s) "eradicated" or "presumed eradicated" will be considered as a satisfactory microbiologic response. "Persisted", "presumed persisted", or a positive culture for a superinfecting pathogen at end of treatment through TOC will be considered as an unsatisfactory microbiologic response.

In embodiments described herein, the subject's bacteriology response is eradicated. In certain embodiments, the subject's bacteriology response is eradicated by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In certain embodiments, the subject's bacteriology response is presumed eradicated by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In certain embodiments, the subject's bacteriology response is a microbiological success by day 1, day 2, day 3, day 4, day 5, day 6, day 7, day 8, day 9, day 10, day 11, day 12, day 13, day 14, day 15, day 16, day 17, day 18, day 19, day 20, day 21, day 22, day 23, day 24, day 25, day 26, day 27, day 28, day 29, day 30, day 31, day 32, day 33, day 34, day 35, day 36, day 37, day 38, day 39, day 40, day 41, day 42, day 43, day 44, day 45, day 46, day 47, day 48, day 49, day 50, day 51, day 52, day 53, day 54, day 55, day 56, day 57, day 58, day 59, or day 60. In embodiments described herein, the subject's bacteriology response is eradicated after treatment has ended. In embodiments described herein, the subject's bacteriology response is presumed eradicated after treatment has ended. In embodiments described herein, the subject's bacteriology response is a microbiological success after treatment has ended. In embodiments described herein, the subject's bacteriology response is eradicated about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject's bacteriology response is presumed eradicated about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject's bacteriology response is a microbiological success about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended. In embodiments described herein, the subject does not experience worsening of bacteriology response about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, or up to 52 weeks after treatment has ended.

The pharmaceutical compositions may be administered in various modes, e.g. topical (including, for example, dermal, oral mucosa, buccal, sublingual and intraocular) or nasal (via, for example, inhalation and/or spray). Also, the route of administration may vary depending on the condition and its severity.

The pharmaceutical compositions may be administered in various modes, e.g. topical (including, for example, dermal, oral mucosa, buccal, sublingual, intraocular, and wound cavity) or nasal (via, for example, inhalation and/or spray). The specific dose level for any particular patient will depend upon a variety of factors including the activity of the specific compound employed, the age, body weight, general health, sex, diet, time of administration, route of administration, rate of excretion, drug combination, the precise disorder being treated, and the severity of the indication or condition being treated. Also, the route of administration may vary depending on the condition and its severity.

Pharmaceutical compositions of the present invention may be administered once per day, twice per day, thrice per day, 4 times per day, 5 times per day, 6 times per day, 7 times per day, 8 times per day, 9 times per day, 10 times per day, or a range between of these values. In some embodiments, the pharmaceutical composition is administered twice per day. In some embodiments, the pharmaceutical composition is administered thrice per day. In some embodiments, the pharmaceutical composition is administered until the bacterial colonization or primary or secondary bacterial infection of an underlying skin disorder is resolved, gone, or treated.

Pharmaceutical compositions of the present invention may be administered continuously, every 15 minutes 30 min., 1 hour(s) (hr.), 1½ hr., 2 hr., 2½ hr., 3 hr., 4 hr., 6 hr., 8 hr., 12 hr., 24 hr., 36 hr., 48 hr., 3 days, 4 days, 5 days, 6, days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or a range between of these values. In some embodiments, the administration lasts 24 weeks. In particular embodiments, the administration lasts 2 weeks. In some embodiments, the administration lasts until the bacterial colonization or primary or secondary bacterial infection of an underlying skin disorder is resolved, gone, or treated.

Treatment of a bacterial colonization or primary or secondary bacterial infection of an underlying skin disorder may last 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or a range between of these values. In some embodiments, the treatment lasts 2 weeks. In some embodiments, the treatment lasts until the bacterial colonization or primary or secondary bacterial infection of an underlying skin disorder is resolved, gone, or treated.

Treatment of the bacterial colonization or primary or secondary bacterial infection of an underlying skin disorder may continue until complete resolution of the target lesion.

Treatment of the bacterial colonization or primary or secondary bacterial infection of an underlying skin disorder may continue at the discretion of the prescribing physician.

In certain embodiments, the pharmaceutical compositions of the present invention may be topically applied directly to the bacterial colonization or primary or secondary bacterial infection of an underlying skin disorder.

In certain embodiments, the pharmaceutical compositions of the present invention may be topically applied directly to the lesion that results from a bacterial colonization or primary or secondary bacterial infection of an underlying skin disorder.

In certain embodiments, the pharmaceutical compositions of the present invention may be nasally administered.

In certain embodiments, the pharmaceutical compositions of the present invention may be nasally administered via a nasal spray.

In certain embodiments, the pharmaceutical compositions of the present invention may be administered nasal inhalation.

In certain embodiments, dosage is 1-2 drops of a pharmaceutical compositions of the present invention per infection or colonization that is secondary to an underlying skin disorder, once, twice or more daily with the composition applied to each infection or colonization that is secondary to an underlying skin disorder. Multiple drops are applied to a crop of lesions. The drops are allowed to dry (several minutes) or they are gently rubbed (about 15 seconds) over the bacterial colonization or primary or secondary bacterial infection of an underlying skin disorder until the composition changes to a "creamier" state. It then dries very quickly (several seconds).

In certain embodiments, the pharmaceutical compositions of the present invention is first applied to a bandage (e.g., gauze), which is then applied to the bacterial colonization or primary or secondary bacterial infection of an underlying skin disorder. The treated bandage is applied to each lesion. If the bandage is separated from the lesion or if the dressing has been worn for 24 hours, a new, treated bandage may be applied. A new dressing is generally, but not always, applied every day and may be applied up to once per week or longer period of time. In one embodiment, the composition is administered until the symptoms (e.g., skin lesions) disappear, become less pronounced, or problematic side effects occur.

In some embodiments, the pharmaceutical composition has a minimum inhibitory concentration (MIC) of at least about 0.01%, at least about 0.05%, at least about 0.1%, at least about 0.25%, at least about 0.5%, at least about 0.75%, at least about 1%, at least about 3%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%.

Example 1—Evaluation of Ab-101 Antibacterial Activity

An Agar Well Diffusion Assay pilot evaluation of AB-101 BRM was conducted to seek an initial signal of the activity of AB-101 BRM against various bacteria. AB-101 BRM was tested against the following bacterial species:

| | |
|---|---|
| *Streptococcus pneumoniae* (ATCC 49619) (SPNEU) | Gram (+) |
| *Streptococcus pyogenes* (clinical isolate) (GABHS) | Gram (+) |
| *Enterococcus faecalis* (ATCC 29212) (EFAECL) | Gram (+) |
| *Coagulase-negative Staphylococcus* (clinical isolate) (CNS) | Gram (+) |
| *Escherichia coli* (ATCC 25922) (EC) | Gram (−) |
| *Pseudomonas aeruginosa* (ATCC 27853) (PAER) | Gram (−) |
| *Klebsiella pneumoniae* (ATCC 700603)(KPNEU) | Gram (−) |
| *Staphylococcus aureus* (ATCC 52923) (SAUR) | Gram (+) |
| *Methicillin-resistant Staphylococcus aureus* (ATCC 49476) (MRSA) | Gram (+) |

Isolates were subcultured the day before the Agar Well Diffusion Assay was performed. On the day of the assay, a bacterial suspension (0.08-0.12 MacFarland units) of each bacteria isolate was made in Trypticase Soy Broth (TSB), and these suspensions were used to plate a lawn of bacterial organisms on Mueller-Hinton agar or Mueller-Hinton sheep's blood agar. A control antibiotic Kirby-Bauer (K-B) disk plus K-B disks containing 25 uL of AB-101 dilutions were placed on the plates, and the plates were incubated overnight. The next day, the width of the zone of growth inhibition surrounding each K-B disk was recorded (in mm). The larger the number, the greater the zone of inhibition, and the greater the inhibition of growth of the target organisms.

AB-101 was used undiluted ($AB^0$) and in 10-fold dilutions ($AB^{-1}$, $AB^{-2}$, $AB^{-3}$, $AB^{-4}$) made in dimethylsulfoxide (DMSO). Control experiments showed that AB-101 BRM precipitated when mixed into either TSB or Hanks Balanced Salt Solution with $Ca^{++}$ and $Mg^{++}$, but was apparently soluble in DMSO, ethanol or methanol. However, when initially diluted into DMSO, EtOH or MeOH at 1:10 and subsequently diluted into TSB, AB-101 continued to precipitate. Therefore, all dilutions were made into DMSO and a K-B disk containing 25 uL DMSO was included in all experiments as a vehicle control. Table 3 provides a summary of the results. Table 4 (AMP=Ampicillin; GM=Gentamicin) provides the individual results of the Zone of Inhibition Assay for AB-101. As shown in Table 3 AB-101 is effective against both Gram (+) and Gram (−) bacteria.

TABLE 3

| Bacteria | Abbreviation | Bacteria Type | AB-101 Activity |
|---|---|---|---|
| *Streptococcus pneumoniae* | (SPNEU) | Gram (+) | Yes |
| *Streptococcus pyogenes* | (GABHS) | Gram (+) | Yes |
| *Enterococcus faecalis* | (EFAECL) | Gram (+) | Yes |
| *Coagulase-negative Staphylococcus* | (CNS) | Gram (+) | Yes |
| *Escherichia coli* | (EC) | Gram (−) | Yes |
| *Pseudomonas aeruginosa* | (PAER) | Gram (−) | Yes |
| *Klebsiella pneumoniae* | (KPNEU) | Gram (−) | Unknown |
| *Staphylococcus aureus* | (SAUR) | Gram (+) | Yes |
| *Methicillin-resistant Staphylococcus aureus* | (MRSA) | Gram (+) | Yes |

TABLE 4

| | Antibiotic | Zone of Inhibition (MM) | | | | | |
|---|---|---|---|---|---|---|---|
| | Controls | DMSO | $AB^0$ | $AB^{-1}$ | $AB^{-2}$ | $AB^{-3}$ | $AB^{-4}$ |
| SPNEU | Gram (+) | | | | | | |
| Jun. 3, 2005 | AMP 14 | 0 | 2 | 1 | <1 | <1 | <1 |
| Jun. 6, 2005 | AMP 13 | 0 | 4 | 1 | <1 | <1 | <1 |
| Jun. 7, 2005 | AMP no growth | | | | | | |
| GABHS | Gram (+) | | | | | | |
| Jun. 3, 2005 | AMP 13 | 0 | 2 | 1 | <1 | <1 | <1 |
| Jun. 6, 2005 | AMP 16 | <1 | 1 | <1 | Error | Error | Error |
| Jun. 7, 2005 | AMP 13 | <1 | 2 | 1 | 1 | <1 | <1 |
| EFAECL | Gram (+) | | | | | | |
| Jun. 3, 2005 | AMP 8 | 0 | 3 | 2 | 1 | <1 | <1 |
| Jun. 6, 2005 | GM 5 | <1 | 2 | 1 | <1 | <1 | <1 |
| Jun. 7, 2005 | AMP 8 | <1 | 3 | 1 | <1 | <1 | <1 |
| CNS | Gram (+) | | | | | | |
| Jun. 6, 2005 | GM 11 | <1 | 4 | 4 | 1 | <1 | <1 |
| Jun. 7, 2005 | GM 13 | <1 | 5 | 4 | 1 | <1 | <1 |
| EC | Gram (+) | | | | | | |
| Jun. 3, 2005 | GM 9 | 0 | <1 | 4 | 2 | <1 | <1 |
| Jun. 6, 2005 | GM 8 | <1 | ppt | 5 | 1 | <1 | <1 |
| Jun. 7, 2005 | GM 7 | <1 | <1 | 1 | <1 | <1 | <1 |
| PAER | Gram (−) | | | | | | |
| Jun. 3, 2005 | GM 7 | 0 | 4 | 1 | 1 | <1 | <1 |
| Jun. 6, 2005 | GM 10 | <1 | 1 | 1 | <1 | <1 | <1 |
| Jun. 7, 2005 | GM 8 | <1 | <1 | <1 | <1 | <1 | <1 |
| KPNEU | Gram (−) | | | | | | |
| Jun. 3, 2005 | GM 4 | 0 | <1 | <1 | <1 | <1 | <1 |
| Jun. 6, 2005 | GM 4 | <1 | <1 | <1 | <1 | <1 | <1 |
| Jun. 7, 2005 | GM 5 | <1 | <1 | <1 | <1 | <1 | <1 |
| SAUR | Gram (+) | | | | | | |
| Jun. 2, 2005 | GM 6 | 0 | 3 | 2 | <1 | <1 | <1 |
| Jun. 3, 2005 | GM 7 | 0 | 3 | 2 | <1 | <1 | <1 |
| Jun. 6, 2005 | GM 8 | <1 | 3 | 3 | 1 | <1 | <1 |
| Jun. 7, 2005 | GM 8 | 0 | 4 | 4 | <1 | <1 | <1 |
| MRSA | Gram (+) | | | | | | |
| Jun. 3, 2005 | GM 1 | 0 | 5 | 3 | <1 | <1 | <1 |
| Jun. 6, 2005 | GM <1 | <1 | 4 | 4 | <1 | <1 | <1 |
| Jun. 7, 2005 | GM 1 | 0 | 5 | 4 | <1 | <1 | <1 |

When evaluating the preliminary K-B data, there was a dilution effect on inhibition which validated this testing. The zones of inhibition are 4-5 mm at the highest concentration, which is indicative of antibacterial activity especially since no standard for what constitutes activity exists for the compounds in AB-101. When assessing antibiotic effects in a K-B type test, the minimum zone of inhibition for considering a positive test varies depending on the antibiotic tested with anything more than 0 mm considered positive in some cases or as much as 10 mm or more needed for others. The laboratory concluded that with AB-101, any inhibition should be considered a preliminary positive test and confirmed with more rigorous testing, and that AB-101's actual antibacterial activity may be greater than what was seen in these experiments. AB-101 was insoluble in aqueous buffer which likely limited its diffusion into agar further indicating anything more than 0 mm for AB-101 should be considered positive.

As shown in Table 4, AB-101 had the greatest activity against the following Gram-positive organisms: Staphylococci>Streptococci & *Enterococcus faecalis*. Data for AB-101 activity against Gram-negative rods suggests activity against *Pseudomonas aeruginosa* and *E. coli*, but minimal activity against *Klebsiella*.

Example 2—Antibacterial Testing of AB-101 Against *Staphylococcus aureus*

AB-101 was tested against an extensive variety of bacterial strains, including Mupirocin-resistant MRSA, Mupirocin-resistant MSSA, Mupirocin-susceptible MSSA, Mupirocin-susceptible MRSA, and other skin-related pathogens.

The initial antimicrobial testing of AB-101 is described below. The efficacy of AB-101 was assessed against ATCC 29213, an MSSA strain and ATCC 33591, an MRSA strain, using a variety of different microbiological assays in an attempt to identify the best approach at determining AB-101 sensitivity.

The first assay performed was the agar diffusion assay. A lawn of bacteria was painted on an agar plate, and the surface was then gently incised with a 6 mm biopsy punch. A 10 μL droplet of sample was then applied inside the ring incised by the biopsy punch. Three lots of AB-101 were assessed and test conditions were conducted in duplicates. After the agar plates were incubated, the diameter of the Zone of Inhibition (ZOI) was measured with a ruler and the average diameter was calculated; for samples where the ZOI was not circular, the diameter of the narrowest portion of the ZOI was measured. Table 5 provides the average zone of inhibition of AB-101 resin in the agar diffusion assay.

TABLE 5

| | Average zone of inhibition (mm) of AB-101 resin | | |
|---|---|---|---|
| Strain | AB-101 Lot 00 | AB-101 Lot 01 | AB-101 Lot 02 |
| ATCC 29213 (MSSA) | 8.0 | 8.5 | 7.5 |
| ATCC 33591 (MRSA) | 8.5 | 9.0 | 9.0 |

The ZOI for AB-101 was around 7.5 to 9.0 mm and were similar between MRSA and MSSA. The surface of AB-101 droplets tend to form a film after exposure to air, resulting in higher surface tension and limiting its ability to flow and spread across the surface of the agar. Extractions of raw, botanical material are often performed prior to antimicrobial testing. A methanol extraction of AB-101 by lyophilizing the resin to remove its water content, then resuspending the dried powder to 250 mg/mL with pure methanol. Each lot of methanol extracted AB-101 was then tested in an agar diffusion assay in triplicates, and methanol-only controls were included for each strain to assess the antimicrobial contribution of the solvent. The average ZOI of the methanol extracted AB-101 is summarized in Table 6. A representative image of the ZOI of methanol extracted AB-101 against MSSA (on the left) and MRSA (on the right) is shown in FIG. 6, with the methanol extract on the top of the plates and the methanol controls on the bottom of the plates.

TABLE 6

| | Average zone of inhibition (mm) of methanol extracted AB-101 | | | |
|---|---|---|---|---|
| Strain | AB-101 Lot 00 | AB-101 Lot 01 | AB-101 Lot 02 | Methanol control |
| ATCC 29213 (MSSA) | 17.3 | 18.3 | 16.7 | 9.1 |
| ATCC 33591 (MRSA) | 20.0 | 23.7 | 20.7 | 8.8 |

The average ZOI of methanol extracted AB-101 were between 16.7 to 23.7 mm, roughly double that of the methanol-only control (Table 7). In addition, the ZOI of the methanol control as seen in Table 7 is hazy, indicating the methanol evaporated quickly after being dispensed on the agar and did not greatly inhibit bacterial growth. This contrasts with methanol extracted AB-101, which exhibit very clear ZOI, indicative of a strong antimicrobial effect from AB-101.

In addition to agar diffusion assay, the antimicrobial activity of AB-101 was assessed in broth microdilution assay. Both AB-101 and methanol extracted AB-101 were tested by 2-fold serial dilutions into the bacteriological media, Cation-Adjusted Mueller-Hinton Broth (CAMHB). An equal volume of bacteria inoculum was then added to the serially diluted samples in a 96 well plate to generate the final test concentrations in Table 7. A methanol-only control was also included to determine the contribution of the solvent for the methanol extracted AB-101. All conditions were tested in duplicates and the 96 well plates were incubated overnight for approximately 20 hours at 37° C.

TABLE 7

| Concentration of AB-101 and methanol extracted AB-101 tested in broth microdilution assay | | | | | | | | | | | | |
|---|---|---|---|---|---|---|---|---|---|---|---|---|
| Well # | 1 | 2 | 3 | 4 | 5 | 6 | 7 | 8 | 9 | 10 | 11 | 12 |
| AB-101 (%) | 50 | 25 | 12.5 | 6.25 | 3.125 | 1.563 | 0.781 | 0.391 | 0.195 | 0.098 | 0.049 | 0 |
| Methanol AB-101 (mg/mL) | 125 | 62.5 | 31.25 | 15.625 | 7.8125 | 3.906 | 1.953 | 0.977 | 0.488 | 0.244 | 0.122 | 0 |
| Methanol control (%) | 50 | 25 | 12.5 | 6.25 | 3.125 | 1.563 | 0.781 | 0.391 | 0.195 | 0.098 | 0.049 | 0 |

Both AB-101 and the methanol extracted AB-101 formed cloudy, brownish precipitates in the presence of the water-based CAMHB media. To assess the viability of bacteria in the cloudy suspension, 10 μL from each assay condition was drop-platted on agar and incubated to determine the Minimum Bactericidal Concentration (MBC), which is defined as the lowest concentration of a test solution from which no colonies are recovered after incubation. The MBC values were determined below in Table 8. The MBC value of the methanol extracted AB-101 is considerable lower than the methanol-only control, a result that is similar to the agar diffusion assay performed with this form of AB-101 (see Table 8), and reinforces the observation that methanol extracted AB-101 has potent antimicrobial efficacy against *Staphylococcus aureus*, which includes MRSA, Mupirocin-resistant MRSA and MSSA that is independent from the solvent.

TABLE 8

MBC values of AB-101 and methanol extracted AB-101 tested in broth microdilution assay

| Strain | AB-101 MBC (%) | | Methanol Extracted AB-101 MBC (mg/mL) | | Methanol control MBC (%) | |
|---|---|---|---|---|---|---|
| MSSA (ATCC 29213) | 50 | 50 | 0.977 | 0.977 | 50 | 50 |
| MRSA (ATCC 33591) | 50 | 50 | 0.977 | 0.977 | 50 | 50 |

Figure 7:
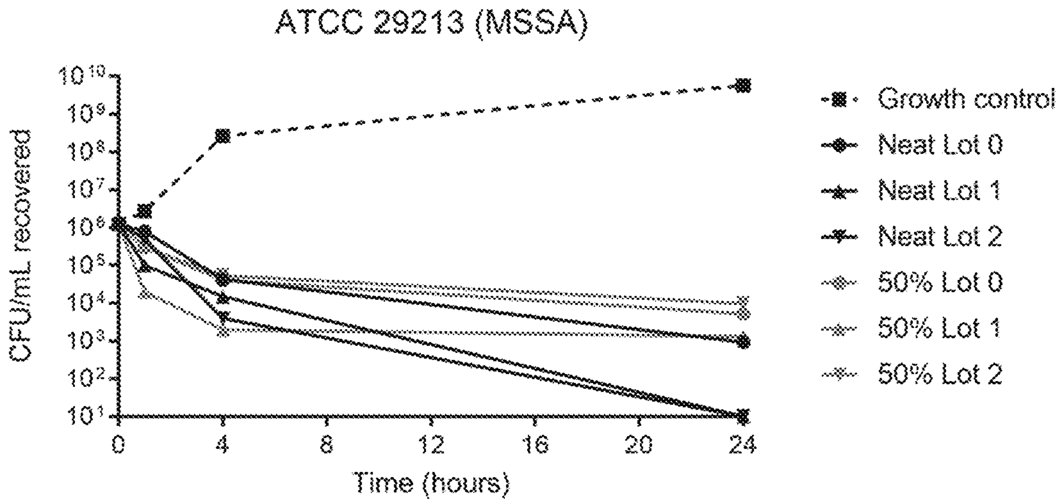
FIG. 7 depicts the MSSA recovered over time in time-kill kinetic assay.
Figure 8:
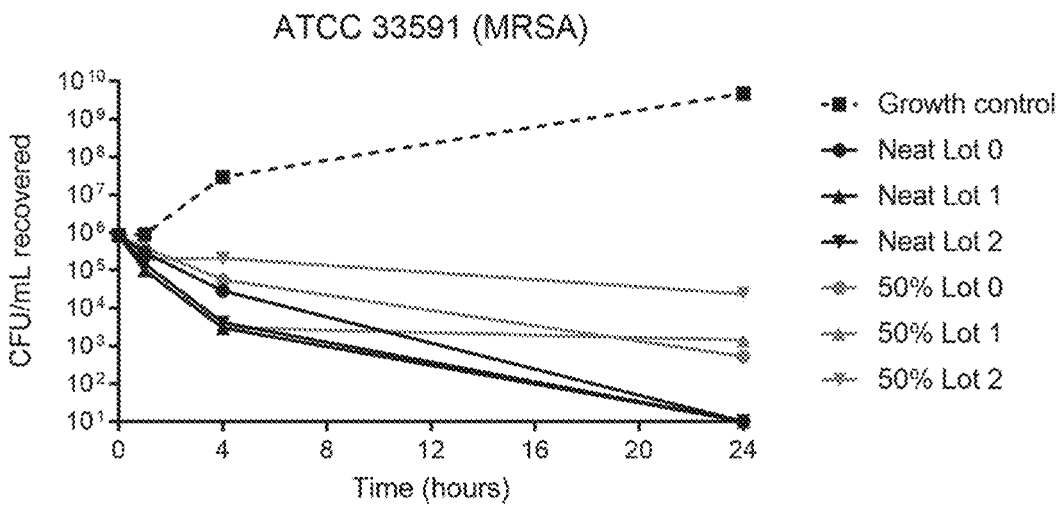
FIG. 8 depicts the MRSA recovered over time in time-kill kinetic assay.
Figure 9:
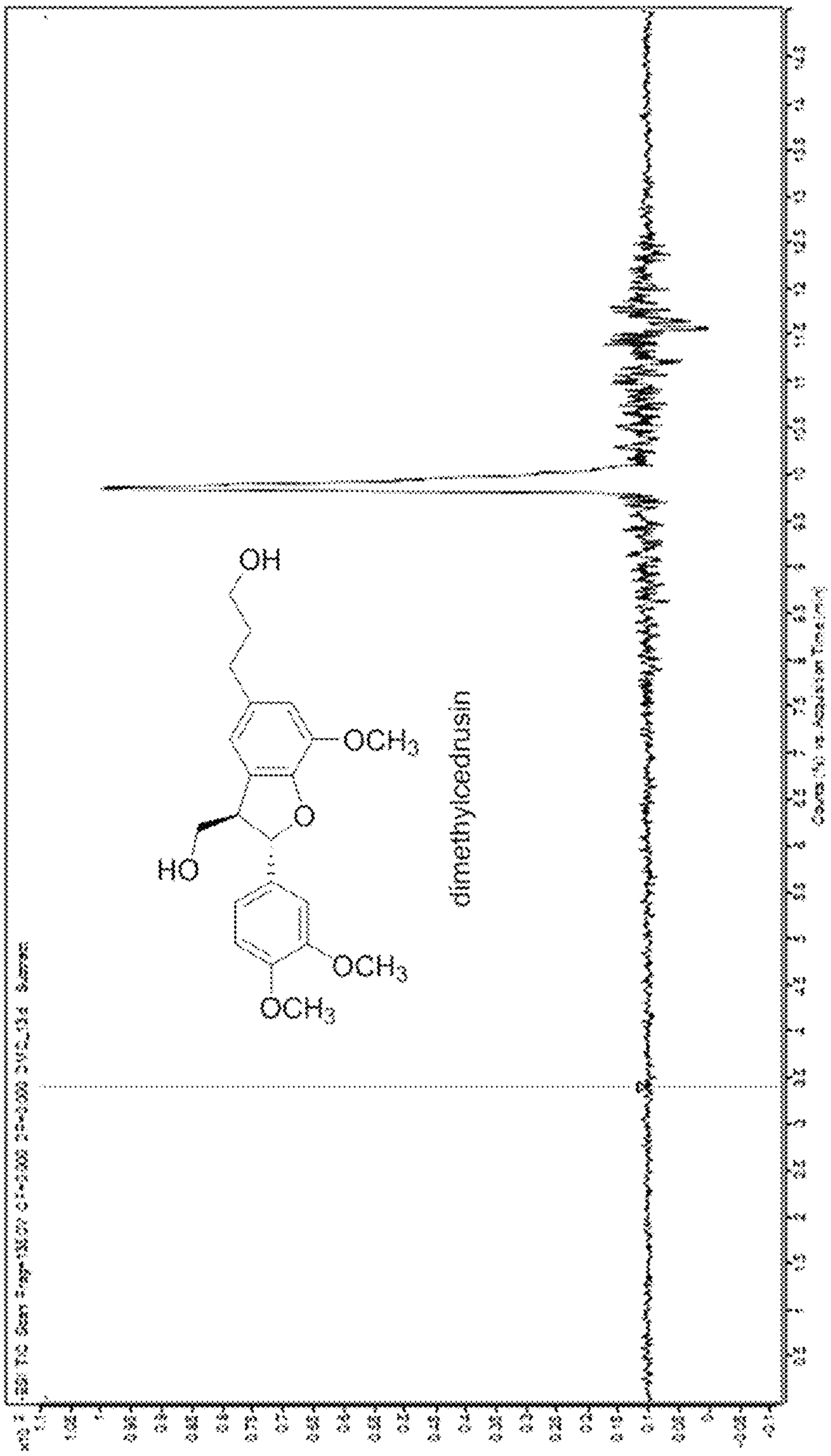
FIG. 9 depicts a representative Total Ion Chromatogram of dimethylcedrusin.

While the precipitation of AB-101, both in BRM and methanol extracted form, possesses a significant technical challenge for rapid antimicrobial screening, we noticed that the MBC value for AB-101 BRM is 50%. This indicates AB-101 is bactericidal in the range of 100% to 50% within 20 hours of contact with *S. aureus*. To determine how quickly and to what extent AB-101 exerts its bactericidal effect, a time-kill kinetics assay was performed against MRSA and MSSA. Undiluted AB-101 BRM or AB-101 diluted to 50% (v/v) with CAMHB were inoculated with MSSA or MRSA. Bacteria density was enumerated on agar plates at 1, 4, and 24 hours after inoculation and graphed relative to the time 0 inoculum density. The CFU/mL recovered and graphed data for MSSA (Table 9 and FIG. 7) and MRSA (Table 10 and FIG. 8) are shown below. In Table 9 CFU/mL values for Undiluted AB-101 BRM Lot 001 at T24 and Undiluted AB-101 BRM Lot 002 at T24 and in Table 10 CFU/mL values for Undiluted AB-101 BRM Lot 00 at T24, Undiluted AB-101 BRM Lot 001 at T24 and Undiluted AB-101 BRM Lot 002 at T24 indicate samples from which no colonies were recovered and represents the limit of detection of the assay (ie, 10 CFU/mL).

TABLE 9

MSSA CFU/mL recovered in time-kill assay

| ATCC 29213 (MSSA) | CFU/mL recovered T0 | T1 | T4 | T24 |
|---|---|---|---|---|
| Growth control | 1.2E+06 | 2.7E+06 | 2.7E+08 | 5.8E+09 |
| Undiluted AB-101 Lot 00 | | 8.0E+05 | 4.3E+04 | 9.3E+02 |
| Undiluted AB-101 Lot 01 | | 1.0E+05 | 1.5E+04 | 1.0E+01 |
| Undiluted AB-101 Lot 02 | | 5.0E+05 | 4.0E+03 | 1.0E+01 |
| Diluted AB-101 50% Lot 00 | | 3.0E+05 | 4.1E+04 | 5.2E+03 |

TABLE 9-continued

MSSA CFU/mL recovered in time-kill assay

| ATCC 29213 (MSSA) | CFU/mL recovered T0 | T1 | T4 | T24 |
|---|---|---|---|---|
| Diluted AB-101 50% Lot 01 | | 2.0E+04 | 2.0E+03 | 1.3E+03 |
| Diluted AB-101 50% Lot 02 | | 3.0E+05 | 5.4E+04 | 9.7E+03 |

TABLE 10

MRSA CFU/mL recovered in time-kill assay

| ATCC 33591 (MRSA) | CFU/mL recovered T0 | T1 | T4 | T24 |
|---|---|---|---|---|
| Growth control | 8.5E+05 | 9.0E+05 | 3.0E+07 | 4.8E+09 |
| Neat Lot 00 | | 3.0E+05 | 2.9E+04 | 1.0E+01 |
| Neat Lot 01 | | 1.0E+05 | 3.0E+03 | 1.0E+01 |
| Neat Lot 02 | | 1.5E+05 | 4.2E+03 | 1.0E+01 |
| 50% Lot 00 | | 4.0E+05 | 5.7E+04 | 5.3E+02 |
| 50% Lot 01 | | 1.0E+05 | 3.1E+03 | 1.4E+03 |
| 50% Lot 02 | | 2.0E+05 | 2.1E+05 | 2.4E+04 |

Compared to the growth control (which contained no AB-101), both the undiluted AB-101 BRM and the 50% diluted AB-101 BRM reduced the bacterial density by 2 to 3 Log 10 CPUs 4 hours post inoculation. By 24 hours, the MSSA and MRSA densities were reduced by ≥7 Log 10 CFUs compared to growth control, and nearly all undiluted AB-101 test samples reduced the bacterial density to a level that is below the limit of detection for this assay. The time-kill assay therefore further confirmed the bactericidal effect of AB-101 against *S. aureus.*

Example 3

To demonstrate the effectiveness of AB-101 and how changes within different type of latex extract can change performance and well as showing that not all extracts, even in the same plant species, yields the same pharmaceutical grade performance, invitro assay of MSSA and MRSA were conducted. Measures included the minimum inhibitory concentration (MIC) which is the lowest concentration of AB-101 that prevents visible growth of the bacterium or pathogen, and minimum bactericidal concentration (MBC) which is the lowest concentration of an antibacterial agent required to kill a bacterium.

The comparison of AB-101 Lot 01 and 2 for MIC demonstrates a high effectiveness against MSSA and MRSA with particular emphasis on the Mupirocin resistant strain of MRSA. Mupirocin is a leading topical treatment for MRSA. Shown for the first time is the effectiveness of AB-101 against these pathogens and importantly an improvement over the leading current pharmaceutical treatment. Results are shown in Table 11.

TABLE 11

| | | MIC (% vol./vol.) | | | | MIC (μg/mL) | |
|---|---|---|---|---|---|---|---|
| Strain ID | Characteristic | AB-101 Lot 01 | | AB-101 Lot 02 | | Methicillin | Mupirocin |
| CDC 218 | MupirocinR, MRSA | 12.5 | 12.5 | 12.5 | 12.5 | >64 | >256 |
| CDC 224 | MupirocinR, MRSA | 12.5 | 12.5 | 12.5 | 12.5 | >64 | >256 |
| CDC 228 | MupirocinR, MRSA | 3.13 | 3.13 | 3.13 | 3.13 | 64 | >256 |
| 1674606 | MupirocinR, MSSA | 50 | 50 | 50 | 50 | 2-8 | >256 |
| 1674607 | MupirocinR, MRSA | 12.5 | 12.5 | 12.5 | 12.5 | >64 | >256 |
| 1674608 | MupirocinR, MSSA | 12.5 | 12.5 | 25 | 50 | 2-4 | >256 |
| 1674611 | MupirocinR, MRSA | 6.25 | 6.25 | 12.5 | 12.5 | 64 | >256 |
| CDC 480 | MupirocinS, MRSA | 12.5 | 25 | 12.5 | 25 | 32-64 | ≤0.25 |
| CDC 481 | MupirocinS, MRSA | 12.5 | 12.5 | 12.5 | 12.5 | 16-32 | ≤0.25 |
| CDC 482 | MupirocinS, MRSA | 12.5 | 12.5 | 12.5 | 12.5 | 8-32 | ≤0.25 |
| CDC 483 | MupirocinS, MRSA | 12.5 | 12.5 | 12.5 | 12.5 | 64 | ≤0.25 |
| CDC 220 | MupirocinS, MRSA | 12.5 | 12.5 | 6.25 | 12.5 | 64->64 | ≤0.25 |
| CDC 227 | MupirocinS, MRSA | 6.25 | 6.25 | 12.5 | 12.5 | 64 | ≤0.25-0.5 |
| CDC 461 | MupirocinS, MSSA | 12.5 | 12.5 | 12.5 | 12.5 | 4-8 | ≤0.25-1 |
| CDC 462 | MupirocinS, MSSA | 6.25 | 12.5 | 6.25 | 12.5 | 8 | ≤0.25 |
| CDC 463 | MupirocinS, MSSA | 6.25 | 6.25 | 12.5 | 12.5 | 8-16 | ≤0.25-0.5 |
| CDC 464 | MupirocinS, MSSA | 12.5 | 12.5 | 12.5 | 12.5 | 2 | ≤0.25 |
| CDC 484 | MupirocinS, MSSA | 12.5 | 12.5 | 12.5 | 12.5 | 2 | ≤0.25 |
| CDC 485 | MupirocinS, MSSA | 50 | 50 | 50 | 50 | 2-4 | ≤0.25 |
| ATCC 29213 | QC control | 12.5 | 50-12.5 | 12.5 | 12.5 | 1-2 | ≤0.25-0.5 |

Table 12 shows the comparison of AB-101 Lots 01 and 02 for MBC demonstrates a high effectiveness against MSSA and MRSA with particular emphasis on the mupirocin resistant strain of MRSA. Once again Mupirocin is a leading topical treatment for MRSA. Shown for the first time is the effectiveness of AB-101 against these pathogens and importantly an improvement over the leading current pharmaceutical treatment.

TABLE 12

| | | MBC (% vol./vol.) | | | |
|---|---|---|---|---|---|
| Strain ID | Characteristic | AB-101 Lot 1 | | AB-101 Lot 2 | |
| CDC 218 | MupirocinR, MRSA | 50 | 50 | 50 | 50 |
| CDC 224 | MupirocinR, MRSA | 50 | 50 | 50 | 50 |
| CDC 228 | MupirocinR, MRSA | 6.25 | 6.25 | 6.25 | 6.25 |
| 1674606 | MupirocinR, MSSA | >50 | >50 | >50 | >50 |
| 1674607 | MupirocinR, MRSA | 12.5 | 12.5 | 25 | 25 |
| 1674608 | MupirocinR, MSSA | 50 | 50 | 50 | >50 |
| 1674611 | MupirocinR, MRSA | 12.5 | 12.5 | 50 | 50 |
| CDC 480 | MupirocinS, MRSA | 50 | 50 | 50 | 50 |
| CDC 481 | MupirocinS, MRSA | 50 | 50 | 50 | 50 |
| CDC 482 | MupirocinS, MRSA | 50 | 50 | 50 | 50 |
| CDC 483 | MupirocinS, MRSA | 50 | 50 | 50 | 50 |

TABLE 12-continued

| | | MBC (% vol./vol.) | | | |
|---|---|---|---|---|---|
| Strain ID | Characteristic | AB-101 Lot 1 | | AB-101 Lot 2 | |
| CDC 220 | MupirocinS, MRSA | 25 | 25 | 25 | 25 |
| CDC 227 | MupirocinS, MRSA | 12.5 | 12.5 | 25 | 25 |
| CDC 461 | MupirocinS, MSSA | 50 | 50 | 50 | 50 |
| CDC 462 | MupirocinS, MSSA | 12.5 | 50 | 50 | 50 |
| CDC 463 | MupirocinS, MSSA | 12.5 | 12.5 | 12.5 | 12.5 |
| CDC 464 | MupirocinS, MSSA | >50 | 50 | 50 | 50 |
| CDC 484 | MupirocinS, MSSA | 50 | 50 | 50 | 50 |
| CDC 485 | MupirocinS, MSSA | 50 | 50 | 50 | 50 |
| ATCC 29213 | QC control | 50-12.5 | 50-12.5 | 50 | 50 |

Table 13 compares AB-101 lot X and Lot 00 for MIC because these lots have been shown elsewhere to have different composition. Lot X and Lot 00 are latex extracts of *Croton lechleri* Müll. Arg., the same species, grown in similar locations. Lot X demonstrates a significantly higher effectiveness against MSSA and MRSA. This data shows for the first time that not all latex extracts of *Croton lechleri* Müll. Arg. provide the same performance, even when the extracts are from the same species grown in similar locations.

TABLE 13

| | | MIC (% vol./vol.) | | | | MIC (μg/mL) | |
|---|---|---|---|---|---|---|---|
| Strain ID | Characteristic | AB-101 Lot 00 | | AB-101 Lot X | | Methicillin | Mupirocin |
| CDC 218 | MupirocinR, MRSA | 12.5 | 12.5 | 0.78 | 0.78 | >64 | >256 |
| CDC 224 | MupirocinR, MRSA | 12.5 | 12.5 | 0.78 | 0.78 | >64 | >256 |
| CDC 228 | MupirocinR, MRSA | 3.13 | 3.13 | 0.39 | 0.39 | 64 | >256 |
| 1674606 | MupirocinR, MSSA | >50 | >50 | 1.56 | 1.56 | 2-8 | >256 |
| 1674607 | MupirocinR, MRSA | 12.5 | 12.5 | 0.78 | 0.78 | >64 | >256 |
| 1674608 | MupirocinR, MSSA | 25 | 25 | 1.56 | 1.56 | 2-4 | >256 |
| 1674611 | MupirocinR, MRSA | 25 | 25 | 0.78 | 0.78 | 64 | >256 |
| CDC 480 | MupirocinS, MRSA | 12.5 | 12.5 | 1.56 | 1.56 | 32-64 | ≤0.25 |
| CDC 481 | MupirocinS, MRSA | 12.5 | 12.5 | 1.56 | 1.56 | 16-32 | ≤0.25 |
| CDC 482 | MupirocinS, MRSA | 12.5 | 12.5 | 0.78 | 0.78 | 8-32 | ≤0.25 |
| CDC 483 | MupirocinS, MRSA | 12.5 | 12.5 | 0.78 | 0.78 | 64 | ≤0.25 |
| CDC 220 | MupirocinS, MRSA | 12.5 | 12.5 | 0.78 | 0.78 | 64->64 | ≤0.25 |
| CDC 227 | MupirocinS, MRSA | 12.5 | 12.5 | 0.78 | 0.78 | 64 | ≤0.25-0.5 |

TABLE 13-continued

| | | MIC (% vol./vol.) | | | | MIC (μg/mL) | |
|---|---|---|---|---|---|---|---|
| Strain ID | Characteristic | AB-101 Lot 00 | | AB-101 Lot X | | Methicillin | Mupirocin |
| CDC 461 | MupirocinS, MSSA | 50 | 50 | 0.78 | 0.78 | 4-8 | ≤0.25-1 |
| CDC 462 | MupirocinS, MSSA | 12.5 | 12.5 | 0.78 | 0.78 | 8 | ≤0.25 |
| CDC 463 | MupirocinS, MSSA | 12.5 | 12.5 | 1.56 | 0.78 | 8-16 | ≤0.25-0.5 |
| CDC 464 | MupirocinS, MSSA | >50 | >50 | 1.56 | 1.56 | 2 | ≤0.25 |
| CDC 484 | MupirocinS, MSSA | >50 | 25 | 0.78 | 1.56 | 2 | ≤0.25 |
| CDC 485 | MupirocinS, MSSA | >50 | >50 | 0.78 | 0.78 | 2-4 | ≤0.25 |
| ATCC 29213 | QC control | 12.5 | 12.5 | 1.56 | 1.56 | 1-2 | ≤0.25-0.5 |

Table 14 compares AB-101 lot X and Lot 00 for MBC because these lots have been shown elsewhere to have different composition. Lot X and Lot 00 are latex extracts of *Croton lechleri* Müll. Arg., the same species, grown in similar locations. Lot X demonstrates a significantly higher effectiveness against MSSA and MRSA. This data shows for the first time that not all latex extracts of *Croton lechleri* Müll. Arg. provide the same performance, even when the extracts are from the same species grown in similar locations.

TABLE 14

| | | MBC (% vol./vol.) | | | |
|---|---|---|---|---|---|
| Strain ID | Characteristic | AB-101 Lot 00 | | AB-101 Lot X | |
| CDC 218 | MupirocinR, MRSA | >50 | 50 | 0.78 | 0.78 |
| CDC 224 | MupirocinR, MRSA | >50 | >50 | 0.78 | 0.78 |
| CDC 228 | MupirocinR, MRSA | 12.5 | 12.5 | 0.39 | 0.78 |
| 1674606 | MupirocinR, MSSA | >50 | >50 | 1.56 | 1.56 |
| 1674607 | MupirocinR, MRSA | 25 | 25 | >50 | >50 |
| 1674608 | MupirocinR, MSSA | >50 | >50 | 1.56 | 1.56 |
| 1674611 | MupirocinR, MRSA | 50 | >50 | 0.78 | 0.78 |
| CDC 480 | MupirocinS, MRSA | >50 | >50 | 1.56 | 3.12 |
| CDC 481 | MupirocinS, MRSA | >50 | >50 | 1.56 | 1.56 |
| CDC 482 | MupirocinS, MRSA | >50 | >50 | 0.78 | 0.78 |
| CDC 483 | MupirocinS, MRSA | >50 | >50 | 0.78 | 0.78 |
| CDC 220 | MupirocinS, MRSA | 50 | 50 | 0.78 | 1.56 |
| CDC 227 | MupirocinS, MRSA | 25 | 25 | 1.56 | 0.78 |
| CDC 461 | MupirocinS, MSSA | >50 | >50 | 0.78 | 0.78 |
| CDC 462 | MupirocinS, MSSA | 50 | 50 | 0.78 | 0.78 |
| CDC 463 | MupirocinS, MSSA | 12.5 | 12.5 | 6.25 | 6.25 |
| CDC 464 | MupirocinS, MSSA | >50 | >50 | 1.56 | 1.56 |
| CDC 484 | MupirocinS, MSSA | >50 | >50 | 1.56 | 1.56 |

TABLE 14-continued

| | | MBC (% vol./vol.) | | | |
|---|---|---|---|---|---|
| Strain ID | Characteristic | AB-101 Lot 00 | | AB-101 Lot X | |
| CDC 485 | MupirocinS, MSSA | >50 | >50 | >50 | >50 |
| ATCC 29213 | QC control | 50 | 50 | 6.25 | 3.13 |

To demonstrate the effectiveness of AB-101 across other pathogens and in particular across gram negative (−) pathogens, Lot 01 and 02 were tested against *Pseudomonas aeruginosa*. All 20 of the *Pseudomonas aeruginosa* tested are resistant to multiple antibiotics, thereby they all fit the definition of being Multi-Drug Resistant (MDR). Of the 20, 5 are known to be Verona integron-encoded metallo-beta-lactamase (VIM)—producing *Pseudomonas aeruginosa* which are drug resistant strains of *Pseudomonas aeruginosa*, another 5 are know to be *Klebsiella pneumoniae* carbapenemase (KPC) producing *Pseudomonas aeruginosa* strains which are drug resistant strains of *Pseudomonas aeruginosa*, and 4 are known to be IMP-Type Metallo-β-Lactamase (IMP))—producing *Pseudomonas aeruginosa* which are drug resistant strains of *Pseudomonas aeruginosa*. The 6 remaining strains are known to be antibiotic resistant and are listed simply as MDR strains. Measures included the minimum inhibitory concentration (MIC) which is the lowest concentration of AB-101 that prevents visible growth of the bacterium or pathogen, and minimum bactericidal concentration (MBC) which is the lowest concentration of an antibacterial agent required to kill a bacterium.

Table 15 shows the comparison of AB-101 Lot 01 and 02 for MIC demonstrates a high effectiveness against *Pseudomonas aeruginosa*. Shown for the first time is the effectiveness of AB-101 against these pathogens and importantly an improvement over the leading current pharmaceutical treatment.

TABLE 15

| *Pseudomonas aeruginosa* | *Pseudomonas aeruginosa* | MIC (% AB-101)[a] | | | | MIC (μg/mL)[b] | | | |
|---|---|---|---|---|---|---|---|---|---|
| Strain ID | Characteristic | Lot 1 | | Lot 2 | | Imipenem | | Ciprofloxacin | |
| CDC 0230 | VIM | 25 | 25 | 25 | 25 | >64 | >64 | >64 | >64 |
| CDC 0239 | VIM | 12.5 | 12.5 | 12.5 | 12.5 | >64 | >64 | 32 | 32 |
| CDC 0254 | VIM | 25 | 25 | 25 | 25 | >64 | >64 | 32 | 32 |
| CDC 0255 | VIM | 25 | 25 | 25 | 25 | >64 | >64 | 32 | 32 |
| CDC 0509 | VIM | 25 | 25 | 25 | 25 | >64 | >64 | 32 | 32 |
| CDC 0231 | KPC | 25 | 25 | 25 | 25 | >64 | >64 | >64 | >64 |
| CDC 0356 | KPC | 25 | 25 | 25 | 25 | >64 | >64 | 0.125 | 0.125 |
| CDC 0441 | KPC | 25 | 25 | 25 | 25 | >64 | >64 | 2 | 2 |
| CDC 0516 | KPC | 25 | 25 | 25 | 25 | >64 | >64 | 0.125 | 0.125 |
| CDC 0518 | KPC | 12.5 | 12.5 | 12.5 | 12.5 | >64 | >64 | >64 | >64 |
| CDC 0092 | IMP | 12.5 | 12.5 | 12.5 | 50 | >64 | >64 | 32 | 32 |
| CDC 0103 | IMP | 12.5 | 12.5 | 12.5 | 12.5 | >64 | >64 | >32 | >32 |
| CDC 0439 | IMP | 12.5 | 12.5 | 12.5 | 12.5 | >64 | >64 | 32 | 32 |
| CDC 0241 | IMP | 12.5 | 12.5 | 12.5 | 12.5 | >64 | >64 | 16 | 16 |

TABLE 15-continued

| *Pseudomonas aeruginosa* Strain ID | *Pseudomonas aeruginosa* Characteristic | MIC (% AB-101)[a] Lot 1 | | MIC (% AB-101)[a] Lot 2 | | MIC (μg/mL)[b] Imipenem | | MIC (μg/mL)[b] Ciprofloxacin | |
|---|---|---|---|---|---|---|---|---|---|
| CDC 0508 | MDR | 12.5 | 12.5 | 12.5 | 12.5 | 16 | 16 | 2 | 2 |
| CDC 0353 | MDR | 25 | 25 | 12.5 | 12.5 | 16 | 16 | 16 | 16 |
| CDC 0357 | MDR | 25 | 25 | 25 | 25 | 16 | 16 | 32 | 32 |
| CDC 0246 | MDR | 12.5 | 12.5 | 12.5 | 12.5 | >64 | >64 | 32 | 32 |
| CDC 0250 | MDR | 25 | 12.5 | 12.5 | 25 | >64 | >64 | 32 | 32 |
| CDC 0064 | MDR | 25 | 25 | 25 | 25 | >64 | >64 | 16 | 16 |
| ATCC 27853 | QC strain | 25 | 25 | 25 | 25 | 2 | 2 | 0.25 | 0.25 |

Table 16 shows the comparison of Iminipenem and Cripofloxacin for MIC against quality control strain ATCC 27853.

TABLE 16

| *Pseudomonas aeruginosa* Strain | CLSI QC Range MIC (μg/ml) Imipenem | CLSI QC Range MIC (μg/ml) Ciprofloxacin |
|---|---|---|
| ATCC 27853 | 1-4 | 0.125-1 |

Table 17 shows the comparison of AB-101 Lots 01 and 02 for MBC demonstrates a high effectiveness against *Pseudomonas aeruginosa*. Shown for the first time is the effectiveness of AB-101 against these pathogens specifically for the multi-drug resistant pathogens.

TABLE 17

| *Pseudomonas aeruginosa* screen number | *Pseudomonas aeruginosa* ID | *Pseudomonas aeruginosa* Characteristic | MBC (% AB-101) Lot 01 | | MBC (% AB-101) Lot 02 | |
|---|---|---|---|---|---|---|
| 1 | CDC 0230 | VIM | 25 | 25 | 25 | 25 |
| 2 | CDC 0239 | VIM | 25 | 25 | 25 | 25 |
| 3 | CDC 0254 | VIM | 25 | 25 | 25 | 25 |
| 4 | CDC 0255 | VIM | 25 | 25 | 25 | 25 |
| 5 | CDC 0509 | VIM | 25 | 25 | 25 | 25 |
| 6 | CDC 0231 | KPC | 25 | 25 | 25 | 25 |
| 7 | CDC 0356 | KPC | 25 | 25 | 25 | 25 |

TABLE 17-continued

| *Pseudomonas aeruginosa* screen number | *Pseudomonas aeruginosa* ID | *Pseudomonas aeruginosa* Characteristic | MBC (% AB-101) Lot 01 | | MBC (% AB-101) Lot 02 | |
|---|---|---|---|---|---|---|
| 8 | CDC 0441 | KPC | 25 | 25 | 25 | 25 |
| 9 | CDC 0516 | KPC | 25 | 25 | 25 | 25 |
| 10 | CDC 0518 | KPC | 25 | 25 | 25 | 25 |
| 11 | CDC 0092 | IMP | 25 | 25 | 25 | 50 |
| 12 | CDC 0103 | IMP | 25 | 25 | 25 | 25 |
| 13 | CDC 0439 | IMP | 25 | 25 | 25 | 25 |
| 14 | CDC 0241 | IMP | 25 | 12.5 | 25 | 25 |
| 15 | CDC 0508 | MDR | 50 | 50 | 25 | 25 |
| 16 | CDC 0353 | MDR | 25 | 25 | 25 | 25 |
| 17 | CDC 0357 | MDR | 25 | 25 | 25 | 25 |
| 18 | CDC 0246 | MDR | 50 | 12.5 | 25 | 50 |
| 19 | CDC 0250 | MDR | 25 | 25 | 25 | 25 |
| 20 | CDC 0064 | MDR | 25 | 25 | 25 | 25 |
| 21 | ATCC 27853 | QC strain | 25 | 25 | 25 | 25 |

AB-101 Lots 01, 02 and a purified extract of taspine for MIC are compared. The concentration of taspine at the highest concentration tested (i.e. 50%, relative to AB-101) is 10 μg/m L demonstrated for the first time from a bacteriologic perspective, taspine does not have activity as evaluated by this invitro test method against MSSA and MRSA. Taspine may have additional synergistic benefits to be included in the whole extract in the final product for the effective treatment of a bacterial colonization or primary or secondary bacterial infection of an underlying skin disorder. Results are shown in Table 18.

TABLE 18

| Strain ID | Characteristic | MIC (% vol./vol.) AB-101 Lot 01 | | MIC (% vol./vol.) AB-101 Lot 02 | | MIC (% relative to amount in AB-101) Taspine | | MIC (μg/mL) Methicillin | MIC (μg/mL) Mupirocin |
|---|---|---|---|---|---|---|---|---|---|
| CDC 218 | MupirocinR, MRSA | 12.5 | 12.5 | 12.5 | 12.5 | >50 | >50 | >64 | >256 |
| CDC 224 | MupirocinR, MRSA | 12.5 | 12.5 | 12.5 | 12.5 | >50 | >50 | >64 | >256 |
| CDC 228 | MupirocinR, MRSA | 3.13 | 3.13 | 3.13 | 3.13 | >50 | >50 | 64 | >256 |
| 1674606 | MupirocinR, MSSA | 50 | 50 | 50 | 50 | >50 | >50 | 2-8 | >256 |
| 1674607 | MupirocinR, MRSA | 12.5 | 12.5 | 12.5 | 12.5 | >50 | >50 | >64 | >256 |
| 1674608 | MupirocinR, MSSA | 12.5 | 12.5 | 25 | 50 | >50 | >50 | 2-4 | >256 |
| 1674611 | MupirocinR, MRSA | 6.25 | 6.25 | 12.5 | 12.5 | >50 | >50 | 64 | >256 |
| CDC 480 | MupirocinS, MRSA | 12.5 | 25 | 12.5 | 25 | >50 | >50 | 32-64 | ≤0.25 |
| CDC 481 | MupirocinS, MRSA | 12.5 | 12.5 | 12.5 | 12.5 | >50 | >50 | 16-32 | ≤0.25 |
| CDC 482 | MupirocinS, MRSA | 12.5 | 12.5 | 12.5 | 12.5 | >50 | >50 | 8-32 | ≤0.25 |
| CDC 483 | MupirocinS, MRSA | 12.5 | 12.5 | 12.5 | 12.5 | >50 | >50 | 64 | ≤0.25 |
| CDC 220 | MupirocinS, MRSA | 12.5 | 12.5 | 6.25 | 12.5 | >50 | >50 | 64->64 | ≤0.25 |
| CDC 227 | MupirocinS, MRSA | 6.25 | 6.25 | 12.5 | 12.5 | >50 | >50 | 64 | ≤0.25-0.5 |
| CDC 461 | MupirocinS, MSSA | 12.5 | 12.5 | 12.5 | 12.5 | >50 | >50 | 4-8 | ≤0.25-1 |
| CDC 462 | MupirocinS, MSSA | 6.25 | 12.5 | 6.25 | 12.5 | >50 | >50 | 8 | ≤0.25 |
| CDC 463 | MupirocinS, MSSA | 6.25 | 6.25 | 12.5 | 12.5 | >50 | >50 | 8-16 | ≤0.25-0.5 |

TABLE 18-continued

| Strain ID | Characteristic | MIC (% vol./vol.) AB-101 Lot 01 | | MIC (% vol./vol.) AB-101 Lot 02 | | MIC (% relative to amount in AB-101) Taspine | | MIC (μg/mL) Methicillin | MIC (μg/mL) Mupirocin |
|---|---|---|---|---|---|---|---|---|---|
| CDC 464 | MupirocinS, MSSA | 12.5 | 12.5 | 12.5 | 12.5 | >50 | >50 | 2 | ≤0.25 |
| CDC 484 | MupirocinS, MSSA | 12.5 | 12.5 | 12.5 | 12.5 | >50 | >50 | 2 | ≤0.25 |
| CDC 485 | MupirocinS, MSSA | 50 | 50 | 50 | 50 | >50 | >50 | 2-4 | ≤0.25 |
| ATCC 29213 | QC control | 12.5 | 50-12.5 | 12.5 | 12.5 | >50 | >50 | 1-2 | ≤0.25-0.5 |

AB-101 Lots 01, 02 and a purified extract of taspine for MBC are compared. Demonstrated for the first time from a bacteriologic perspective, taspine does not have activity as evaluated by this invitro test method against MSSA and MRSA. Taspine may have additional synergistic benefits to be included in the whole extract in the final product for the effective treatment of bacterial colonization or primary or secondary bacterial infection of an underlying skin disorder. Results are shown in Table 19.

TABLE 19

| Strain ID | Characteristic | MBC (% vol./vol.) AB-101 Lot 01 | | MBC (% vol./vol.) AB-101 Lot 02 | | MBC (% relative to amount in AB-101) Taspine | |
|---|---|---|---|---|---|---|---|
| CDC 218 | MupirocinR, MRSA | 50 | 50 | 50 | 50 | >50 | >50 |
| CDC 224 | MupirocinR, MRSA | 50 | 50 | 50 | 50 | >50 | >50 |
| CDC 228 | MupirocinR, MRSA | 6.25 | 6.25 | 6.25 | 6.25 | >50 | >50 |
| 1674606 | MupirocinR, MSSA | >50 | >50 | >50 | >50 | >50 | >50 |
| 1674607 | MupirocinR, MRSA | 12.5 | 12.5 | 25 | 25 | >50 | >50 |
| 1674608 | MupirocinR, MSSA | 50 | 50 | 50 | >50 | >50 | >50 |
| 1674611 | MupirocinR, MRSA | 12.5 | 12.5 | 50 | 50 | >50 | >50 |
| CDC 480 | MupirocinS, MRSA | 50 | 50 | 50 | 50 | >50 | >50 |
| CDC 481 | MupirocinS, MRSA | 50 | 50 | 50 | 50 | >50 | >50 |
| CDC 482 | MupirocinS, MRSA | 50 | 50 | 50 | 50 | >50 | >50 |
| CDC 483 | MupirocinS, MRSA | 50 | 50 | 50 | 50 | >50 | >50 |
| CDC 220 | MupirocinS, MRSA | 25 | 25 | 25 | 25 | >50 | >50 |
| CDC 227 | MupirocinS, MRSA | 12.5 | 12.5 | 25 | 25 | >50 | >50 |
| CDC 461 | MupirocinS, MSSA | 50 | 50 | 50 | 50 | >50 | >50 |
| CDC 462 | MupirocinS, MSSA | 12.5 | 50 | 50 | 50 | >50 | >50 |
| CDC 463 | MupirocinS, MSSA | 12.5 | 12.5 | 12.5 | 12.5 | >50 | >50 |
| CDC 464 | MupirocinS, MSSA | >50 | 50 | 50 | 50 | >50 | >50 |
| CDC 484 | MupirocinS, MSSA | 50 | 50 | 50 | 50 | >50 | >50 |
| CDC 485 | MupirocinS, MSSA | 50 | 50 | 50 | 50 | >50 | >50 |
| ATCC 29213 | QC control | 50-12.5 | 50-12.5 | 50 | 50 | >50 | >50 |

Example 4

Ten patients with 18 MRSA drug resistant skin infections (1 pressure ulcer and 17 lesions defined as cuts and scrapes secondarily infected with MRSA) have been treated with AB-101. Current treatments for drug resistant skin infections include topical, oral, intravenous (IV) drugs, and combinations of these when single drug therapy fails. Each of these treatments exhibits problems beginning with failure to cure the infection (i.e. bacterial resistance to the drug), hospitalization, expensive combination drug therapies, risk of death, whole body drug exposure (potentiating further bacterial drug resistance), multiple varied side effects and slow wound healing.

All MRSA infections were cultured and verified by the patient's physicians.

Patient 1, an elderly female patient in an extended care facility was diagnosed with a chronic Mupirocin-resistant MRSA-infected ulcer, and was switched from Mupirocin to AB-101 6% ointment delivery. The staff was instructed to apply the ointment twice daily to the ulcer, and measure the ulcer size 3 times a week. Over a period of 4 weeks the measurement of the lesion size decreased to the point where the ulcer was almost completely healed and the lesion was not measurable.

Patient 2, an adult female subject was exposed to MRSA through another infected individual from a wrestling tournament and diagnosed with 3 infected lesions. She signed a consent form and was given a 1 ounce bottle of AB-101 (undiluted liquid; 100% concentration) and written instructions to apply a drop to her lesion 3 times daily and rub it gently over the lesion until dry. Nineteen days later her 3 lesions were healed and the MRSA infection eradicated.

Patient 3, an adult male subject was exposed to MRSA through another infected individual from a wrestling tournament and diagnosed with 3 infected lesions. He signed a consent form and was given a 1 ounce bottle of AB-101 (undiluted liquid; 100% concentration) and written instructions to apply a drop to his lesion 3 times daily and rub it gently over the lesion until dry. Twelve days later his 3 lesions were healed and the MRSA infection eradicated.

Patient 4, a teenage male subject was exposed to MRSA through another infected individual from a wrestling tournament and diagnosed with 5 infected lesions. He and his parent signed a consent form and was given a 1 ounce bottle of AB-101 (undiluted liquid; 100% concentration) and written instructions to apply a drop to his lesion 3 times daily and rub it gently over the lesion until dry. Twenty days later his 5 lesions were healed and the MRSA infection eradicated.

Six additional teenage male patients, patients 5 through 10, were diagnosed with 1 MRSA infected lesion each. All patients (or their parent or guardian if the patient was a minor) signed a consent form and were given a 1-ounce bottle of AB-101 (undiluted liquid, 100% concentration) with written instructions to apply 1 drop to each lesion 3 times daily and rub it gently over the lesion until dry. Patients 5-10's lesions were healed and the MRSA infections eradicated within 21 days.

No patient reported drug resistance, any side effects, pain, scarring, slow wound healing, hospitalization or combination therapy as a result of AB-101 use. Use of AB-101 resulted in no reported or observed irritation, hypersensitivity or photosensitivity.

Table 20 presents AB-101 human primary and secondary outcomes and final assessments in MRSA drug resistant skin infections for the 10 patients in this report.

TABLE 20

| Patient Demographics | Diagnosis | Treatment | Primary Outcome/ Response | Secondary Outcomes | Final Assessment |
|---|---|---|---|---|---|
| Patient 1: Elderly female | 1 MRSA Pressure ulcer Bactroban ® Resistant | MRSA-1 Ointment: 3× Daily to affected area | Lesion eradicated After 4 weeks of treatment | Did not report: whole body drug exposure, drug resistance, side effects, pain, scarring, slow wound healing, hospitalization, combination drug treatment | Complete Response |
| Patient 2: Adult female | 3 MRSA lesions | MRSA-1 Liquid: 3× Daily to affected area | All lesions eradicated After 19 days of treatment | Did not report: whole body drug exposure, drug resistance, side effects, pain, scarring, slow wound healing, hospitalization, combination drug treatment | Complete Response |
| Patient 3: Adult male | 3 MRSA lesions | MRSA-1 Liquid: 3× Daily to affected area | All lesions eradicated After 12 days of treatment | Did not report: whole body drug exposure, drug resistance, side effects, pain, scarring, slow wound healing, hospitalization, combination drug treatment | Complete Response |
| Patient 4: Teenage male | 5 MRSA lesions | MRSA-1 Liquid: 3× Daily to affected area | All lesions eradicated After 20 days of treatment | Did not report: whole body drug exposure, drug resistance, side effects, pain, scarring, slow wound healing, hospitalization, combination drug treatment | Complete Response |
| Patient 5: Teenage male | 1 MRSA lesion | MRSA-1 Liquid: 3× Daily to affected area | All lesion(s) eradicated After 21 days of treatment | Did not report: whole body drug exposure, drug resistance, side effects, pain, scarring, slow wound healing, hospitalization, combination drug treatment | Complete Response |
| Patient 6: Teenage male | 1 MRSA lesion | MRSA-1 Liquid: 3× Daily to affected area | All lesion(s) eradicated After 21 days of treatment | Did not report: whole body drug exposure, drug resistance, side effects, pain, scarring, slow wound healing, hospitalization, combination drug treatment | Complete Response |
| Patient 7: Teenage male | 1 MRSA lesion | MRSA-1 Liquid: 3× Daily to affected area | All lesion(s) eradicated After 21 days of treatment | Did not report: whole body drug exposure, drug resistance, side effects, pain, scarring, slow wound healing, hospitalization, combination drug treatment | Complete Response |
| Patient 8: Teenage male | At least 1 MRSA lesion | MRSA-1 Liquid: 3× Daily to affected area | All lesion(s) eradicated After 21 days of treatment | Did not report: whole body drug exposure, drug resistance, side effects, pain, scarring, slow wound healing, hospitalization, combination drug treatment | Complete Response |
| Patient 9: Teenage male | At least 1 MRSA lesion | MESA-1 Liquid: 3× Daily to affected area | All lesion(s) eradicated After 21 days of treatment | Did not report: whole body drug exposure, drug resistance, side effects, pain, scarring, slow wound healing, hospitalization, combination drug treatment | Complete Response |
| Patient 10: Teenage male | At least 1 MRSA lesion | MRSA-1 Liquid: 3× Daily to affected area | All lesion(s) eradicated After 21 days of treatment | Did not report: whole body drug exposure, drug resistance, side effects, pain, scarring, slow wound healing, hospitalization, combination drug treatment | Complete Response |

AB-101 human results for irritation, hypersensitivity and photosensitivity in MRSA drug resistant skin infections for the 10 patients of this report are presented in Table 21.

TABLE 21

| Patient Demographics | Irritation | Hypersensitivity | Photosensitivity |
|---|---|---|---|
| Patient 1: Elderly female | No irritation observed or reported | No hypersensitivity observed or reported | No photosensitivity observed or reported |
| Patient 2: Adult female | No irritation observed or reported | No hypersensitivity observed or reported | No photosensitivity observed or reported |
| Patient 3: Adult male | No irritation observed or reported | No hypersensitivity observed or reported | No photosensitivity observed or reported |
| Patient 4: Teenage male | No irritation observed or reported | No hypersensitivity observed or reported | No photosensitivity observed or reported |
| Patient 5: Teenage male | No irritation observed or reported | No hypersensitivity observed or reported | No photosensitivity observed or reported |
| Patient 6: Teenage male | No irritation observed or reported | No hypersensitivity observed or reported | No photosensitivity observed or reported |
| Patient 7: Teenage male | No irritation observed or reported | No hypersensitivity observed or reported | No photosensitivity observed or reported |
| Patient 8: Teenage male | No irritation observed or reported | No hypersensitivity observed or reported | No photosensitivity observed or reported |
| Patient 9: Teenage male | No irritation observed or reported | No hypersensitivity observed or reported | No photosensitivity observed or reported |
| Patient 10: Teenage male | No irritation observed or reported | No hypersensitivity observed or reported | No photosensitivity observed or reported |

The 10 patients reported here demonstrated the efficacy for AB-101 in treating MRSA drug resistant skin infections and that use of AB-101 eliminated the significant problems of current treatments for MRSA drug resistant skin infections.

Example 5—IVPT and IVRT Studies with AB-101

The design of a topical treatment to fight acute or chronic skin conditions is fundamentally different than systemic treatments either for bacterial or viral. An effective topical antibiotic has different performance constraints and designed formulation targets that need to be optimized for efficacy while maximizing safety.

From an efficacy standpoint, the antibiotic needs to be effective against the pathogens causing infection, blisters, lesions, or other distressing skin conditions such as itching, inflammation, irritation or causing skin disrepair such as flaking, skin and rashes to name just a few common skin conditions associated with dermatologic conditions associated with common topical pathogens. To promote efficacy the antibiotic formulation must readily release the active antibiotic agent and ideally the antibiotic agent should readily remain available on the surface of the wound.

The In vitro Permeation Test (IVPT) and the In Vitro Release Test (IVRT) are two critical product tests that are common to those skilled in the art to evaluate topical drugs. Both tests are measurements of the Active Pharmaceutical Ingredient (API) using the Franz diffusion cells and a non-interactive synthetic membrane or skin is used to analyze a range of semi-solid dosage forms. The measurement unit for IVPT and IVRT is flux as measured in units of $\mu g/cm^2$ over time.

Figure 10:
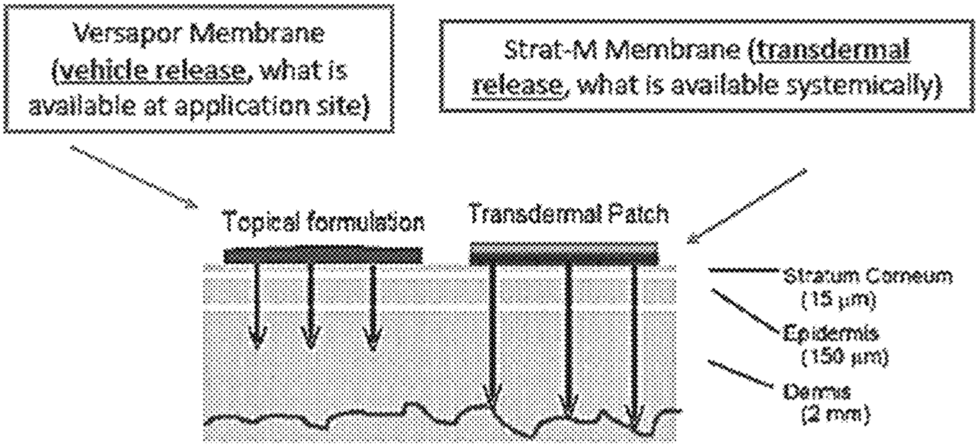
FIG. 10 depicts the distinction of IVPT and IVRT and the specific membranes used to measure these properties.

The IVPT or skin permeation testing is a critical tool for understanding drug delivery into the various layers of skin and can aid in formulation selection. The IVRT measures the release rate of a drug from the API carrier. For a topical drug the ideal condition is for the API to have minimum permeation into the layers of the skin and have maximum release of the API from the carrier. FIG. 10 below shows graphically the distinction of IVPT and IVRT and the specific membranes used to measure these properties.

Skin Permeation and Product Release from the Hydrogel Vehicle: These experiments were designed to assess the in vitro skin permeation and vehicle release of AB-101 API's catechin, epicatechin, gallocatechin, epigallocatechin, and taspine from AB-101 100% and/or AB-101/hydrogel formulations. In vitro testing such as this is an accepted, industry-standard method for determining the skin penetration of a topically applied products (USP Chapter 1724, USP 36/NF31, 2013), and in vitro testing using Strat-M membranes has been shown to be predictive of in vivo results (Flaten et al, 2005) of permeation and the Versapor membrane is predictive of in vivo release from the vehicle (hydrogel). The Franz diffusion cell model is a well establish industry and academic method for performing permeation testing (Ueda et al, 2009; Li & Rahn, 1993) and API vehicle release. The biomarker compounds of the AB-101 API are catechin (C), epicatechin (EC), gallocatechin (GC), epigallocatechin (EGC), and taspine (T). To determine the flux of catechin, epicatechin, gallocatechin, epigallocatechin, and taspine into and through the skin, an existing analytical LC-MS/MS method was used.

IVPT data revealed poor transdermal permeation of these biomarker compounds from either AB-101 100% or AB-101 hydrogel formulations. As defined by flux, AB-101 lots (X and 1) demonstrated low amounts permeating for all 5 compounds tested. Additionally, hydrogel testing revealed decreasing rate of permeant crossing the membrane and less accumulation of the compounds with increasing % AB-101 in hydrogel (Table 22).

TABLE 22

| Flux Calculations | | | | | |
|---|---|---|---|---|---|
| Vehicle | C | EC | GC | EGC | T |
| Lot 1 | 8.82 | 9.11 | 18.25 | 503.51 | 10.01 |
| Lot X | 1.53 | 1.04 | 4.33 | 57.09 | 16.69 |
| 20% | 0.80 | 0.78 | 0.65 | 11.46 | 2.19 |

TABLE 22-continued

| Flux Calculations | | | | | |
|---|---|---|---|---|---|
| Vehicle | C | EC | GC | EGC | T |
| 30% | 0.44 | 0.48 | 0.36 | 5.82 | 1.75 |
| 40% | 0.21 | 0.27 | 0.18 | 1.86 | 1.99 |
| 50% | 0.00 | 0.00 | 0.00 | 0.00 | 1.93 |

Flux (J): μg/$cm^2$/hr.
Flux is the amount of permeant crossing a membrane per unit time
J = Q/(A * t)
Q = [compound]
A = area of membrane
T = time This data shows a powerful inverse relationship between the dosing concentration and the permeation flux: specifically, as dosing concentration increases, permeation decreases. This is not obvious relationship and is in contrast with the majority of drug delivery systems where increase dosing concentration either maintains or increases permeation resulting in an adverse safety and efficacy profile. There are two key advantages of this performance relationship that are extremely beneficial for topical drug delivery. The first advantage is that the maximum AB-101 API level can be dosed to maximize bacterial pathogen kill. One of the sources for drug resistance is the fact that the bacteria is not completely killed. Part of the reason for this is that the dose level was limited for safety reasons. The second advantage is due to the fact that the API AB-101 drug is not or minimally absorbed by the wound, skin or vascular system. This means that the API stays in the lesion for the duration of treatment ensuring maximum contact of the AB-101 API with the bacteria pathogen. Beyond the efficacy benefit this shows an unexpected and desirable safety advantage based on the fact the AB-101 API will stay on the surface and in the wound and not be absorbed by the vascular system.

IVRT data reveal excellent release of the of these biomarker compounds from either AB-101 100% or AB-101 hydrogel formulations. As defined by flux, AB-101 lots (X and 1) demonstrated high amounts of the API across Versapor membrane for all 5 compounds tested. Additionally, hydrogel testing revealed increasing rate of AB-101 API release crossing the membrane and as the concentration of AB-101 increases in the hydrogel vehicle, proportionately more of the compounds with increasing % AB-101 in hydrogel is released (Table 23). This shows that the hydrogel vehicle does not retain or inhibit the delivery of AB-101 to the site of infection or wound. This confirms that AB-101 delivery efficacy to treat bacterial pathogens.

TABLE 23

| Flux Calculations IVRT | | | | | |
|---|---|---|---|---|---|
| Vehicle | C | EC | GC | EGC | T |
| Lot 1 | 169.6 | 143.8 | 251.1 | 2454.3 | 723.2 |
| Lot X | 84.0 | 51.6 | 115.9 | 308.7 | 591.1 |
| 20% hydrogel | 31.3 | 30.0 | 46.9 | 471.0 | 136.6 |
| 30% hydrogel | 40.7 | 40.2 | 78.5 | 727.5 | 211.0 |
| 40% hydrogel | 68.9 | 57.0 | 114.1 | 983.1 | 273.1 |
| 50% hydrogel | 88.1 | 68.7 | 130.0 | 1430.6 | 381.0 |

Flux (J): μg/$cm^2$/hr.
Flux is the amount of permeant crossing a membrane per unit time
J = Q/(A * t)
Q = [compound]
A = area of membrane
T = time Example 6—Log P Studies with AB-101

Log P is an assessment of a molecule's lipophilicity, indicating how readily an analyte can partition between aqueous and organic phases. When a topical drug possesses poor lipophilicity, with Log P rating of −1 to 2 (Table 24), when it is applied to the skin the topical drug will not penetrate or disperse easily into the skin. To reach high systemic levels, a topical drug must be permeable enough, which is defined as lipophilic enough, to partition into the lipid bilayer of the skin, but, not so lipophilic that once it is in the skin bilayer it will stay sequestered there. Lipophilicity plays a major role in determining where drugs are distributed within the body after absorption into tissues and, as a consequence, in how rapidly they are metabolized and excreted.

TABLE 24

| LogP Rating Scale and Values | | | | | | | |
|---|---|---|---|---|---|---|---|
| LogP: | | | | | | | |
| −1.0 | 0.0 | 1.0 | 2.0 | 3.0 | 4.0 | 5.0 | 6.0 |
| z | z | z | z | z | z | z | z |
| Limited permeability, poor lipid solubility, poor skin absorption and distribution. | | | | Intermediate permeability, able to cross the skin lipid bilayer but not be sequestered in the skin | | Highly permeable, crosses into skin and stays sequestered in skin | |

The Log P value is a constant defined in the following manner: Log P=log 10 (Partition Coefficient) Partition Coefficient, P=[organic]/[aqueous] Where [ ] indicates the concentration of solute in the organic and aqueous partition. A negative value for log P means the compound has a higher affinity for the aqueous phase (it is more hydrophilic); when log P=0 the compound is equally partitioned between the lipid and aqueous phases; a positive value for log P denotes a higher concentration in the lipid phase (i.e., the compound is more lipophilic). Log P=1 means there is a 10:1 partitioning in Organic: Aqueous phases. Although log P is a constant, its value is dependent on the choice of the organic partitioning solvent and, to a lesser degree, on the conditions of measurement. AB-101 partition coefficient was determined using water and n-Octanol.

The partitioning assays reported here (Table 25) determined the in vitro partitioning and release of AB-101's five selected components (the four PAC's catechin, epicatechin, epigallocatechin, gallocatechin, plus taspine) from four different AB-101 forms: (1) AB-101 100% from AB-101 batches 0, 1, 2 and X, (2) AB-101 100% from batches 0, 1, 2 and X after they were lyophilized and resuspended in water to determine the impact on partitioning of the lyophilization and resuspension processes in the event these processes are utilized in commercial production, and, (3 & 4) two AB-101 hydrogel formulations (AB-101 at 20% and AB-101 at 50%) both from AB-101 batch 1. These data report poor lipophilicity of all five selected AB-101 components (the PAC's and taspine) as defined by Log P analysis for all four forms tested. As the skin is lipophilic, the AB-101 PAC's and taspine and the other compounds of AB-101 being poorly lipophilic will not penetrate or disperse easily into the skin when applied directly to the skin. Lack of lipophilicity further demonstrates the AB-101 PAC's and taspine and the other compounds of AB-101 will not be passed through the skin into the underlying tissues or systemic circulation. The AB-101 PAC's and taspine AB-101 poor skin and tissue penetration demonstrates their limited ability to be absorbed into the skin resulting in even lower likelihood they will pass through the skin to reach systemic circulation or other tissued or organs. If any of the AB-101 PAC's or taspine do reach systemic circulation, their poor tissue penetration means they will not be accumulated in tissues and will be excreted from the body.

TABLE 25

LogP Values for specified components of AB-101 in Four Forms: AB-101 100%, AB-101 100% Resuspended and Two AB-101 Hydrogel Formulations LogP Values

| AB-101 Form | AB-101 Batch # | LogP Catechin[1] (0.51-1.8) [2] | LogP Epicatechin[1] (0.4-1.8) [2] | LogP Gallocatechin[1] (0.71-1.41) [2] | LogP Epigallocatcchin[1] (0.00-1.49) [2] | LogP Taspin[1] (0.99-2.49) [2] |
|---|---|---|---|---|---|---|
| AB-101, 100% | Batch 0 | 0.27 | −0.09 | −0.24 | −0.79 | −1.15 |
| Lyophilized & Resuspended | | 0.39 | 0.02 | 0.36 | 1.20 | −1.06 |
| AB-101, 100% | Batch 1 | 0.29 | −0.02 | 0.01 | 0.27 | −1.76 |
| Lyophilized & Resuspended | | 0.23 | 0.02 | −0.13 | −0.11 | −0.94 |
| AB-101, 100% | Batch 2 | 0.59 | 0.13 | 0.56 | 0.86 | −0.90 |
| Lyophilized & Resuspended | | 0.07 | −0.17 | −0.48 | −1.71 | −1.71 |
| AB-101, 100% | Batch X | −0.14 | 0.07 | 0.03 | 1.82 | −0.31 |
| Lyophilized & Resuspended | | −0.13 | 0.09 | −025 | −0.55 | −0.07 |
| AB-101, 20% Hydrogel | Batch 1 | −0.49 | 0.39 | 0.37 | −0.46 | −1.35 |
| AB-101, 20% Hydrogel | Batch 1 | 0.62 | 0.89 | 0.93 | 0.84 | −084 |

[1]LogP values for reference standard PACs and Taspine do not significantly differ from PACs and Taspine from AB-101 tested in multiple forms

[2] Reference standard LogP values from ALOGPS, ChemAxon, Chemspider

Determination of Log P for AB-101 100% and its five selected components in four different forms resulted in consistent low Log P values at the level where none of these compounds will be absorbed into the skin or transported through the skin to become systemic. The low Log P values further demonstrate that if AB-101 reached systemic circulation it will not be absorbed in tissues and will be excreted. This analysis demonstrates a strong safety profile for AB-101.

The AB-101 testing in the IVPT, IVRT and log P taken as a whole, shows for the first time unique and outstanding safety profile and efficacy performance relationship with dosing concentrations.

Summary of the Results of Examples 5 and 6

Taken together, the results indicate that the 4 proanthocyanidins and taspine demonstrate low accumulation, flux and permeability across intact synthetic membranes. Any permeation that does occur would be unlikely to distribute at significant levels due to the poor distribution properties revealed from the in vitro Log P analysis. The results of these studies support the claim that the 4 proanthocyanidins and taspine measured are unlikely to reach toxic amounts at a systemic level based on these in vitro results.

When AB-101 is applied to an open wound the goal is to have very little absorption or partitioning into the wound and blood stream. This provides the Pharmaceutical grade of AB-101 with a strong safety profile. The data support the conclusion that the likelihood of topical AB-101 permeating the skin layers in any appreciable amount is extremely low. The data also indicate that any AB-101 that penetrates the skin will likely be metabolized within the skin prior to having an opportunity for systemic absorption. Furthermore, the likelihood of the AB-101 constituents being absorbed systemically were they to penetrate is also low given the log P values, which predict little or no passage. Shown for the first time is a pharmaceutical grade AB-101 that has both low permeability to enter into the blood stream and be absorbed by the tissue and organs leading to a safety concern.

For treatment of topical injuries there are at least four types of bacteria pathogens that a topical drug needs to be effective against. They include Methicillin-susceptible *Staphylococcus aureus* (MSSA), Methicillin-resistant *Staphylococcus aureus* (MRSA), *Pseudomonas aeruginosa* and *Streptococcus pyogenes*. Pharmaceutical grade AB-101 is effective against all of these pathogens.

Tables 26 and 27 show an assay whose setup is same as what was used for screening *S. aureus* and *P. aeruginosa* (i.e. 2-fold microdilution). The 20 strains of *S. pyogenes* assayed were selected from the two rounds of antibiotic screening to identify Erythromycin and Tetracycline resistant strains. The only difference from previous AB-101 MIC/MBC assay setup is that the broth used is CAMHB supplemented with 2.5% laked horse blood, plating for MIC/MBC was on Tryptic Soy Agar (TSA) with 5% defibrinated sheep blood, and incubation was done at 37° C., 5% $CO_2$ overnight, as per Clinical and Laboratory Standards Institute recommendation for beta-hemolytic *Streptococcus*. For this feasibility study, AB-101 Lot 1 and Lot 2 was used. *P. aeruginosa* ATCC 27853 was tested as a positive control for AB-101 activity. For the first time AB-101 has demonstrated effectiveness against the *S. aureus* pathogen and effectiveness against Erythromycin and Tetracycline resistant strains.

TABLE 26

*S. pyogenes* AB-101 Lot 1 MIC/MBC Results

| Pathogen | | AB-101 Lot 1 | | | | MIC (μg/mL) | | | |
|---|---|---|---|---|---|---|---|---|---|
| Species | Strain ID | MIC (%) | | MBC (%) | | Erythromycin | Tetracycline | Mupirocin | Vancomycin |
| *S. pyogenes* | 1744264 | 6.25 | 6.25 | 6.25 | 6.25 | 2 | 0.25 | 0.25 | 0.5 |
| | 1744265 | 50 | 50 | >50 | 50 | >16 | 8 | 0.5 | 8 |
| | 1744271 | 6.25 | 6.25 | 6.25 | 6.25 | >16 | 16 | 0.5 | 0.5 |
| | 1744272 | 6.25 | 6.25 | 6.25 | 6.25 | >16 | 8 | 0.25 | 1 |
| | 1744275 | 3.125 | 3.125 | 3.125 | 6.25 | >16 | 0.25 | ≤0.125 | 0.25-0.5 |
| | 1744277 | 6.25 | 6.25 | 6.25 | 6.25 | 0.5 | 0.25 | ≤0.125 | 4 |
| | 1744285 | 3.125 | 3.125 | 3.125 | 3.125 | >16 | >16 | ≤0.125 | 0.5 |
| | 20658748 | 6.25 | 6.25 | 6.25 | 6.25 | 2 | 16 | ≤0.125 | 0.25-0.5 |
| | 20658749 | 3.125 | 3.125 | 3.125 | 3.125 | 1 | 16 | ≤0.125 | 0.5 |
| | 20658750 | 3.125 | 6.25 | 3.125 | 6.25 | 1 | >16 | ≤0.125 | 0.5 |
| | 2065754 | 3.125 | 6.25 | 3.125 | 6.25 | >16 | 16 | ≤0.125 | 0.5 |
| | 2065755 | 3.125 | 3.125 | 3.125 | 3.125 | 2 | >16 | ≤0.125 | 0.5 |
| | 2065756 | 3.125 | 6.25 | 3.125 | 6.25 | 2 | >16 | ≤0.125 | 0.5 |
| | 2065757 | 3.125 | 3.125 | 3.125 | 3.125 | >16 | 16 | ≤0.125 | 0.5 |
| | 2065759 | 3.125 | 3.125 | 3.125 | 3.125 | 4 | 16->16 | ≤0.125 | 0.5 |
| | 2065760 | 6.25 | 1.56 | 6.25 | 6.25 | 2 | >16 | ≤0.125 | 0.5 |
| | 2065761 | 3.125 | 3.125 | 3.125 | 6.25 | >16 | 16->16 | ≤0.125 | 0.5 |
| | 2065762 | 3.125 | 3.125 | 3.125 | 3.125 | 2 | >16 | ≤0.125 | 0.5 |
| | 2065763 | 3.125 | 3.125 | 3.125 | 6.25 | 2 | 16->16 | ≤0.125 | 0.5 |
| | 2065765 | 6.25 | 6.25 | 6.25 | 6.25 | >16 | 2-4 | ≤0.125 | 2-4 |
| *P. aeruginosa* | ATCC 27853 | 12.5 | 12.5 | 12.5 | 12.5 | | | | |

TABLE 27

*S. pyogenes* AB-101 Lot 2 MIC/MBC Results

| Pathogens | | AB-101 Lot 2 | | | | MIC (μg/mL) | | | |
|---|---|---|---|---|---|---|---|---|---|
| Species | Strain ID | MIC (%) | | MBC (%) | | Erythromycin | Tetracycline | Mupirocin | Vancomycin |
| *S. pyogenes* | 1744264 | 6.25 | 6.25 | 6.25 | 6.25 | 2 | 0.25 | 0.25 | 0.5 |
| | 1744265 | >50 | >50 | >50 | >50 | >16 | 8 | 0.5 | 8 |
| | 1744271 | 6.25 | 6.25 | 12.5 | 12.5 | >16 | 16 | 0.5 | 0.5 |
| | 1744272 | 6.25 | 6.25 | 6.25 | 6.25 | >16 | 8 | 0.25 | 1 |
| | 1744275 | 6.25 | 6.25 | 6.25 | 6.25 | >16 | 0.25 | ≤0.125 | 0.25-0.5 |
| | 1744277 | 6.25 | 6.25 | 6.25 | 6.25 | 0.5 | 0.25 | ≤0.125 | 4 |
| | 1744285 | 6.25 | 6.25 | 6.25 | 6.25 | >16 | >16 | ≤0.125 | 0.5 |
| | 20658748 | 6.25 | 6.25 | 6.25 | 6.25 | 2 | 16 | ≤0.125 | 0.25-0.5 |
| | 20658749 | 6.25 | 6.25 | 6.25 | 6.25 | 1 | 16 | ≤0.125 | 0.5 |
| | 20658750 | 6.25 | 6.25 | 6.25 | 6.25 | 1 | >16 | ≤0.125 | 0.5 |
| | 2065754 | 6.25 | 6.25 | 6.25 | 6.25 | >16 | 16 | ≤0.125 | 0.5 |
| | 2065755 | 6.25 | 6.25 | 6.25 | 6.25 | 2 | >16 | ≤0.125 | 0.5 |
| | 2065756 | 6.25 | 6.25 | 6.25 | 6.25 | 2 | >16 | ≤0.125 | 0.5 |
| | 2065757 | 6.25 | 6.25 | 6.25 | 6.25 | >16 | 16 | ≤0.125 | 0.5 |
| | 2065759 | 6.25 | 6.25 | 6.25 | 6.25 | 4 | 16->16 | ≤0.125 | 0.5 |
| | 2065760 | 6.25 | 6.25 | 6.25 | 6.25 | 2 | >16 | ≤0.125 | 0.5 |
| | 2065761 | 6.25 | 6.25 | 6.25 | 6.25 | >16 | 16->16 | ≤0.125 | 0.5 |
| | 2065762 | 6.25 | 6.25 | 6.25 | 6.25 | 2 | >16 | ≤0.125 | 0.5 |
| | 2065763 | 6.25 | 6.25 | 6.25 | 6.25 | 2 | 16->16 | ≤0.125 | 0.5 |
| | 2065765 | 6.25 | 6.25 | 6.25 | 6.25 | >16 | 2-4 | ≤0.125 | 2-4 |
| *P. aeruginosa* | ATCC 27853 | 12.5 | 12.5 | 25 | 25 | | | | |

Example 7—Polydispersity Index Analysis of AB-101

To determine the PDI, an HPLC-UV method using gel permeation chromatography (GPC) and/or size exclusion (SEC) chromatography for this polymer analysis was developed. The polymer size distribution is calculated using the following equation: PDI=$M_w/M_n$, where $M_w$ is weight average molecular weight and $M_n$ is the number of the average molecular weight.

Sample Preparation: AB-101 was prepared by aliquoting 5 mL of material and lyophilizing the samples overnight. Samples were then weighed out and re-suspended in water at a concentration of 5 mg/mL. Samples were then diluted in water prior to GPC-UV/CAD analysis for PDI determination. Details of the HPLC method are below:

Column: Jordi Resolve columns 5 μm (7.8 mm ID×300 mm L), Porosity: 500 Å

HPLC Conditions: Isocratic: Dimethylformamide (DMF)

Flow rate: 0.7 mL/min

Injection volume: 20 μL

Column temperature: 40° C.

Detection: CAD

Standards: Polymethyl methacrylate (PMMA) EasiVials (Agilent)

Figure 11:
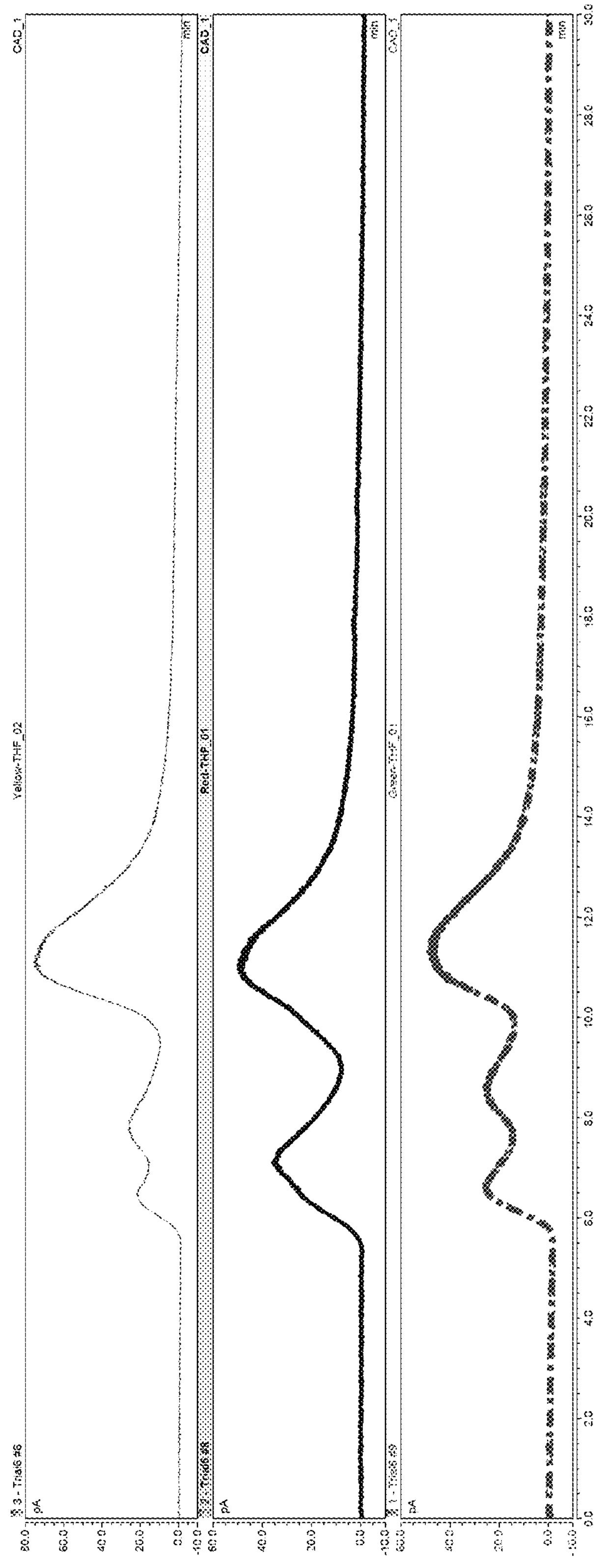
FIG. 11 depicts the gel permeation chromatogram of each of the 3 PMMA standards.
Figure 12:
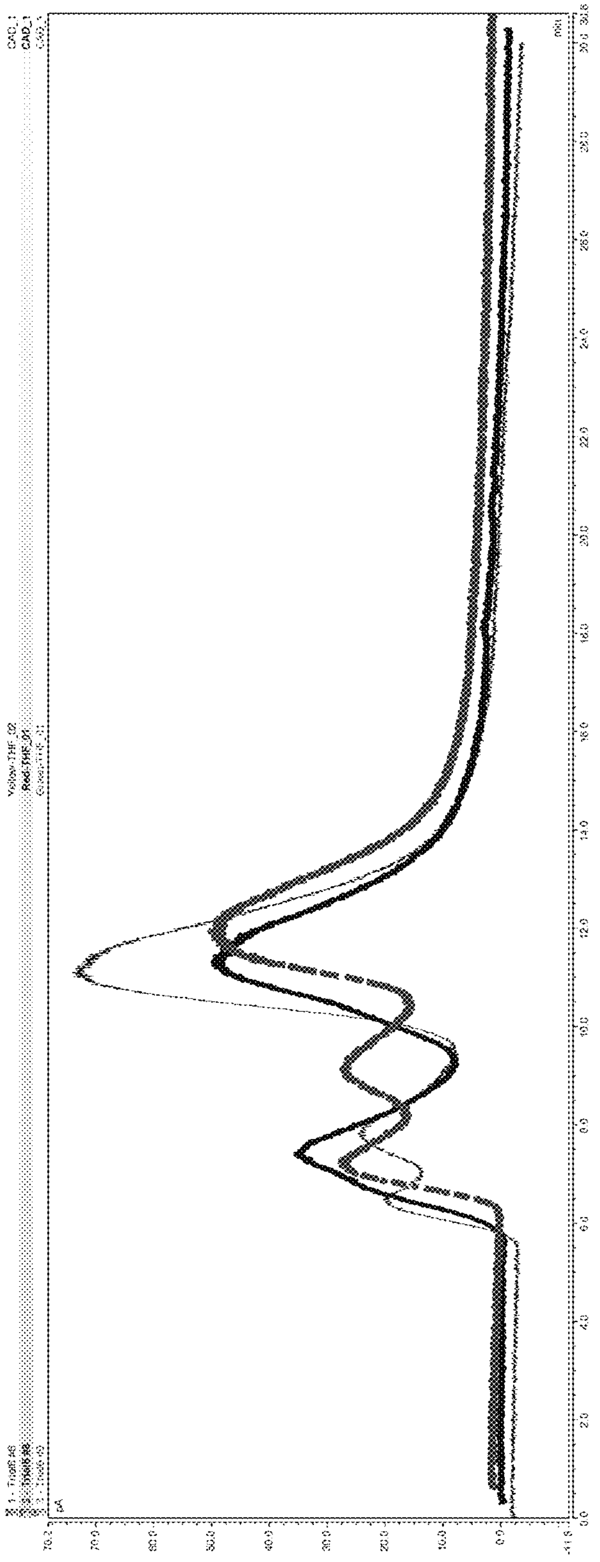
FIG. 12 depicts the overlay of the gel permeation chromatogram of the 3 PMMA standards.
Figure 13:
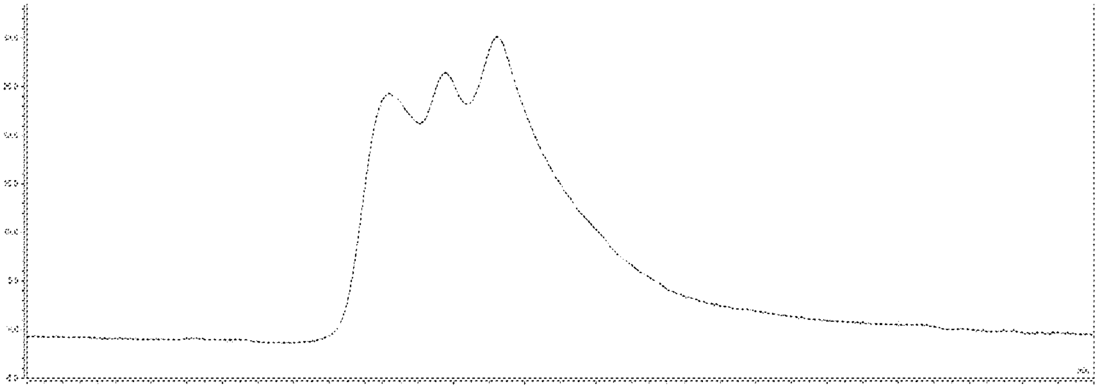
FIG. 13 depicts the AB-101 Lot 01 chromatograms at a 1.25 mg/mL concentration.

FIGS. 11 and 12 show the gel permeation chromatogram of 3 PMMA standards analyzed and now being detected. Top line is standard Yellow. Thicker line in the middle is standard Red. Dashed line on the bottom is standard Green. These standards were run at 2 mg/mL. The chromatograph demonstrated discerning peaks that enables calculation of PDI. FIG. 13 depicts the AB-101 Lot 01 chromatograms at a 1.25 mg/mL concentration.

Figure 14A:
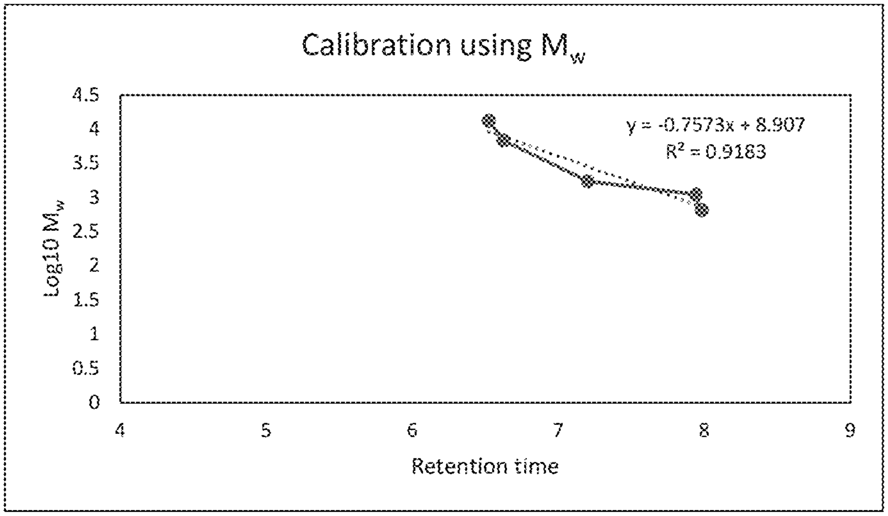
FIG. 14A depicts the calibration curve for $M_w$.
Figure 14B:
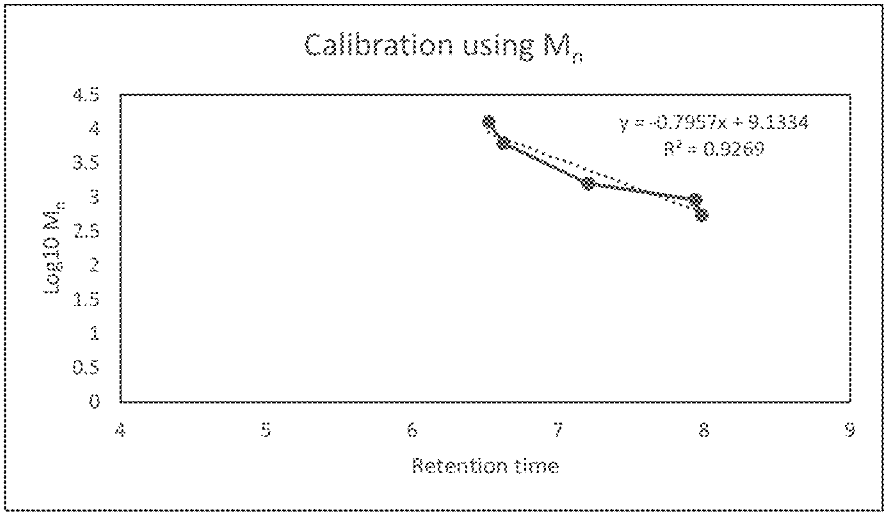
FIG. 14B depicts the calibration curve for $M_n$.

Polydispersity Index Calculations: Sample analysis for AB-101 Lot 01 using the developed method was performed. Calibration curves were generated based on Log $M_w$ vs. retention time and Log $M_n$ vs. retention time. The calibration curves are shown in FIGS. 13A and 14B. Using the calibration curves, the PDI was able to calculate the $M_w$ and $M_n$ values from AB-101 Lot 01 based on the peak retention times. Results are shown in Table 28.

TABLE 28

| RT (min) | Log $M_w$ | $M_w$ | Log $M_n$ | $M_n$ |
|---|---|---|---|---|
| 6.8 | 2.78 | 1.02 | 2.93 | 1.08 |
| 7.8 | 1.46 | 0.38 | 1.68 | 0.52 |
| 8.0 | 1.20 | 0.18 | 1.42 | 0.35 |

TABLE 28-continued

| RT (min) | Log $M_w$ | $M_w$ | Log $M_n$ | $M_n$ |
|---|---|---|---|---|
| | Average | 0.53 | Average | 0.65 |
| | | | PDI | 0.81 |

Lot 01 of AB-101 has a PDI of 0.81. This is in contrast to the PDI range of 0.9-1.2 for crofelemer as disclosed in WO 2012/101008. The larger PDI for crofelemer indicates that through the refining and fractionation process, crofelemer has greater heterogeniety in cross linking, network formation, chain length and branching than AB-101.

Example 8—Study of AB-101 in the Treatment of Participants with Mild to Moderate Atopic Dermatitis with or without Secondary Infection A randomized, double-blind, multicenter study to assess the safety and efficacy of topical AB-101 versus hydrogel vehicle in the treatment of participants with mild to moderate atopic dermatitis with or without secondary infection in male or female participants with mild to moderate infected or noninfected AD.

The objectives and endpoints of the study are shown in Table 29.

TABLE 29

| Objectives | Endpoints |
|---|---|
| Primary | |
| Objective: To evaluate the safety and tolerability of AB-101 hydrogel versus vehicle. | Frequency and severity of Adverse Events (AE). Study intervention discontinuation due to AEs. |
| Objective: To compare the 1-point change from baseline in IGA score between treatment arms in participants with infected (Cohort 1) and non-infected AD (Cohort 2) | Proportion of participants achieving at least a 1-point decrease in IGA score at Day 29 |
| Secondary | |
| Objective: To compare the EASI75 response between treatment arms in participants with infected (Cohort 1) and non-infected AD (Cohort 2) | EASI: Percent change from baseline in EASI total score at Day 29. |
| Objective: To compare the change in EASI score between treatment arms in participants with infected (Cohort 1) and non-infected AD (Cohort 2) | EASI: Percent change from baseline in EASI total score at Day 29. |
| Objective: To compare the 2-point change in IGA score between treatment arms in participants with infected (Cohort 1) and non-infected AD (Cohort 2) | Proportion of participants achieving at least a 2-point decrease in IGA score at Day2 9 |
| Hypothesis (H4): AB-101 is superior to vehicle alone | |
| Objective: To compare the time to 1-point change in IGA score between treatment arms in participants with infected (Cohort 1) and non-infected AD (Cohort 2) | Proportion of participants achieving at least a 1-point decrease in IGA score at Day 8, 15, 22, 29 |
| Objective: To compare the time to 2-point change in IGA score between treatment arms in participants with infected (Cohort 1) and non-infected AD (Cohort 2) | Proportion of participants achieving at least a 2-point decrease in IGA score at Day 8, 15, 22, 29 |
| Objective: To compare the change in SIRS between treatment arms in participants with infected (Cohort 1) and non-infected AD (Cohort 2) | SIRS calculated at Day 4, 8, 15, 22, 29 |
| Objective: To compare the change in percent BSA involvement between treatment arms in participants with infected (Cohort 1) and non-infected AD (Cohort 2) | BSA calculated using rule of nines at Day 8, 15, 22, 29 |
| Objective: To compare the change in POEM score between treatment arms in participants with infected (Cohort 1) and non-infected AD (Cohort 2) | Patient Oriented Eczema Measure reported at Day 8, 15, 22, 29 |

TABLE 29-continued

| Objectives | Endpoints |
|---|---|
| Objective: To compare the change in age-specific patient-reported outcome score between treatment arms in participants with infected (Cohort 1) and non-infected AD (Cohort 2) | The Dermatology Life Quality Index (DLQI)<br>The Children's Dermatology Life Quality Index (CDLQI)<br>The Infants Dermatitis Quality of Life Index (IDQOL)<br>POEM<br>Peak Pruritus NRS |
| Objective: To compare the bacteriology response between treatment arms in participants with infected (Cohort 1) and non-infected AD (Cohort 2) | Bacteriology response at Day 4, 8, 15, 22, 29 |

The overall study design is shown in Table 30.

TABLE 30

| | |
|---|---|
| Study Phase | Phase 2 |
| Primary Purpose | Treatment |
| Indication | Treatment of Mild to Moderate Atopic Dermatitis With or Without Secondary Infection |
| Population | Participants with Mild to Moderate Atopic Dermatitis |
| Study Type | Interventional |
| Intervention Model | Parallel<br>This is a multi-site study |
| Type of Control | Vehicle |
| Study Blinding | Double-blind with in-house blinding |
| Masking | Investigator<br>Participant<br>Sponsor |
| Estimated Duration of Study | The Sponsor estimates that the study will require approximately 6 months from the time the first participant (or their legally accepted representative) provides documented informed consent/assent until the last participant's last study-related contact. |

Study population: Approximately 60 male/female participants aged 2 years or older with mild to moderate AD with or without secondary infection will be enrolled into this study.

Intervention groups and study duration is summarized in Table 31.

TABLE 31

| | Intervention Group Name | Intervention | Drug Substance Concentration | Dose Frequency | Route of Admin. | Regimen/ Treatment Period | Use |
|---|---|---|---|---|---|---|---|
| Intervention | Cohort 1 - Infected AD participants | | | | | | |
| Groups | Arm A | AB-101 | 40% | BID | Topical | 28 days | Experimental |
| | Arm B | Vehicle | 0% | BID | Topical | 28 days | Experimental |
| | Cohort 2 - Non-infected AD participants | | | | | | |
| | Arm A | AB-101 | 40% | BID | Topical | 28 days | Experimental |
| | Arm B | Vehicle | 0% | BID | Topical | 28 days | Experimental |
| Total Number | 4 intervention groups across 2 cohorts | | | | | | |
| Duration of Participation | After a Screening phase of up to 14 days, each participant will be randomized to receive intervention with AB-101 hydrogel or hydrogel vehicle in a 2:1 ratio for 28 days or until one of the conditions for discontinuation of study intervention is met. The Screening and Day 1 visits may be combined. | | | | | | |

Inclusion Criteria—Participants are eligible to be included in the study only if all the following criteria apply. Male/female participants who are ≥2 years of age on the day of providing documented informed consent/assent. Have a clinical diagnosis of AD for at least 3 months, confirmed according to the criteria of Hanifin and Rajka (1980) at the Screening visit. Mild to moderate AD indicated by IGA score of 2 (mild) or 3 (moderate) at Screening and at Day 1 prior to application of study intervention. Have AD on the head (including face, but excluding hair-bearing scalp), neck, trunk (excluding groin and genitals), or limbs, covering at least 5% of total BSA at Screening and at Day 1 (Visit 1). Have an EASI total score of ≥3 to ≤21 at Screening and at Day 1. SIRS Score of ≥8 (Cohort 1) or <8 (Cohort 2). Participant on stable regimens (consistent use 14 days before Day 1) of all allowed oral and topical medications. Willing to refrain from using any topical products and any cosmetics or skin cleansers to the Target Lesion during the study intervention application period. Willing to refrain from application of study intervention to areas of skin that are not within the Target Lesion. Participants who are willing and able to comply with all scheduled visits, treatment plan, laboratory tests, lifestyle considerations, and other study procedures. A female participant is eligible to participate if she is not pregnant, not breastfeeding, and at least one of the following conditions applies: Not a Woman of Childbearing Potential (WOCBP) or a WOCBP who agrees to follow the contraceptive guidance. The participant (or legally acceptable representative if applicable) provides documented informed consent/assent for the study.

Exclusion Criteria—Participants are excluded from the study if any of the following criteria apply. Has unstable AD or any consistent requirement for high-potency topical corticosteroids to manage AD signs and symptoms. Has an active systemic infection requiring antibiotic treatment. Has recent or anticipated concomitant use of systemic or topical therapies that might alter the course of AD. Fitzpatrick skin type score of 6. Have received prior treatment with any monoclonal antibody, TYK2 and/or JAK inhibitors within 6 months or 5 half-lives (whichever is shorter) prior to Day 1. Has undergone treatment for any type of cancer (except squamous cell carcinoma, basal cell carcinoma, or carcinoma in situ of the skin, curatively treated with cryosurgery or surgical excision only). Active or potentially recurrent dermatologic condition other than AD that may confound evaluation. Current or recent history (approximately, within 3 months) of severe, progressive, or uncontrolled renal, hepatic, hematological, gastrointestinal, metabolic, endocrine, pulmonary, cardiovascular, or neurological disease. A history of any lymphoproliferative disorder (such as Epstein Barr Virus-related lymphoproliferative disorder), history of lymphoma, leukemia, malignancies or signs and symptoms suggestive of current lymphatic disease (Note: Adults with adequately treated or excised non-metastatic basal cell or squamous cell cancer of the skin, or cervical carcinoma in situ are allowed). A history of systemic (within approximately 3 months), chronic or acute skin infection (within approximately 2 weeks) requiring hospitalization, parenteral antimicrobial, antivirals, antiparasitics, antiprotozoals, or antifungals therapy, or as otherwise judged clinically significant by the investigator. Use of systemic antibiotics or systemic corticosteroids within 28 days prior to screening. Use of topical antiviral agents, topical antibacterial agents, topical antifungal agents, or topical corticosteroid agents within 14 days prior to Day 1. A known heritable immunodeficiency disorder. Undergone significant trauma or major surgery within 1 month prior to screening at the discretion of the investigator. Known hypersensitivity to AB-101 or any component of the vehicle. Other acute or chronic medical or psychiatric condition including recent (within the past year) or active suicidal ideation or behavior or laboratory abnormality that may increase the risk associated with study participation or investigational product administration or may interfere with the interpretation of study results and, in the judgment of the investigator, would make the participant inappropriate for entry into this study. A WOCBP who has a positive urine pregnancy test within 24 hours prior to randomization or treatment allocation. If the urine test is positive or cannot be confirmed as negative, a serum pregnancy test is required (Note: If 24 hours have elapsed between the screening pregnancy test and the first dose of study intervention, another pregnancy test (urine or serum) must be performed and must be negative for participant to start receiving study intervention). Has received a live or live-attenuated vaccine within 30 days prior to the first dose of study intervention. Administration of killed vaccine and mRNA vaccines is allowed. Is currently participating in or has participated in a study of an investigational agent or used an investigational device within 28 days prior to the first dose of study intervention. Has a known history of HIV, Hepatitis B or Hepatitis C infection (Note: No testing for HIV, Hepatitis C or Hepatitis C is required unless mandated by local health authority). Investigator site staff members directly involved in the conduct of the study and their family members; site staff members otherwise supervised by the investigator, are not eligible. Has a history of alcohol or substance abuse within 6 months prior to Screening that in the opinion of the investigator will preclude participation in the study. Has a history or current evidence of any condition, therapy, or laboratory abnormality that might confound the results of this study, interfere with the participant's participation for the full duration of the study, or is not in the best interest of the participant to participate, in the opinion of the treating investigator.

Discussion of Study Design

The Phase 2a, multicenter, randomized, double-blind, vehicle-controlled, parallel group study will assess the safety and efficacy of AB-101 topical hydrogel formulation when applied twice daily in participants with mild or moderate AD with or without secondary infection.

Participants will be screened within 14 days prior to the Day 1 dose of study intervention to confirm they meet the selection criteria for the study. The Screening visit and Day 1 visit may be combined. The treatment with study intervention will be BID for up to 4 weeks (28 days), followed by a follow-up visit 1 week (7 days) later as outlined in the SoA. The total study duration for a participant is approximately 5 weeks.

Pediatric and adult participants aged 2 years of age or older with mild or moderate AD dermatitis as determined by the IGA scale with or without secondary infection as determined by the investigator and confirmed with the SIRS scale will be enrolled. The study consists of 2 cohorts with 2 arms each. Each cohort will enroll 30 evaluable participants randomized in a 2:1 ratio to receive active or vehicle control study intervention:

Cohort 1: Mild or moderate AD with secondary infection

Cohort 2: Mild or moderate AD without secondary infection

A participant will enter the screening period once he/she has agreed to participate and has signed informed consent/assent. Participants with mild to moderate AD per the IGA scale and a total body surface area (BSA) involvement of ≥5% that includes involvement in targetable areas of skin and who meet all the inclusion criteria and none of the exclusion criteria, and who successfully complete the screening process, will be eligible to be enrolled.

Once enrolled, the participant will be randomized to receive either AB-101 or hydrogel vehicle (2:1 ratio) for topical application to targeted involved AD. The first dose will be applied at the clinic. The participant will be given a diary and printed instructions on how to apply the study intervention BID, ≥8 hours between applications, for up to 28 days. Participants will return to the study clinic on Days 4, 8, 15, 22, and 29, for a total of 5 study efficacy evaluation visits after screening. All participants will also return for a follow-up study visit on Day 36 or 7 days after the last dose.

Assessments of microbiology, IGA, EASI, SCORAD, SIRS, and BSA involvement will occur at Day 1 and every efficacy study visit (Days 4, 8, 15, 22, 29). Photography of lesions will be performed at these visits at selected sites.

A participant in Cohort 1 whose AD is judged by the investigator to demonstrate clinical progression of existing infection in AD-involved skin in the targeted area for study will be discontinued from study intervention and End of Treatment procedures are performed.

A participant in Cohort 2 whose AD is judged by the investigator to demonstrate clinical progression to clinically overt infected AD-involved skin in the targeted area for study will be discontinued from study intervention and End of Treatment procedures are performed.

Prematurely discontinued participants in Cohort 1 and Cohort 2 will continue study participation for 7 days to obtain follow-up outcome data.

Assuming 20% dropout rate, a total of approximately 72 participants (36 per cohort) will be randomized to ensure completion of approximately 60 participants (30 per cohort).

Investigators, participants, and the Sponsor study team will be blinded regarding study intervention.

All primary and secondary endpoints will be achieved.

The invention claimed is:

1. A method of treating atopic dermatitis in a subject in need thereof comprising topically administering to affected areas of the subject a pharmaceutical composition containing a therapeutically effective amount of filtered latex of *Croton lechleri*, wherein the therapeutically effect amount of filtered latex of *Croton lechleri* is about 40 wt %, wherein the atopic dermatitis is treated, and wherein the outcome is selected from a decrease in IGA score by at least 1 point, a decrease in EASI by at least 20%, an improvement in Peak Pruritus NRS score, and a combination thereof.

2. The method of claim 1, wherein the atopic dermatitis is mild to moderate.

3. The method of claim 1, wherein the *Croton lechleri* is *Croton lechleri* Müll. Arg.

4. The method of claim 1, wherein the therapeutically effective amount of filtered latex of *Croton lechleri* is 40 wt %.

5. The method of claim 1, wherein the subject is age 2 years or older.

6. The method of claim 1, wherein the pharmaceutical composition further comprises a pharmaceutically acceptable carrier.

7. The method of claim 1, wherein the pharmaceutical composition is a hydrogel.

8. The method of claim 1, wherein the decrease in IGA score is by about 1 to about 3 points.

9. The method of claim 1, wherein the decrease in IGA score occurs by day 29.

10. The method of claim 1, wherein the decrease in EASI by at least 50%.

11. The method of claim 1, wherein the decrease in EASI occurs by day 29.

12. The method of claim 1, further comprising an improvement in the SIRS score by at least 1.

13. The method of claim 11, wherein the improvement in the SIRS score occurs by day 29.

14. The method of claim 1, further comprising a reduction in percent BSA.

15. The method of claim 13, wherein the decrease in percent BSA occurs by day 29.

16. The method of claim 1, further comprising an improvement on one or more symptoms assessed by POEM.

17. The method of claim 16, wherein the improvement on one or more symptoms assessed by POEM occurs by day 29.

18. The method of claim 1, wherein the topical administration results in no pain upon application.

19. The method of claim 1, wherein the topical administration results in no drug adverse effects upon application.

20. The method of claim 1, wherein the topical administration results in minimal side effects.

21. The method of claim 1, wherein the atopic dermatitis is accompanied by bacterial colonization or primary or secondary bacterial infection is selected from the group consisting of *Streptococcus pyogenes*, MDR *Streptococcus pyogenes, Staphylococcus aureus*, methicillin-resistant *Staphylococcus aureus* (MRSA), Mupirocin-resistant MRSA, *Enterococcus faecalis, Streptococcus pneumoniae, Escherichia coli* (*E. coli*), *Pseudomonas aeruginosa*, MDR *Pseudomonas aeruginosa*, and Coagulase-negative *Staphylococcus.*

* * * * *